(12) United States Patent
Weinstein et al.

(10) Patent No.: US 10,499,997 B2
(45) Date of Patent: Dec. 10, 2019

(54) SYSTEMS AND METHODS FOR SURGICAL NAVIGATION

(71) Applicant: MAKO Surgical Corp., Ft. Lauderdale, FL (US)

(72) Inventors: Jeremy Weinstein, Santa Clara, CA (US); Andrei Danilchenko, Miami, FL (US); Jose Luis Moctezuma de la Barrera, Freiburg (DE)

(73) Assignee: MAKO Surgical Corp., Ft. Lauderdale, FL (US)

( * ) Notice: Subject to any disclaimer, the term of this patent is extended or adjusted under 35 U.S.C. 154(b) by 157 days.

(21) Appl. No.: 15/860,057

(22) Filed: Jan. 2, 2018

(65) Prior Publication Data

US 2018/0185100 A1 Jul. 5, 2018

Related U.S. Application Data

(60) Provisional application No. 62/441,713, filed on Jan. 3, 2017.

(51) Int. Cl.
| | |
|---|---|
| *A61B 34/20* | (2016.01) |
| *A61B 90/00* | (2016.01) |
| *A61F 2/46* | (2006.01) |
| *A61B 34/30* | (2016.01) |
| *A61B 90/50* | (2016.01) |

(Continued)

(52) U.S. Cl.
CPC ............ *A61B 34/20* (2016.02); *A61B 90/361* (2016.02); *A61F 2/461* (2013.01); *A61B 34/30* (2016.02); *A61B 2034/105* (2016.02); *A61B 2034/107* (2016.02); *A61B 2034/2048* (2016.02); *A61B 2034/2055* (2016.02); *A61B 2034/2057* (2016.02); *A61B 2034/2059* (2016.02); *A61B 2034/2065* (2016.02); *A61B 2034/2068* (2016.02); *A61B 2034/2072* (2016.02); *A61B 2034/252* (2016.02); *A61B 2090/372* (2016.02); *A61B 2090/373* (2016.02); *A61B 2090/395* (2016.02); *A61B 2090/3983* (2016.02); *A61B 2090/502* (2016.02); *A61F 2002/4633* (2013.01)

(58) Field of Classification Search
CPC ......... A61B 34/20; A61B 34/30; A61B 90/00; A61B 90/361; A61F 2/46; A61F 2/461
See application file for complete search history.

(56) References Cited

U.S. PATENT DOCUMENTS

| | | |
|---|---|---|
| 5,715,836 A | 2/1998 | Kliegis et al. |
| 6,069,932 A | 5/2000 | Peshkin et al. |

(Continued)

FOREIGN PATENT DOCUMENTS

| | | |
|---|---|---|
| WO | 0141070 A1 | 6/2001 |
| WO | 2005087125 A3 | 9/2005 |

(Continued)

OTHER PUBLICATIONS

English language abstract for WO 2013/100517 extracted from espacenet.com database on Feb. 19, 2018, 2 pages.

(Continued)

*Primary Examiner* — Christopher J Beccia
(74) *Attorney, Agent, or Firm* — Howard & Howard Attorneys PLLC

(57) ABSTRACT

System and methods for surgical navigation providing mixed reality visualization are provided. The mixed reality visualization depicts virtual images in conjunction with real objects to provide improved visualization to users.

18 Claims, 36 Drawing Sheets

(51) Int. Cl.
*A61B 34/10* (2016.01)
*A61B 34/00* (2016.01)

(56) References Cited

U.S. PATENT DOCUMENTS

| | | | |
|---|---|---|---|
| 6,252,599 | B1 | 6/2001 | Natsuko et al. |
| 6,450,978 | B1 | 9/2002 | Brosseau et al. |
| 6,533,737 | B1 | 3/2003 | Brosseau et al. |
| 6,856,324 | B2 | 2/2005 | Sauer et al. |
| 6,891,518 | B2 | 5/2005 | Sauer et al. |
| 7,367,809 | B2 | 5/2008 | Takahashi |
| 7,388,972 | B2 | 6/2008 | Kitson |
| 7,452,369 | B2 | 11/2008 | Barry |
| 7,472,437 | B2 | 1/2009 | Riley et al. |
| 7,491,219 | B2 | 2/2009 | Steinberg |
| 7,650,179 | B2 | 1/2010 | Redel et al. |
| 7,725,162 | B2 | 5/2010 | Malackowski et al. |
| 7,763,035 | B2 | 7/2010 | Melkent et al. |
| 7,815,644 | B2 | 10/2010 | Masini |
| 7,831,096 | B2 | 11/2010 | Williamson, Jr. |
| 7,831,292 | B2 | 11/2010 | Quaid et al. |
| 7,868,904 | B2 | 1/2011 | Morita et al. |
| RE42,194 | E | 3/2011 | Foley et al. |
| RE42,226 | E | 3/2011 | Foley et al. |
| 8,010,180 | B2 | 8/2011 | Quaid et al. |
| 8,060,186 | B2 | 11/2011 | Mohamed et al. |
| 8,068,648 | B2 | 11/2011 | DiSilvestro et al. |
| 8,095,200 | B2 | 1/2012 | Quaid, III |
| 8,099,155 | B2 | 1/2012 | Boese et al. |
| 8,105,339 | B2 | 1/2012 | Melkent et al. |
| 8,152,816 | B2 | 4/2012 | Tuma et al. |
| 8,314,815 | B2 | 11/2012 | Navab et al. |
| 8,331,634 | B2 | 12/2012 | Barth et al. |
| RE43,952 | E | 1/2013 | Uhl et al. |
| 8,364,245 | B2 | 1/2013 | Kruecker |
| RE44,305 | E | 6/2013 | Foley et al. |
| 8,472,120 | B2 | 6/2013 | Border et al. |
| 8,717,294 | B2 | 5/2014 | Weising et al. |
| 8,730,156 | B2 | 5/2014 | Weising et al. |
| 8,753,394 | B2 | 6/2014 | Zipnick et al. |
| 8,775,133 | B2 | 7/2014 | Schroeder |
| 8,820,929 | B2 | 9/2014 | Shea et al. |
| 8,842,893 | B2 | 9/2014 | Teichman et al. |
| 8,963,957 | B2 | 2/2015 | Skarulis |
| 9,041,691 | B1 | 5/2015 | Haskin et al. |
| 9,119,655 | B2 | 9/2015 | Bowling et al. |
| 9,123,155 | B2 | 9/2015 | Cunningham et al. |
| 9,161,679 | B2 | 10/2015 | Christiansen et al. |
| 9,230,368 | B2 | 1/2016 | Keane et al. |
| 9,241,682 | B2 | 1/2016 | Aram et al. |
| 9,256,987 | B2 | 2/2016 | Ackerman et al. |
| 9,269,275 | B2 | 2/2016 | Bell et al. |
| 9,310,883 | B2 | 4/2016 | Weising et al. |
| 9,348,141 | B2 | 5/2016 | Bar-Zeev et al. |
| 9,381,085 | B2 | 7/2016 | Axelson, Jr. et al. |
| 9,430,038 | B2 | 8/2016 | Ebstyne et al. |
| 9,529,195 | B2 | 12/2016 | Osterhout et al. |
| 9,566,120 | B2 | 2/2017 | Malackowski et al. |
| 9,645,785 | B1 | 5/2017 | Hannaford et al. |
| 2003/0093067 | A1 | 5/2003 | Panescu |
| 2004/0240715 | A1 | 12/2004 | Wicker et al. |
| 2005/0215879 | A1 | 9/2005 | Chuanggui |
| 2006/0098010 | A1 | 5/2006 | Dwyer et al. |
| 2006/0153454 | A1 | 7/2006 | Grimme |
| 2007/0118243 | A1 | 5/2007 | Schroeder et al. |
| 2007/0179626 | A1 | 8/2007 | de la Barrera et al. |
| 2007/0236514 | A1 | 10/2007 | Agusanto et al. |
| 2007/0248261 | A1 | 10/2007 | Zhou et al. |
| 2008/0058837 | A1 | 3/2008 | Steinberg |
| 2008/0108912 | A1 | 5/2008 | Node-Langlois |
| 2008/0243142 | A1 | 10/2008 | Gildenberg |
| 2008/0269596 | A1 | 10/2008 | Revie et al. |
| 2008/0286715 | A1 | 11/2008 | Choi |
| 2010/0094308 | A1 | 4/2010 | Tatsumi et al. |
| 2010/0228118 | A1 | 9/2010 | Maschke |
| 2011/0105895 | A1 | 5/2011 | Komblau et al. |
| 2011/0190637 | A1 | 8/2011 | Knobel et al. |
| 2011/0282189 | A1 | 11/2011 | Graumann |
| 2012/0022408 | A1 | 1/2012 | Hubschman et al. |
| 2012/0296163 | A1 | 11/2012 | Stopek |
| 2012/0306850 | A1 | 12/2012 | Balan et al. |
| 2013/0174213 | A1 | 7/2013 | Liu et al. |
| 2013/0187905 | A1 | 7/2013 | Vaddadi et al. |
| 2013/0201291 | A1 | 8/2013 | Liu et al. |
| 2013/0211232 | A1 | 8/2013 | Murphy et al. |
| 2013/0249947 | A1 | 9/2013 | Reitan |
| 2013/0290876 | A1 | 10/2013 | Anderson et al. |
| 2013/0314440 | A1 | 11/2013 | Simon et al. |
| 2014/0080086 | A1 | 3/2014 | Chen |
| 2014/0176533 | A1 | 6/2014 | Dillavou et al. |
| 2014/0200621 | A1 | 7/2014 | Malackowski et al. |
| 2014/0221823 | A1 | 8/2014 | Keogh et al. |
| 2014/0275760 | A1 | 9/2014 | Lee et al. |
| 2014/0368532 | A1 | 12/2014 | Keane et al. |
| 2014/0368537 | A1 | 12/2014 | Salter et al. |
| 2015/0010220 | A1 | 1/2015 | Teichman et al. |
| 2015/0051617 | A1 | 2/2015 | Takemura et al. |
| 2015/0062157 | A1 | 3/2015 | Dragnea |
| 2015/0084990 | A1 | 3/2015 | Laor |
| 2015/0146946 | A1 | 5/2015 | Elhawary et al. |
| 2015/0150537 | A1 | 6/2015 | Maruyama |
| 2015/0156028 | A1 | 6/2015 | Ballard et al. |
| 2015/0161821 | A1 | 6/2015 | Mazula |
| 2015/0193982 | A1 | 7/2015 | Mihelich et al. |
| 2015/0223905 | A1 | 8/2015 | Karmarkar et al. |
| 2015/0235434 | A1 | 8/2015 | Miller et al. |
| 2015/0305828 | A1 | 10/2015 | Park et al. |
| 2015/0317837 | A1 | 11/2015 | Sholudko et al. |
| 2015/0327946 | A1 | 11/2015 | Rotvold |
| 2016/0004917 | A1 | 1/2016 | Yoshida |
| 2016/0019715 | A1 | 1/2016 | Haddick et al. |
| 2016/0019716 | A1 | 1/2016 | Huang et al. |
| 2016/0019719 | A1 | 1/2016 | Osterhout et al. |
| 2016/0030126 | A1 | 2/2016 | Netravali et al. |
| 2016/0042562 | A1 | 2/2016 | Haswell et al. |
| 2016/0049005 | A1 | 2/2016 | Mullins et al. |
| 2016/0093108 | A1 | 3/2016 | Mao et al. |
| 2016/0095752 | A1 | 4/2016 | Srinivasan et al. |
| 2016/0104452 | A1 | 4/2016 | Guan et al. |
| 2016/0127702 | A1 | 5/2016 | Tsao et al. |
| 2016/0143699 | A1 | 5/2016 | Tanji |
| 2016/0163105 | A1 | 6/2016 | Hong et al. |
| 2016/0287337 | A1 | 10/2016 | Aram et al. |
| 2016/0299565 | A1 | 10/2016 | Sudarsky |
| 2016/0324580 | A1 | 11/2016 | Esterberg |
| 2017/0027651 | A1 | 2/2017 | Esterberg |
| 2017/0157854 | A1 | 6/2017 | Steurrys et al. |
| 2017/0257610 | A1 | 9/2017 | Vales et al. |

FOREIGN PATENT DOCUMENTS

| | | |
|---|---|---|
| WO | 2005091220 A1 | 9/2005 |
| WO | 2007108776 A3 | 9/2007 |
| WO | 2007111570 A3 | 10/2007 |
| WO | 2007115825 A1 | 10/2007 |
| WO | 2008103383 A1 | 8/2008 |
| WO | 2008121339 A3 | 10/2008 |
| WO | 2010081094 A3 | 7/2010 |
| WO | 2012135554 A1 | 10/2012 |
| WO | 2013095393 A1 | 6/2013 |
| WO | 2013100517 A1 | 7/2013 |
| WO | 2013120670 A3 | 8/2013 |
| WO | 2013145730 A1 | 10/2013 |
| WO | 2013175471 A1 | 11/2013 |
| WO | 2014013393 A3 | 1/2014 |
| WO | 2014200016 A1 | 12/2014 |
| WO | 2014204756 A1 | 12/2014 |
| WO | 2014204905 A1 | 12/2014 |
| WO | 2015008932 A1 | 1/2015 |
| WO | 2015030455 A1 | 3/2015 |
| WO | 2015058819 A1 | 4/2015 |
| WO | 2015114119 A1 | 8/2015 |
| WO | 2015127146 A1 | 8/2015 |
| WO | 2015134740 A1 | 9/2015 |

(56) References Cited

FOREIGN PATENT DOCUMENTS

| WO | 2015135055 A1 | 9/2015 |
|---|---|---|
| WO | 2015135059 A1 | 9/2015 |
| WO | 2015149616 A1 | 10/2015 |
| WO | 2015167160 A1 | 11/2015 |
| WO | 2015187335 A1 | 12/2015 |
| WO | 2015187620 A1 | 12/2015 |
| WO | 2016014384 A2 | 1/2016 |
| WO | 2016014871 A1 | 1/2016 |
| WO | 2016032807 A1 | 3/2016 |
| WO | 2016042256 A1 | 3/2016 |
| WO | 2016053906 A1 | 4/2016 |
| WO | 2016056004 A1 | 4/2016 |
| WO | 2016057433 A1 | 4/2016 |
| WO | 2016063166 A1 | 4/2016 |
| WO | 2016162789 A2 | 10/2016 |

OTHER PUBLICATIONS

English language abstract for WO 2013/145730 extracted from espacenet.com database on Feb. 19, 2018, 2 pages.

English language abstract for WO 2014/200016 extracted from espacenet.com database on Feb. 19, 2018, 2 pages.

English language abstract and machine-assisted English translation for WO 2015/008932 extracted from espacenet.com database on Feb. 19, 2018, 16 pages.

English language abstract for WO 2015/030455 extracted from espacenet.com database on Feb. 19, 2018, 2 pages.

English language abstract for WO 2016/042256 extracted from espacenet.com database on Feb. 19, 2018, 1 page.

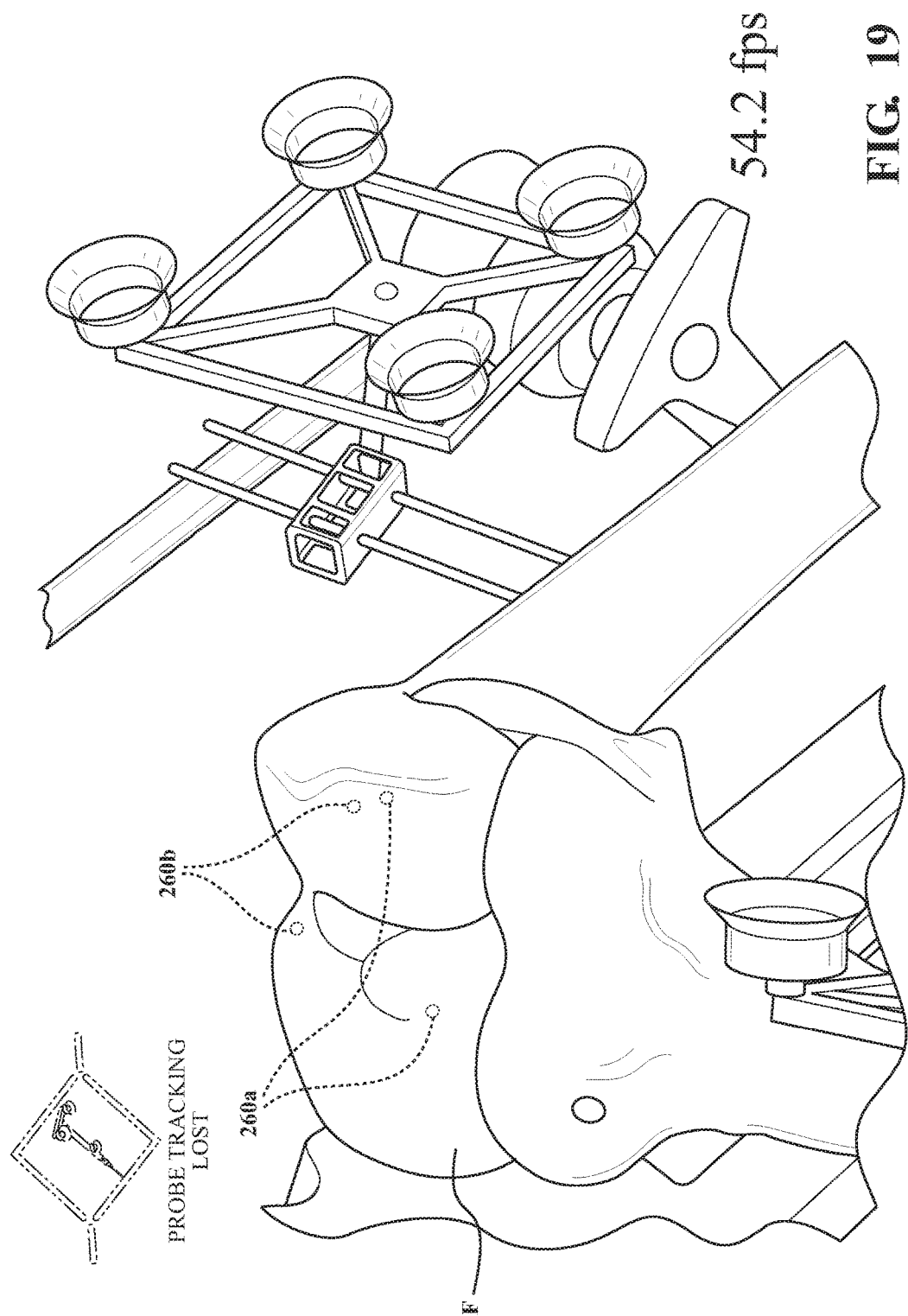

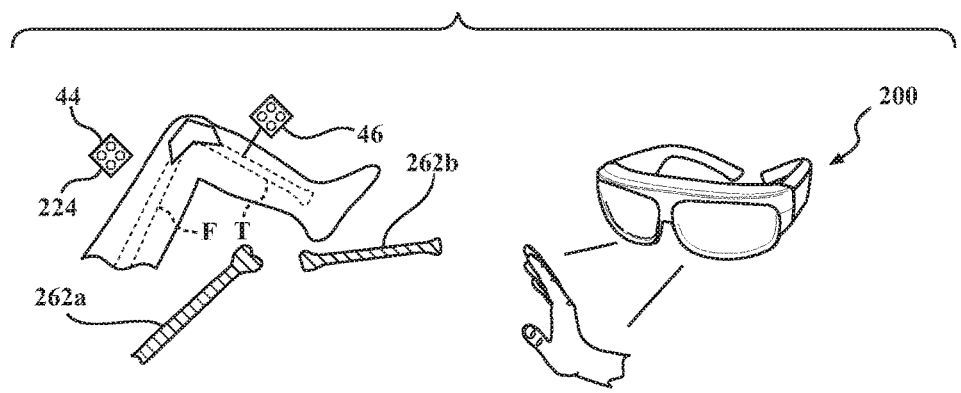
FIG. 28
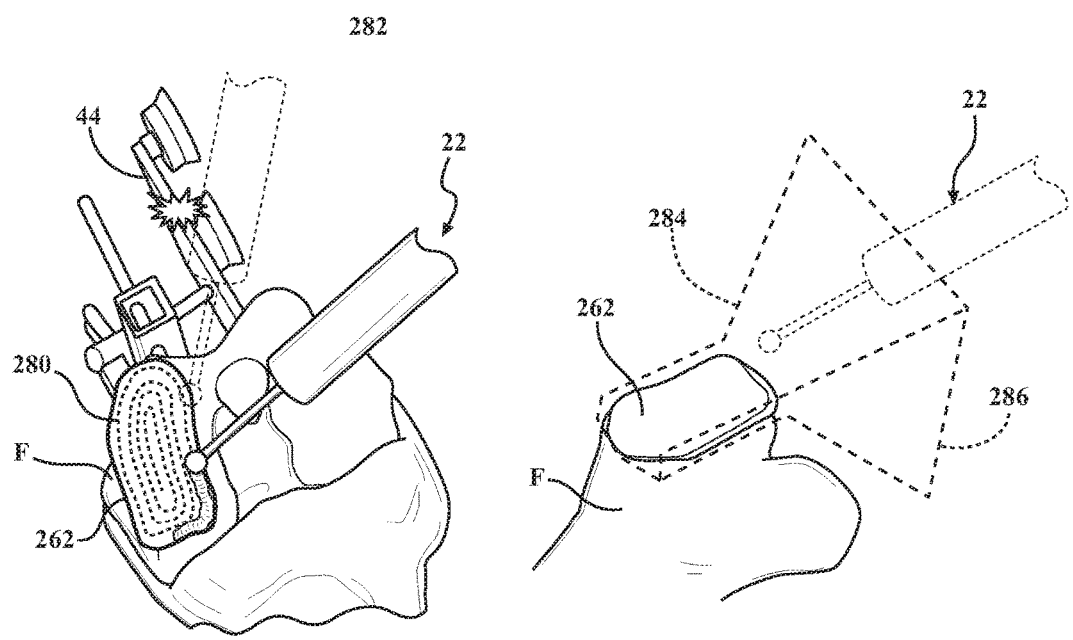
FIG. 29
FIG. 30

SYSTEMS AND METHODS FOR SURGICAL NAVIGATION

TECHNICAL FIELD

The disclosure relates generally to systems and methods for providing mixed reality visualization in cooperation with surgical navigation, such as before, during, and/or after surgical procedures.

BACKGROUND

Surgical navigation systems assist users in locating objects in one or more coordinate systems. Surgical navigation systems may employ light signals, sound waves, magnetic fields, radio frequency signals, etc. in order to track positions and/or orientations of the objects. Often the surgical navigation system includes tracking devices attached to the objects being tracked. A surgical navigation localizer cooperates with the tracking devices to ultimately determine positions and/or orientations of the objects. The surgical navigation system monitors movement of the objects via the tracking devices.

Surgeries in which surgical navigation systems are used include neurosurgery and orthopedic surgery, among others. Typically, surgical tools and anatomy being treated are tracked together in real-time in a common coordinate system with their relative positions and/or orientations shown on a display. In some cases, this visualization may include computer-generated images of the surgical tools and/or the anatomy displayed in conjunction with real video images of the surgical tools and/or the anatomy to provide mixed reality visualization. This visualization assists surgeons in performing the surgery. However, because the display is often located remotely from the surgical tools and/or the anatomy being treated, and because the view of the real video images is not usually aligned with the surgeon's point of view, the visualization can be awkward to the surgeon, especially when the surgeon regularly switches his/her gaze between the display and the actual surgical tools and/or the anatomy being treated. There is a need in the art to overcome one or more of these disadvantages.

Head-mounted displays (HMDs) are gaining popularity in certain industries, particularly the gaming industry. HMDs provide computer-generated images that are seemingly present in the real world. There are many surgical applications in which such HMDs could be employed. However, there is a need in the art for systems and methods to integrate such HMDs into surgical navigation systems. For example, surgical navigation systems often require registration of the surgical tools and/or the anatomy being treated to the common coordinate system. Typically such registration is performed with little visualization assistance making such registration cumbersome and difficult to quickly verify. When using HMDs for visualization, there is also a need to register the HMD to the common coordinate system, along with the surgical tools and/or the anatomy.

SUMMARY

In one embodiment, a surgical navigation system is provided comprising a head-mounted display operable in a HMD coordinate system. The head-mounted display comprises a camera for capturing images. A surgical navigation localizer has a localizer coordinate system. The localizer comprises one or more position sensors. A tracker is to be coupled to a real object so that the real object is trackable by the surgical navigation localizer. The tracker comprises a registration device having a registration coordinate system. The registration device comprises a plurality of registration markers for being analyzed in the images captured by the camera of the head-mounted display to determine a pose of the HMD coordinate system relative to the registration coordinate system. The registration device further comprises a plurality of tracking markers for being detected by the one or more position sensors of the localizer to determine a pose of the registration coordinate system relative to the localizer coordinate system, wherein positions of the registration markers are known with respect to positions of the tracking markers in the registration coordinate system.

In another embodiment, a mixed reality system comprises a head-mounted display operable in a HMD coordinate system. The head-mounted display comprises a camera for capturing images. A surgical navigation localizer has one or more position sensors for tracking a pose of a real object in a localizer coordinate system. A registration device has a registration coordinate system. The registration device comprises a plurality of registration markers for being analyzed in the images captured by the camera of the head-mounted display to determine a pose of the HMD coordinate system relative to the registration coordinate system. The registration device further comprises a plurality of tracking markers for being sensed by the one or more position sensors of the localizer to determine a pose of the registration coordinate system relative to the localizer coordinate system. Positions of the registration markers are known with respect to positions of the tracking markers in the registration coordinate system. At least one controller is configured to register the HMD coordinate system and the localizer coordinate system in response to a user directing the head-mounted display toward the registration markers so that the registration markers are within the images captured by the camera and in response to the one or more position sensors sensing the tracking markers.

In another embodiment, a mixed reality system comprises a head-mounted display having a HMD coordinate system. The head-mounted display comprises a camera for capturing images. A surgical navigation localizer has a housing and one or more position sensors for tracking a pose of a real object in a localizer coordinate system. A plurality of registration markers are disposed on the housing of the localizer in known positions in the localizer coordinate system. The registration markers are configured to be analyzed in the images captured by the camera of the head-mounted display to determine a pose of the localizer coordinate system relative to the HMD coordinate system. At least one controller is configured to register the HMD coordinate system and the localizer coordinate system in response to a user directing the head-mounted display toward the registration markers so that the registration markers are within the images captured by the camera.

In another embodiment, a mixed reality system comprises a head-mounted display having a HMD coordinate system. The head-mounted display comprises a camera for capturing images. A surgical navigation localizer comprises one or more position sensors for tracking a pose of a real object in a localizer coordinate system. A registration device has a registration coordinate system. The registration device comprises a plurality of registration markers for being analyzed in the images captured by the camera of the head-mounted display to determine a pose of the registration coordinate system relative to the HMD coordinate system. A registration probe has a registration tip. The registration probe comprises a plurality of tracking markers for being sensed by the one or more position sensors of the localizer to determine a position of the registration tip in the localizer coordinate system. A pose of the registration coordinate system with respect to the localizer coordinate system is determined upon placing the registration tip in a known location with respect to each of the registration markers and simultaneously sensing the tracking markers with the one or more position sensors. At least one controller is configured to register the HMD coordinate system and the localizer coordinate system in response to a user directing the head-mounted display toward the registration markers so that the registration markers are within the images captured by the camera and in response to the one or more position sensors sensing the tracking markers when the registration tip is placed in the known locations with respect to each of the registration markers.

In another embodiment, a method of calibrating registration of a HMD coordinate system and a localizer coordinate system is provided. The HMD coordinate system is associated with a head-mounted display and the localizer coordinate system is associated with a surgical navigation localizer. The method comprises registering the HMD coordinate system and the localizer coordinate system such that images displayed by the head-mounted display can be associated with real objects tracked by the localizer. Registration error is indicated to the user using a plurality of real calibration markers viewable by the user and a plurality of virtual calibration marker images displayed to the user. The virtual calibration marker images have a congruency with the real calibration markers so that the virtual calibration marker images are capable of being aligned with the real calibration markers whereby a magnitude of misalignment is indicative of the registration error. The registration of the HMD coordinate system and the localizer coordinate system is calibrated to reduce the registration error by receiving input from the user associated with adjusting positions of the virtual calibration marker images relative to the real calibration markers to better align the virtual calibration marker images with the real calibration markers.

In another embodiment, a method of determining registration error in registration of a HMD coordinate system and a localizer coordinate system is provided. The HMD coordinate system is associated with a head-mounted display and the localizer coordinate system is associated with a surgical navigation localizer. The method comprises registering the HMD coordinate system and the localizer coordinate system such that images displayed with the head-mounted display can be associated with real objects tracked by the localizer. HMD-based positions of a plurality of error-checking markers are determined by analyzing images captured by a camera of the head-mounted display. Localizer-based positions of the plurality of error-checking markers are determined by placing a tip of a navigation probe in a known location with respect to each of the error-checking markers. Navigation markers of the navigation probe are simultaneously sensed with one or more position sensors of the localizer. The HMD-based positions are then compared with the localizer-based positions of each of the error-checking markers to determine the registration error for each of the error-checking markers.

In another embodiment, a method of determining registration error in registration of a HMD coordinate system and a localizer coordinate system is provided. The HMD coordinate system is associated with a head-mounted display and the localizer coordinate system is associated with a surgical navigation localizer. The method comprises registering the HMD coordinate system and the localizer coordinate system such that images displayed with the head-mounted display can be associated with real objects tracked by the localizer. Localizer-based positions of a plurality of error-checking markers are determined by placing a tip of a navigation probe at locations associated with each of the error-checking markers. Navigation markers of the navigation probe are simultaneously sensed with one or more position sensors of the localizer. The plurality of error-checking markers are located on a substrate separate from the head-mounted display and the localizer. Indicator images are displayed through the head-mounted display to the user that indicates to the user the registration error for each of the error-checking markers. The substrate comprises a visible error scale and the indicator images are displayed with respect to the visible error scale to manually determine the registration error.

In another embodiment, a method of registering a robotic coordinate system and a localizer coordinate system using a head-mounted display is provided. The robotic coordinate system is associated with a surgical robot. The localizer coordinate system is associated with a surgical navigation localizer. The head-mounted display has a HMD coordinate system. The method comprises registering the HMD coordinate system and the localizer coordinate system such that images displayed with the head-mounted display can be associated with real objects tracked by the localizer. An initial registration of the robotic coordinate system and the localizer coordinate system is performed by sensing base tracking markers mounted to the surgical robot and by sensing tool tracking markers temporarily mounted to a surgical tool coupled to the surgical robot. Protocol images are displayed with the head-mounted display that define a registration protocol for the user to follow to continue registration of the robotic coordinate system and the localizer coordinate system. The registration protocol comprises movement indicators to indicate to the user movements to be made with the surgical tool while the tool tracking markers are temporarily mounted to the surgical tool. Registration of the robotic coordinate system and the localizer coordinate system is finalized in response to the user moving the surgical tool in accordance with the protocol images displayed by the head-mounted display.

In another embodiment, a method of verifying registration of a model coordinate system and a localizer coordinate system is provided. The model coordinate system is associated with a virtual model of a patient's bone and the localizer coordinate system is associated with a surgical navigation localizer. The method comprises registering a HMD coordinate system and the localizer coordinate system. The HMD coordinate system is associated with a head-mounted display such that images displayed with the head-mounted display can be associated with real objects tracked by the localizer. The model coordinate system and the localizer coordinate system are registered by placing a tip of a navigation probe at locations on the patient's bone and simultaneously sensing navigation markers of the navigation probe with one or more position sensors of the localizer. Landmark images are displayed with the head-mounted display that define a verification protocol for the user to follow to verify the registration of the model coordinate system and the localizer coordinate system. The landmark images depict virtual landmarks associated with the virtual model of the patient's bone. The landmark images are displayed to the user with the head-mounted display as being overlaid on the patient's bone such that the user is able to verify registration by placing the tip of the navigation probe on the patient's bone while positioning the tip of the navigation probe in desired positions relative to the user's visualization of the landmark images.

In another embodiment, a method of verifying registration of a model coordinate system and a localizer coordinate system is provided. The model coordinate system is associated with a virtual model of a patient's bone and the localizer coordinate system is associated with a surgical navigation localizer. The method comprises registering a HMD coordinate system and the localizer coordinate system. The HMD coordinate system is associated with a head-mounted display such that images displayed with the head-mounted display can be associated with real objects tracked by the localizer. The model coordinate system and the localizer coordinate system are registered by placing a tip of a navigation probe at locations on the patient's bone and simultaneously sensing navigation markers of the navigation probe with one or more position sensors of the localizer. First landmark images are displayed with the head-mounted display that define a verification protocol for the user to follow to verify the registration of the model coordinate system and the localizer coordinate system. The first landmark images depict virtual landmarks associated with the virtual model of the patient's bone. A model image is displayed that represents at least a portion of the virtual model. The first landmark images are displayed to the user with the head-mounted display as being overlaid on the patient's bone such that the user is able to verify registration by placing the tip of the navigation probe on the patient's bone while positioning the tip of the navigation probe in desired positions relative to the user's visualization of the first landmark images. The model image and second landmark images are further displayed to the user with the head-mounted display in an offset and magnified manner with respect to the patient's bone such that an axis of the patient's bone is parallel and offset to a corresponding axis of the model image such that the user is able to verify registration by placing the tip of the navigation probe on the patient's bone while simultaneously visualizing a virtual position of the tip of the navigation probe relative to the second landmark images.

In another embodiment, a method of verifying registration of a model coordinate system and a localizer coordinate system is provided. The model coordinate system is associated with a virtual model of a patient's bone and the localizer coordinate system is associated with a surgical navigation localizer. The method comprises registering a HMD coordinate system and the localizer coordinate system. The HMD coordinate system is associated with a head-mounted display such that images displayed with the head-mounted display can be associated with real objects tracked by the localizer. The model coordinate system and the localizer coordinate system are registered by placing a tip of a navigation probe at locations on the patient's bone and simultaneously sensing navigation markers of the navigation probe with one or more position sensors of the localizer. Landmark images are displayed with the head-mounted display that define a verification protocol for the user to follow to verify the registration of the model coordinate system and the localizer coordinate system. The landmark images depict virtual landmarks associated with the virtual model of the patient's bone. The landmark images are displayed to the user with the head-mounted display in an overlaid manner with respect to the patient's bone such that the user is able to verify registration by placing the tip of the navigation probe on the patient's bone adjacent to each of the landmark images and capturing points on the patient's bone adjacent to each of the landmark images to determine if the points on the patient's bone are within a predetermined tolerance to the virtual landmarks.

In another embodiment, a method of verifying registration of a model coordinate system and a localizer coordinate system is provided. The model coordinate system is associated with a virtual model of a patient's bone and the localizer coordinate system is associated with a surgical navigation localizer. The method comprises registering a HMD coordinate system and the localizer coordinate system. The HMD coordinate system is associated with a head-mounted display such that images displayed with the head-mounted display can be associated with real objects tracked by the localizer. The model coordinate system and the localizer coordinate system are registered by placing a tip of a navigation probe at locations on the patient's bone and simultaneously sensing navigation markers of the navigation probe with one or more position sensors of the localizer. Landmark images are displayed with the head-mounted display that define a verification protocol for the user to follow to verify the registration of the model coordinate system and the localizer coordinate system. The landmark images depict virtual landmarks associated with the virtual model of the patient's bone. A model image is displayed that represents at least a portion of the virtual model. The model image and the landmark images are displayed to the user with the head-mounted display with respect to the patient's bone. The model image is displayed to the user with a predefined transparency with respect to the landmark images to avoid occluding the user's view of the landmark images. The landmark images are displayed in varying colors based upon location of the virtual landmarks on the virtual model of the patient's bone relative to the user's viewing angle.

In another embodiment, a method of verifying registration of a model coordinate system and a localizer coordinate system is provided. The model coordinate system is associated with a virtual model of a patient's bone and the localizer coordinate system is associated with a surgical navigation localizer. The method comprises registering a HMD coordinate system and the localizer coordinate system. The HMD coordinate system is associated with a head-mounted display such that images displayed with the head-mounted display can be associated with real objects tracked by the localizer. The model coordinate system and the localizer coordinate system are registered by placing a tip of a navigation probe at locations on the patient's bone and simultaneously sensing navigation markers of the navigation probe with one or more position sensors of the localizer. Landmark images are displayed with the head-mounted display that define a verification protocol for the user to follow to verify the registration of the model coordinate system and the localizer coordinate system. The landmark images depict virtual landmarks associated with the virtual model of the patient's bone. Display of the landmark images to the user is based on distances of the tip of the navigation probe relative to the virtual landmarks such that one of the virtual landmarks closest to the tip of the navigation probe is depicted to the user in a manner that distinguishes the one of the virtual landmarks relative to the remaining virtual landmarks.

In another embodiment, a method of verifying registration of a model coordinate system and a localizer coordinate system is provided. The model coordinate system is associated with a virtual model of a patient's bone and the localizer coordinate system is associated with a surgical navigation localizer. The method comprises registering a HMD coordinate system and the localizer coordinate system. The HMD coordinate system is associated with a head-mounted display such that images displayed with the head-mounted display can be associated with real objects tracked by the localizer. The model coordinate system and the localizer coordinate system are registered by placing a tip of a navigation probe at locations on the patient's bone and simultaneously sensing navigation markers of the navigation probe with one or more position sensors of the localizer. Landmark images are displayed with the head-mounted display that define a verification protocol for the user to follow to verify the registration of the model coordinate system and the localizer coordinate system. The landmark images depict virtual landmarks associated with the virtual model of the patient's bone. The landmark images are controlled based on a status of the virtual landmarks, wherein the status of the virtual landmarks comprises one of a captured status, a miscaptured status, and an uncaptured status. The landmark images of the virtual landmarks that have a captured status are not displayed. The landmark images of the virtual landmarks that have a miscaptured status are displayed in a first color. The landmark images of the virtual landmarks that have an uncaptured status are displayed in a second color, different than the first color.

In another embodiment, a method of visually representing a volume of material to be removed from a patient's bone with a surgical tool is provided. The method comprises defining the volume of material to be removed from the patient's bone in a virtual model of the patient's bone. The virtual model of the patient's bone has a model coordinate system. The model coordinate system is registered to an operational coordinate system such that the virtual model and the volume of material to be removed from the patient's bone, as defined in the virtual model, are transformed to the operational coordinate system. A HMD coordinate system is registered to the operational coordinate system. The HMD coordinate system is associated with a head-mounted display. One or more images are displayed with the head-mounted display that represent at least a portion of the virtual model and the volume of material to be removed from the patient's bone in the operational coordinate system. The one or more images are displayed to the user with the head-mounted display in an offset manner with respect to the patient's bone such that an axis of the patient's bone is offset to a corresponding axis of the one or more images such that the user is able to visualize the volume of material to be removed from the patient's bone. The volume of material to be removed is depicted in a first color and portions of the patient's bone to remain are depicted in a second color, different than the first color.

In another embodiment, a method of visually representing a volume of material to be removed from a patient's bone with a surgical tool is provided. The method comprises defining the volume of material to be removed from the patient's bone in a virtual model of the patient's bone. The virtual model of the patient's bone has a model coordinate system. The model coordinate system is registered to an operational coordinate system such that the virtual model is transformed to the operational coordinate system. A HMD coordinate system is registered to the operational coordinate system. The HMD coordinate system is associated with a head-mounted display. One or more images are displayed with the head-mounted display that represent at least a portion of the virtual model and the volume of material to be removed from the patient's bone in the operational coordinate system. The one or more images are displayed to the user with the head-mounted display in an overlaid manner with respect to the patient's bone such that the user is able to visualize the volume of material to be removed from the patient's bone. The volume of material to be removed is depicted in a first color and portions of the patient's bone to remain are depicted in a second color, different than the first color.

In another embodiment, a method of visually representing a surgical plan for a surgical procedure is provided. The method comprises receiving a virtual model of a patient's bone. The virtual model has a model coordinate system. The model coordinate system is registered to an operational coordinate system. A HMD coordinate system and the operational coordinate system are registered. The HMD coordinate system is associated with a head-mounted display. A model image is displayed with the head-mounted display that represents at least a portion of the patient's bone. The model image is displayed with the head-mounted display to a user. One of a plurality of secondary images are selectively displayed with the head-mounted display. The plurality of secondary images comprises a target image that represents a volume of material to be removed from the patient's bone and an implant image that represents an implant to be placed on the patient's bone once the volume of material is removed from the patient's bone. The plurality of secondary images are configured to be overlaid on the model image with the model image being displayed with a predefined transparency.

In another embodiment, a method of visually representing a volume of material to be removed from a patient's bone with a surgical tool is provided. The surgical tool has a tool coordinate system. The method comprises defining the volume of material to be removed from the patient's bone in a virtual model of the patient's bone. The virtual model has a model coordinate system. The model coordinate system is registered to an operational coordinate system. The tool coordinate system is registered to the operational coordinate system. A HMD coordinate system and the operational coordinate system are registered. The HMD coordinate system is associated with a head-mounted display. A model image is displayed with the head-mounted display that represents the volume of material to be removed from the patient's bone in the operational coordinate system. The virtual model is altered as the surgical tool removes material from the patient's bone to account for removed material by subtracting volumes associated with the surgical tool from the virtual model. The model image is updated with the head-mounted display based on the altered virtual model to visually represent to the user remaining material to be removed from the patient's bone.

In another embodiment, a method of visually representing a patient's bone to be treated by a surgical robotic arm is provided. The method comprises receiving a virtual model of the patient's bone. The virtual model has a model coordinate system. The model coordinate system is registered to an operational coordinate system. A HMD coordinate system and the operational coordinate system are registered. The HMD coordinate system is associated with a head-mounted display. One or more images are displayed with the head-mounted display that represent at least a portion of the patient's bone. The one or more images are displayed to the user with the head-mounted display in an offset manner with respect to the patient's bone such that an axis of the patient's bone is offset with respect to a corresponding axis of the one or more images. The direction of the offset of the one or more images displayed to the user is based on a position of the surgical robotic arm relative to the patient's bone.

BRIEF DESCRIPTION OF THE DRAWINGS

Advantages of the present invention will be readily appreciated as the same becomes better understood by reference to the following detailed description when considered in connection with the accompanying drawings wherein:

FIG. 19 is a perspective view of a femur showing a different view of the method of FIG. 16.

FIG. 28 illustrates the use of gesture commands to control gross registration of bone models to actual bones.

FIG. 29 is a perspective view of a femur with model images overlaid on the femur by the HMD that represent the cut-volume model and a tool path for a surgical tool.

FIG. 30 illustrates a cutting boundary for the surgical tool.

DETAILED DESCRIPTION

Figure 1:
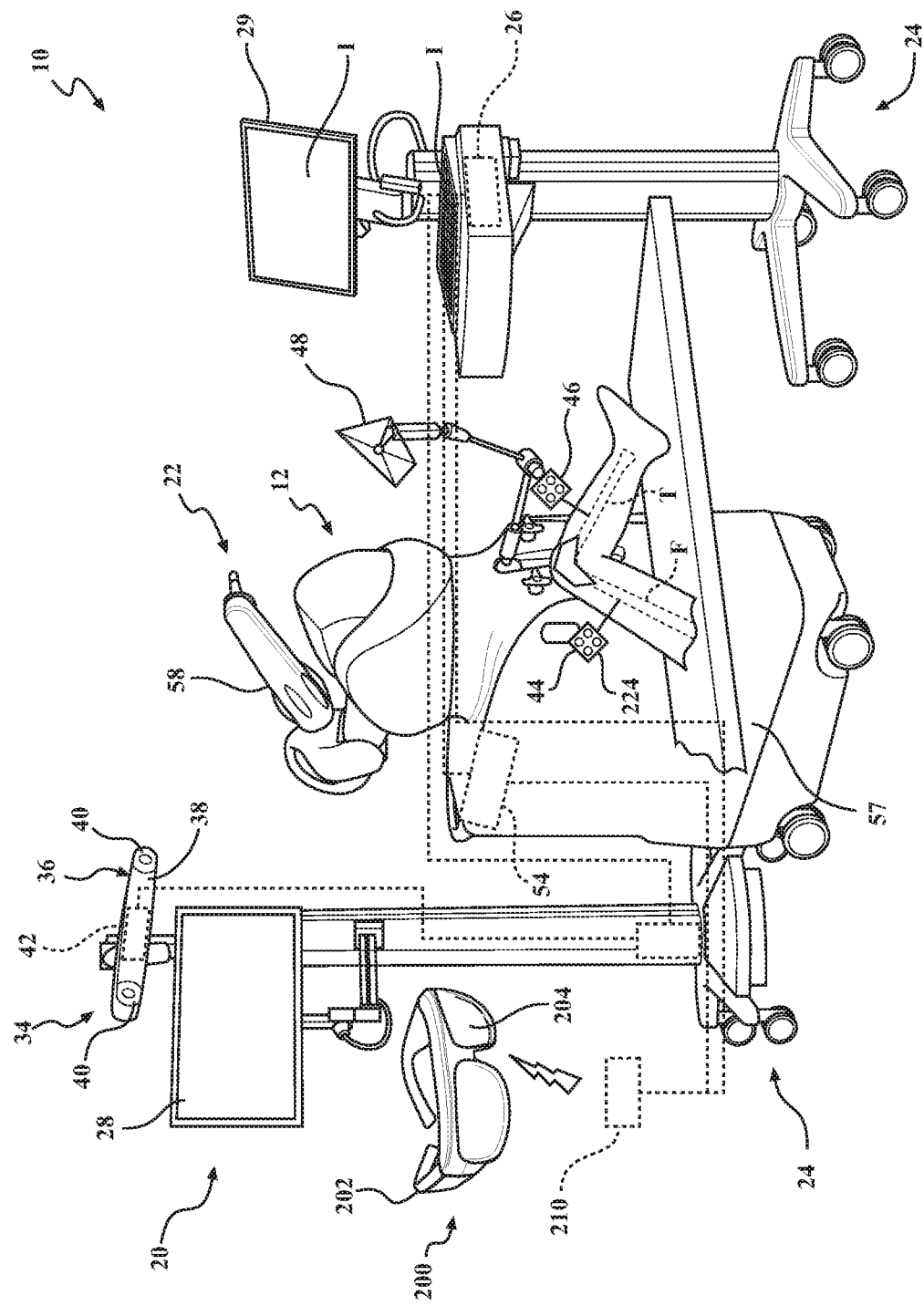
FIG. 1 is a perspective view of a robotic system.
Figure 2:
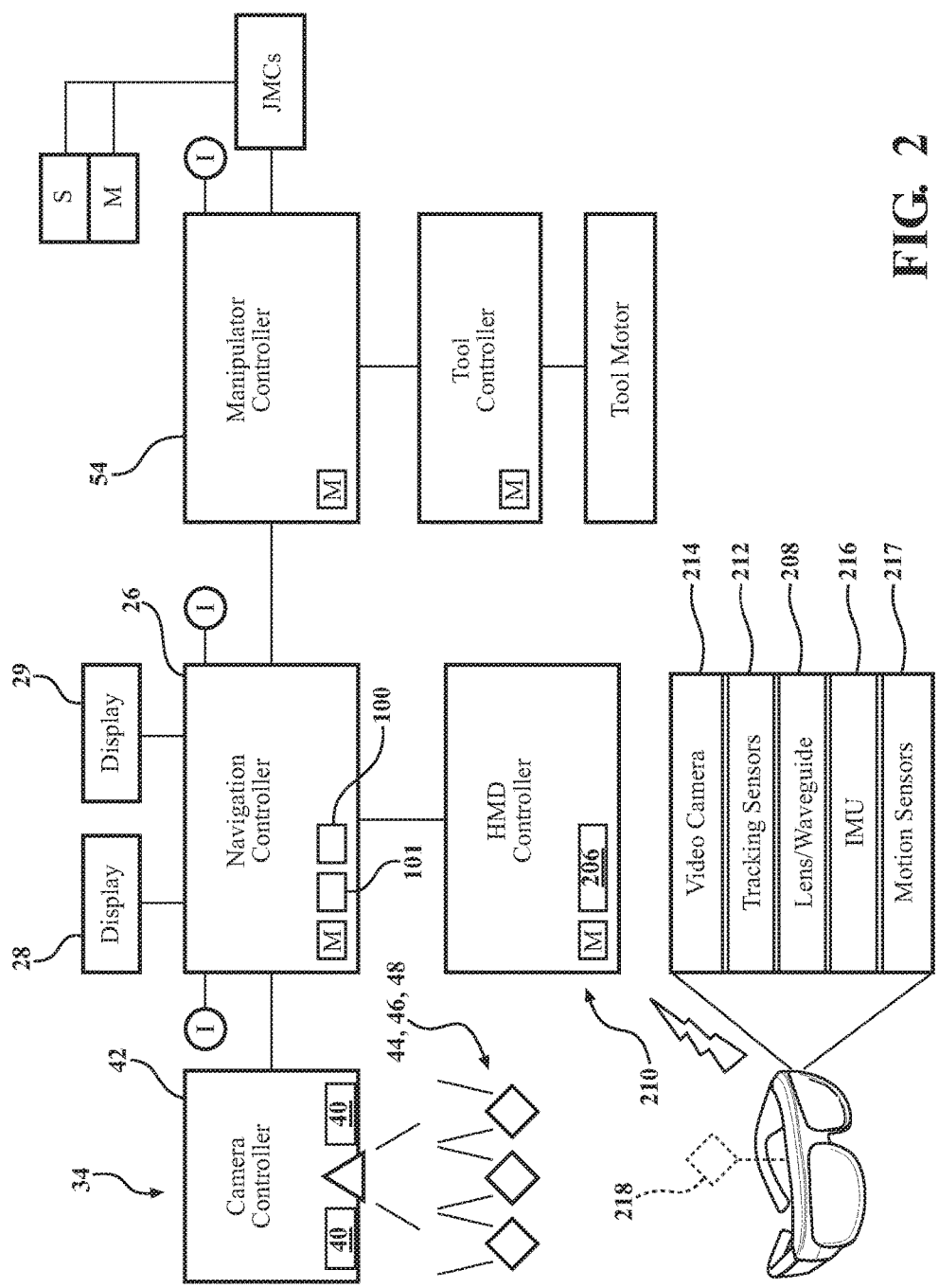
FIG. 2 is a schematic view of a control system.

Referring to FIG. 1 a surgical robotic system 10 for treating a patient is illustrated. The robotic system 10 is shown in a surgical setting such as an operating room of a medical facility. In the embodiment shown, the robotic system 10 includes a manipulator 12 and a navigation system 20. The navigation system 20 is set up to track movement of various real objects in the operating room. Such real objects include, for example, a surgical tool 22, a femur F of a patient, and a tibia T of the patient. The navigation system 20 tracks these objects for purposes of displaying their relative positions and orientations to the surgeon and, in some cases, for purposes of controlling or constraining movement of the surgical tool 22 relative to virtual cutting boundaries (not shown) associated with the femur F and tibia T. An exemplary control scheme for the robotic system 10 is shown in FIG. 2.

The navigation system 20 includes one or more computer cart assemblies 24 that houses one or more navigation controllers 26. A navigation interface is in operative communication with the navigation controller 26. The navigation interface includes one or more displays 28, 29 adjustably mounted to the computer cart assembly 24 or mounted to separate carts as shown. Input devices I such as a keyboard and mouse can be used to input information into the navigation controller 26 or otherwise select/control certain aspects of the navigation controller 26. Other input devices I are contemplated including a touch screen, voice-activation, gesture sensors, and the like.

A surgical navigation localizer 34 communicates with the navigation controller 26. In the embodiment shown, the localizer 34 is an optical localizer and includes a camera unit 36. In other embodiments, the localizer 34 employs other modalities for tracking, e.g., radio frequency (RF), ultrasonic, electromagnetic, inertial, and the like. The camera unit 36 has a housing 38 comprising an outer casing that houses one or more optical position sensors 40. In some embodiments at least two optical sensors 40 are employed, preferably three or four. The optical sensors 40 may be separate charge-coupled devices (CCD). In one embodiment three, one-dimensional CCDs are employed. Two-dimensional or three-dimensional sensors could also be employed. It should be appreciated that in other embodiments, separate camera units, each with a separate CCD, or two or more CCDs, could also be arranged around the operating room. The CCDs detect light signals, such as infrared (IR) signals.

Camera unit 36 is mounted on an adjustable arm to position the optical sensors 40 with a field-of-view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation controller 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation controller 26.

Position and orientation signals and/or data are transmitted to the navigation controller 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System," hereby incorporated by reference.

The navigation controller 26 can be a personal computer or laptop computer. Navigation controller 26 has the displays 28, 29, central processing unit (CPU) and/or other processors, memory (not shown), and storage (not shown). The navigation controller 26 is loaded with software as described below. The software converts the signals received from the camera unit 36 into data representative of the position and orientation of the objects being tracked.

Navigation system 20 is operable with a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Trackers 44, 46 could also be mounted like those shown in U.S. Patent Application Pub. No. 2014/0200621, filed on Jan. 16, 2014, entitled, "Navigation Systems and Methods for Indicating and Reducing Line-of-Sight Errors," hereby incorporated by reference herein. In additional embodiments, a tracker (not shown) is attached to the patella to track a position and orientation of the patella. In yet further embodiments, the trackers 44, 46 could be mounted to other tissue types or parts of the anatomy.

A base tracker 48 is shown coupled to the manipulator 12. In other embodiments, a tool tracker (not shown) may be substituted for the base tracker 48. The tool tracker may be integrated into the surgical tool 22 during manufacture or may be separately mounted to the surgical tool 22 (or to an end effector attached to the manipulator 12 of which the surgical tool 22 forms a part) in preparation for surgical procedures. The working end of the surgical tool 22, which is being tracked by virtue of the base tracker 48, may be referred to herein as an energy applicator, and may be a rotating bur, electrical ablation device, probe, or the like.

In the embodiment shown, the surgical tool 22 is attached to the manipulator 12. Such an arrangement is shown in U.S. Pat. No. 9,119,655, entitled, "Surgical Manipulator Capable of Controlling a Surgical Instrument in Multiple Modes," the disclosure of which is hereby incorporated by reference.

The optical sensors 40 of the localizer 34 receive light signals from the trackers 44, 46, 48. In the illustrated embodiment, the trackers 44, 46, 48 are passive trackers. In this embodiment, each tracker 44, 46, 48 has at least three passive tracking elements or markers (e.g., reflectors) for transmitting light signals (e.g., reflecting light emitted from the camera unit 36) to the optical sensors 40. In other embodiments, active tracking markers can be employed. The active markers can be, for example, light emitting diodes transmitting light, such as infrared light. Active and passive arrangements are possible.

The navigation controller 26 includes a navigation processor. It should be understood that the navigation processor could include one or more processors to control operation of the navigation controller 26. The processors can be any type of microprocessor or multi-processor system. The term processor is not intended to limit the scope of any embodiment to a single processor.

The camera unit 36 receives optical signals from the trackers 44, 46, 48 and outputs to the navigation controller 26 signals relating to the position of the tracking markers of the trackers 44, 46, 48 relative to the localizer 34. Based on the received optical signals, navigation controller 26 generates data indicating the relative positions and orientations of the trackers 44, 46, 48 relative to the localizer 34. In one version, the navigation controller 26 uses well known triangulation methods for determining position data.

Prior to the start of the surgical procedure, additional data are loaded into the navigation controller 26. Based on the position and orientation of the trackers 44, 46, 48 and the previously loaded data, navigation controller 26 determines the position of the working end of the surgical tool 22 (e.g., the centroid of a surgical bur) and/or the orientation of the surgical tool 22 relative to the tissue against which the working end is to be applied. In some embodiments, the navigation controller 26 forwards these data to a manipulator controller 54. The manipulator controller 54 can then use the data to control the manipulator 12. This control can be like that described in U.S. Pat. No. 9,119,655, entitled, "Surgical Manipulator Capable of Controlling a Surgical Instrument in Multiple Modes," the disclosure of which is hereby incorporated by reference or like that described in U.S. Pat. No. 8,010,180, entitled, "Haptic Guidance System and Method," hereby incorporated by reference.

In one embodiment, the manipulator 12 is controlled to stay within a preoperatively defined virtual boundary set by the surgeon or others (not shown), which defines the material of the femur F and tibia T to be removed by the surgical tool 22. More specifically, each of the femur F and tibia T has a target volume of material that is to be removed by the working end of the surgical tool 22 (to make room for implants, for instance). The target volumes are defined by one or more virtual cutting boundaries. The virtual cutting boundaries define the surfaces of the bone that should remain after the procedure. The navigation system 20 tracks and controls the surgical tool 22 to ensure that the working end, e.g., the surgical bur, only removes the target volume of material and does not extend beyond the virtual cutting boundary, as disclosed in U.S. Pat. No. 9,119,655, entitled, "Surgical Manipulator Capable of Controlling a Surgical Instrument in Multiple Modes," the disclosure of which is hereby incorporated by reference, or as disclosed in U.S. Pat. No. 8,010,180, hereby incorporated by reference.

The virtual cutting boundary may be defined within a virtual model of the femur F and tibia T, or separately from the virtual model or models of the femur F and tibia T. The virtual cutting boundary may be represented as a mesh surface, constructive solid geometry (CSG), voxels, or using other boundary representation techniques. The surgical tool 22 cuts away material from the femur F and tibia T to receive an implant. The surgical implants may include unicompartmental, bicompartmental, or total knee implants as shown in U.S. Pat. No. 9,381,085, entitled, "Prosthetic Implant and Method of Implantation," the disclosure of which is hereby incorporated by reference. Other implants, such as hip implants, shoulder implants, spine implants, and the like are also contemplated. The focus of the description on knee implants is merely exemplary as these concepts can be equally applied to other types of surgical procedures, including those performed without placing implants.

The navigation controller 26 also generates image signals that indicate the relative position of the working end to the tissue. These image signals are applied to the displays 28, 29. The displays 28, 29, based on these signals, generate images that allow the surgeon and staff to view the relative position of the working end to the surgical site. The displays, 28, 29, as discussed above, may include a touch screen or other input/output device that allows entry of commands.

Figure 3:
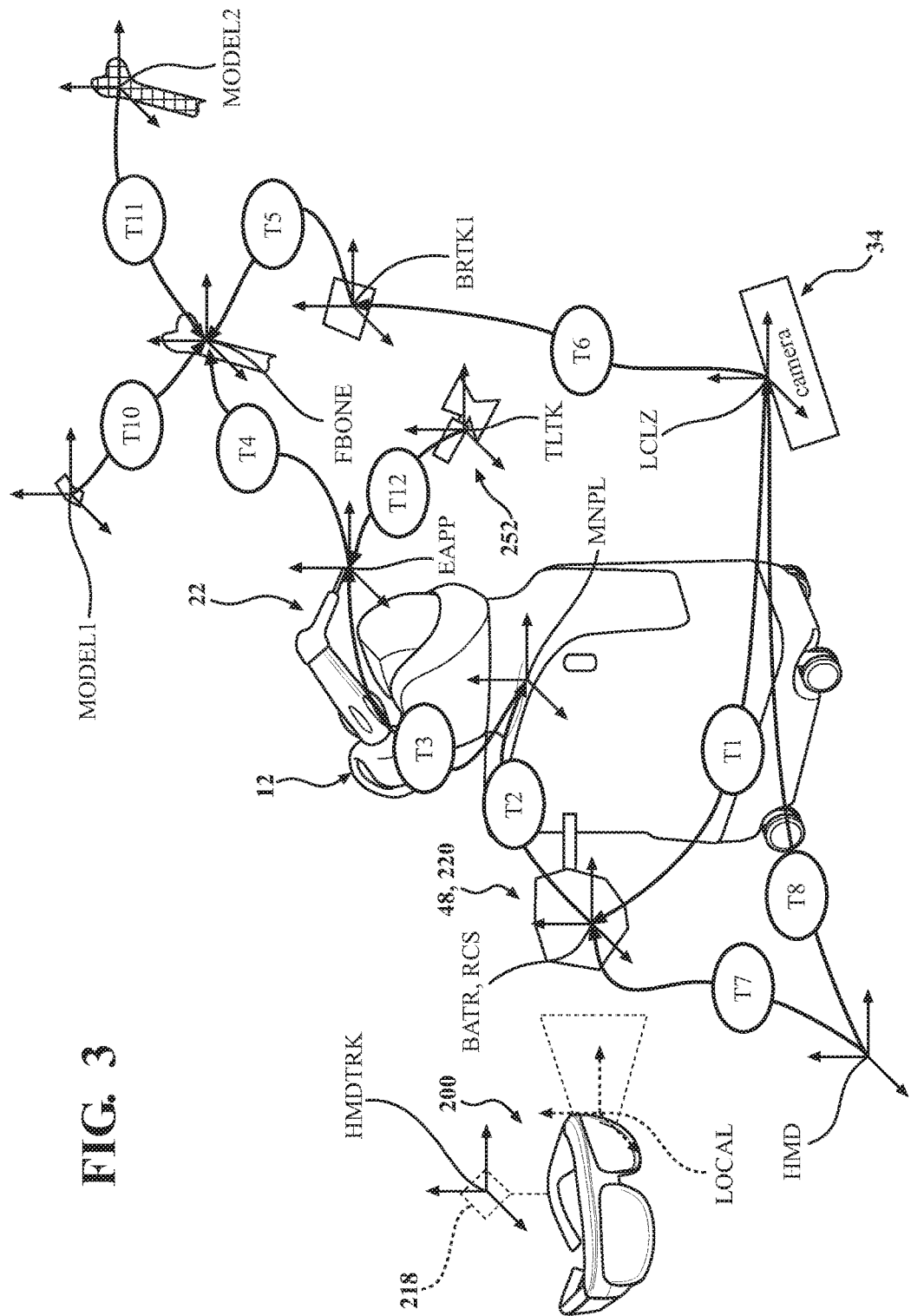
FIG. 3 is an illustration of various transforms used in navigation.

Referring to FIG. 3, tracking of objects is generally conducted with reference to a localizer coordinate system LCLZ. The localizer coordinate system has an origin and an orientation (a set of x, y, and z axes). During the procedure one goal is to keep the localizer coordinate system LCLZ in a known position. An accelerometer (not shown) mounted to the localizer 34 may be used to track sudden or unexpected movement of the localizer coordinate system LCLZ, as may occur when the localizer 34 is inadvertently bumped by surgical personnel.

Each tracker 44, 46, 48 and object being tracked also has its own coordinate system separate from the localizer coordinate system LCLZ. Components of the navigation system 20 that have their own coordinate systems are the bone trackers 44, 46 (only one of which is shown in FIG. 3) and the base tracker 48. These coordinate systems are represented as, respectively, bone tracker coordinate systems BTRK1, BTRK2 (only BTRK1 shown), and base tracker coordinate system BATR.

Navigation system 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the procedure, pre-operative images of the femur F and tibia T are generated (or of other tissues in other embodiments). These images may be based on MRI scans, radiological scans or computed tomography (CT) scans of the patient's anatomy. These images or three-dimensional models developed from these images are mapped to the femur coordinate system FBONE and tibia coordinate system TBONE using well known methods in the art (see transform T11). One of these models is shown in FIG. 3 with model coordinate system MODEL2. These images/models are fixed in the femur coordinate system FBONE and tibia coordinate system TBONE. As an alternative to taking pre-operative images, plans for treatment can be developed in the operating room (OR) from kinematic studies, bone tracing, and other methods. The models described herein may be represented by mesh surfaces, constructive solid geometry (CSG), voxels, or using other model constructs.

During an initial phase of the procedure, the bone trackers 44, 46 are firmly affixed to the bones of the patient. The pose (position and orientation) of coordinate systems FBONE and TBONE are mapped to coordinate systems BTRK1 and BTRK2, respectively (see transform T5). In one embodiment, a pointer instrument, such as disclosed in U.S. Pat. No. 7,725,162 to Malackowski, et al., hereby incorporated by reference, having its own tracker, may be used to register the femur coordinate system FBONE and tibia coordinate system TBONE to the bone tracker coordinate systems BTRK1 and BTRK2, respectively, and in some cases, also provides input for mapping the models of the femur F (MODEL2) and tibia to the femur coordinate system FBONE and the tibia coordinate system TBONE (e.g., by touching anatomical landmarks on the actual bone that are also identified in the models so that the models can be fit to the bone using known best-fit matching techniques). Given the fixed relationship between the bones and their bone trackers 44, 46, positions and orientations of the femur F and tibia T in the femur coordinate system FBONE and tibia coordinate system TBONE can be transformed to the bone tracker coordinate systems BTRK1 and BTRK2 so the camera unit 36 is able to track the femur F and tibia T by tracking the bone trackers 44, 46. These pose-describing data are stored in memory integral with both manipulator controller 54 and navigation controller 26.

The working end of the surgical tool 22 has its own coordinate system. In some embodiments, the surgical tool 22 comprises a handpiece and an accessory that is removably coupled to the handpiece. The accessory may be referred to as the energy applicator and may comprise a bur, an electrosurgical tip, an ultrasonic tip, or the like. Thus, the working end of the surgical tool 22 may comprise the energy applicator. The coordinate system of the surgical tool 22 is referenced herein as coordinate system EAPP. The origin of the coordinate system EAPP may represent a centroid of a surgical cutting bur, for example. In other embodiments, the accessory may simply comprise a probe or other surgical tool with the origin of the coordinate system EAPP being a tip of the probe. The pose of coordinate system EAPP is registered to the pose of base tracker coordinate system BATR before the procedure begins (see transforms T1, T2, T3). Accordingly, the poses of these coordinate systems EAPP, BATR relative to each other are determined. The pose-describing data are stored in memory integral with both manipulator controller 54 and navigation controller 26.

Referring to FIG. 2, a localization engine 100 is a software module that can be considered part of the navigation system 20. Components of the localization engine 100 run on navigation controller 26. In some embodiments, the localization engine 100 may run on the manipulator controller 54.

Localization engine 100 receives as inputs the optically-based signals from the camera controller 42 and, in some embodiments, non-optically based signals from the tracker controller. Based on these signals, localization engine 100 determines the pose of the bone tracker coordinate systems BTRK1 and BTRK2 in the localizer coordinate system LCLZ (see transform T6). Based on the same signals received for the base tracker 48, the localization engine 100 determines the pose of the base tracker coordinate system BATR in the localizer coordinate system LCLZ (see transform T1).

The localization engine 100 forwards the signals representative of the poses of trackers 44, 46, 48 to a coordinate transformer 102. Coordinate transformer 102 is a navigation system software module that runs on navigation controller 26. Coordinate transformer 102 references the data that defines the relationship between the pre-operative images of the patient and the bone trackers 44, 46. Coordinate transformer 102 also stores the data indicating the pose of the working end of the surgical tool 22 relative to the base tracker 48.

During the procedure, the coordinate transformer 102 receives the data indicating the relative poses of the trackers 44, 46, 48 to the localizer 34. Based on these data, the previously loaded data, and the below-described encoder data from the manipulator 12, the coordinate transformer 102 generates data indicating the relative positions and orientations of the coordinate system EAPP and the bone coordinate systems, FBONE and TBONE.

As a result, coordinate transformer 102 generates data indicating the position and orientation of the working end of the surgical tool 22 relative to the tissue (e.g., bone) against which the working end is applied. Image signals representative of these data are forwarded to displays 28, 29 enabling the surgeon and staff to view this information. In certain embodiments, other signals representative of these data can be forwarded to the manipulator controller 54 to guide the manipulator 12 and corresponding movement of the surgical tool 22.

Coordinate transformer 102 is also operable to determine the position and orientation (pose) of any coordinate system described herein relative to another coordinate system by utilizing known transformation techniques, e.g., translation and rotation of one coordinate system to another based on various transforms T described herein. As is known, the relationship between two coordinate systems is represented by a six degree of freedom relative pose, a translation followed by a rotation, e.g., the pose of a first coordinate system in a second coordinate system is given by the translation from the second coordinate system's origin to the first coordinate system's origin and the rotation of the first coordinate system's coordinate axes in the second coordinate system. The translation is given as a vector. The rotation is given by a rotation matrix.

The surgical tool 22 forms part of the end effector of the manipulator 12. The manipulator 12 has a base 57, a plurality of links 58 extending from the base 57, and a plurality of active joints (not numbered) for moving the surgical tool 22 with respect to the base 57. The manipulator 12 has the ability to operate in a manual mode or a semi-autonomous mode in which the surgical tool 22 is moved along a predefined tool path, as described in U.S. Pat. No. 9,119,655, entitled, "Surgical Manipulator Capable of Controlling a Surgical Instrument in Multiple Modes," the disclosure of which is hereby incorporated by reference, or the manipulator 12 may be configured to move in the manner described in U.S. Pat. No. 8,010,180, hereby incorporated by reference.

The manipulator controller 54 can use the position and orientation data of the surgical tool 22 and the patient's anatomy to control the manipulator 12 as described in U.S. Pat. No. 9,119,655, entitled, "Surgical Manipulator Capable of Controlling a Surgical Instrument in Multiple Modes," the disclosure of which is hereby incorporated by reference, or to control the manipulator 12 as described in U.S. Pat. No. 8,010,180, hereby incorporated by reference.

The manipulator controller 54 may have a central processing unit (CPU) and/or other manipulator processors, memory (not shown), and storage (not shown). The manipulator controller 54, also referred to as a manipulator computer, is loaded with software as described below. The manipulator processors could include one or more processors to control operation of the manipulator 12. The processors can be any type of microprocessor or multi-processor system. The term processor is not intended to limit any embodiment to a single processor.

A plurality of position sensors S are associated with the plurality of links 58 of the manipulator 12. In one embodiment, the position sensors S are encoders. The position sensors S may be any suitable type of encoder, such as rotary encoders. Each position sensor S is associated with a joint actuator, such as a joint motor M. Each position sensor S is a sensor that monitors the angular position of one of six motor driven links 58 of the manipulator 12 with which the position sensor S is associated. Multiple position sensors S may be associated with each joint of the manipulator 12 in some embodiments. The manipulator 12 may be in the form of a conventional robot or other conventional machining apparatus, and thus the components thereof shall not be described in detail.

In some modes, the manipulator controller 54 determines the desired location to which the surgical tool 22 should be moved. Based on this determination, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers JMCs that control the joints of the manipulator 12 to move the plurality of links 58 and thereby move the surgical tool 22 from the current location to the desired location. In other modes, the manipulator 12 is capable of being manipulated as described in U.S. Pat. No. 8,010,180, hereby incorporated by reference, in which case the actuators are controlled by the manipulator controller 54 to provide gravity compensation to prevent the surgical tool 22 from lowering due to gravity and/or to activate in response to a user attempting to place the working end of the surgical tool 22 beyond a virtual boundary.

In order to determine the current location of the surgical tool 22, data from the position sensors S is used to determine measured joint angles. The measured joint angles of the joints are forwarded to a forward kinematics module, as known in the art. Based on the measured joint angles and preloaded data, the forward kinematics module determines the pose of the surgical tool 22 in a manipulator coordinate system MNPL (see transform T3 in FIG. 3). The preloaded data are data that define the geometry of the plurality of links 58 and joints. With this encoder-based data, the manipulator controller 54 and/or navigation controller 26 can transform coordinates from the localizer coordinate system LCLZ into the manipulator coordinate system MNPL, vice versa, or can transform coordinates from one coordinate system into any other coordinate system described herein using conventional transformation techniques. In many cases, the coordinates of interest associated with the surgical tool 22 (e.g., the tool center point or TCP), the virtual boundaries, and the tissue being treated, are transformed into a common coordinate system for purposes of relative tracking and display.

In the embodiment shown in FIG. 3, transforms T1-T6 are utilized to transform all relevant coordinates into the femur coordinate system FBONE so that the position and/or orientation of the surgical tool 22 can be tracked relative to the position and orientation of the femur (e.g., the femur model) and/or the position and orientation of the volume of material to be treated by the surgical tool 22 (e.g., a cut-volume model: see transform T10). The relative positions and/or orientations of these objects can also be represented on the displays 28, 29 to enhance the user's visualization before, during, and/or after surgery.

A head-mounted display (HMD) 200 is employed to enhance visualization before, during, and/or after surgery. The HMD 200 can be used to visual the same objects previously described as being visualized on the displays 28, 29, and can also be used to visualize other objects, features, instructions, warnings, etc. The HMD 200 can be used to assist with visualization of the volume of material to be cut from the patient, to help visualize the size of implants and/or to place implants for the patient, to assist with registration and calibration of objects being tracked via the navigation system 20, to see instructions and/or warnings, among other uses, as described further below.

The HMD 200 may be a HoloLens® provided by Microsoft Corporation, which is referred to as a mixed reality HMD owing to its overlay of computer-generated images onto the real world. The HMD 200, such as the Hololens® provided by Microsoft Corporation is able to track itself in a global coordinate system (e.g., its external environment), map features of the external environment, and locate objects in the external environment (using 4 environment cameras, a depth camera, and/or a RGB photo/video camera) using "inside-out" tracking technology. In the embodiment described herein, the HMD also provides a computational holographic display capable of displaying virtual images so that they appear to be at desired coordinates in a desired coordinate system, i.e., they are virtually overlaid onto the real world and appear to users to be located in the real world environment at desired coordinates in the real world environment. Other types of mixed reality HMDs may also be used such as those that overlay computer-generated images onto video images of the real world. The HMD 200 may comprise a cathode ray tube display, liquid crystal display, liquid crystal on silicon display, or organic light-emitting diode display. The HMD 200 may comprise see-through techniques like that described herein comprising a diffractive waveguide, holographic waveguide, polarized waveguide, reflective waveguide, or switchable waveguide. Examples of suitable HMDs are described in the following patents, all of which are hereby incorporated herein by reference: U.S. Pat. No. 9,529,195, entitled, "See-through Computer Display Systems"; U.S. Pat. No. 9,348,141, entitled, "Low-latency Fusing of Virtual and Real Content"; U.S. Pat. No. 9,230,368, entitled "Hologram Anchoring and Dynamic Positioning"; and U.S. Pat. No. 8,472,120, entitled, "See-through Near-eye Display Glasses with a Small Scale Image Source."

Referring to FIGS. 1 and 2, the HMD 200 comprises a head-mountable structure 202, which may be in the form of an eyeglass and may include additional headbands or supports to hold the HMD 200 on the user's head. In other embodiments, the HMD 200 may be integrated into a helmet or other structure worn on the user's head, neck, and/or shoulders.

The HMD 200 has visor 204 and a lens/waveguide arrangement 208. The lens/waveguide arrangement 208 is configured to be located in front of the user's eyes when the HMD is placed on the user's head. The waveguide transmits the computer-generated images to the user's eyes while at the same time, real images are seen through the waveguide (it being transparent) such that the user sees mixed reality (virtual and real).

An HMD controller 210 comprises an image generator 206 that generates the computer-generated images (also referred to as virtual images or holographic images) and that transmits those images to the user through the lens/waveguide arrangement 208. The HMD controller 210 controls the transmission of the computer-generated images to the lens/waveguide arrangement 208 of the HMD 200. The HMD controller 210 may be a separate computer, located remotely from the support structure 202 of the HMD 200, or may be integrated into the support structure 202 of the HMD 200. The HMD controller 210 may be a laptop computer, desktop computer, microcontroller, or the like with memory, one or more processors (e.g., multi-core processors), input devices I, output devices (fixed display in addition to HMD 200), storage capability, etc. The HMD controller 210 may generate the computer-generated images in a manner that gives the user the impression of the computer-generated images being at desired coordinates relative to the real objects. In some cases, the HMD controller 210 is able to generate the computer-generated images (e.g., holograms) in a manner that locks the images in a desired coordinate system (e.g., a world coordinate system or other coordinate system of real objects that may be fixed or movable). The HMD controller 210 may be configured to generate such images in the manner described in the following patents, all of which are hereby incorporated herein by reference: U.S. Pat. No. 9,256,987, entitled, "Tracking Head Movement When Wearing Mobile Device"; U.S. Pat. No. 9,430,038, entitled, "World-locked Display Quality Feedback"; U.S. Pat. No. 9,529,195, entitled, "See-through Computer Display Systems"; U.S. Pat. No. 9,348,141, entitled, "Low-latency Fusing of Virtual and Real Content"; U.S. Pat. No. 9,230,368, entitled "Hologram Anchoring and Dynamic Positioning"; and U.S. Pat. No. 8,472,120, entitled, "See-through Near-eye Display Glasses with a Small Scale Image Source." Such images may also be generated in the manner described in U.S. Patent Application Pub. No. 2012/0306850, entitled, "Distributed Asynchronous Localization and Mapping for Augmented Reality," hereby incorporated herein by reference.

The HMD 200 comprises a plurality of tracking sensors 212 that are in communication with the HMD controller 210. In some cases, the tracking sensors 212 are provided to establish a global (world) coordinate system for the HMD 200, also referred to as an HMD coordinate system. The HMD coordinate system is established by these tracking sensors 212, which may comprise CMOS sensors or other sensor types, in some cases combined with IR depth sensors (e.g., depth camera), to layout the space surrounding the HMD 200, such as using structure-from-motion techniques or the like, as described in the patents previously incorporated herein by reference. In one embodiment, four tracking sensors 212 and one depth sensor are employed.

The HMD 200 also comprises a photo/video camera 214 in communication with the HMD controller 210. The camera 214 may be used to obtain photographic or video images 214 with the HMD 200, which can be useful in identifying objects or markers attached to objects, as will be described further below.

The HMD 200 further comprises an inertial measurement unit IMU 216 in communication with the HMD controller 210. The IMU 216 may comprise one or more 3-D accelerometers, 3-D gyroscopes, and the like to assist with determining a position and/or orientation of the HMD 200 in the HMD coordinate system or to assist with tracking relative to other coordinate systems. The HMD 200 may also comprise an infrared motion sensor 217 to recognize gesture commands from the user. Other types of gesture sensors are also contemplated. The motion sensor 217 may be arranged to project infrared light or other light in front of the HMD 200 so that the motion sensor 217 is able to sense the user's hands, fingers, or other objects for purposes of determining the user's gesture command and controlling the HMD 200, HMD controller 210, navigation controller 26, and/or manipulator controller 54 accordingly. Gesture commands can be used for any type of input used by the system 10.

In order for the HMD 200 to be effectively used, the HMD 200 is registered to one or more objects used in the operating room, such as the tissue being treated, the surgical tool 22, the manipulator 12, the trackers 44, 46, 48, the localizer 34, and/or the like. In one embodiment, the HMD coordinate system is a global coordinate system (e.g., a coordinate system of the fixed surroundings as shown in FIG. 3). In this case, a local coordinate system LOCAL is associated with the HMD 200 to move with the HMD 200 so that the HMD 200 is always in a known position and orientation in the HMD coordinate system. The HMD 200 utilizes the four tracking sensors 212 and/or the depth camera to map the surroundings and establish the HMD coordinate system. The HMD 200 then utilizes the camera 214 alone, or in conjunction with the depth camera, to find objects in the HMD coordinate system. In some embodiments, the HMD 200 uses the camera 214 to capture video images of markers attached to the objects and then determines the location of the markers in the local coordinate system LOCAL of the HMD 200 using motion tracking techniques and then converts (transforms) those coordinates to the HMD coordinate system. Methods of tracking the pose of the HMD 200 in the HMD coordinate system, and to determine the three dimensional locations of features within the environment are described in U.S. Patent Application Pub. No. 2013/0201291, entitled, "Head Pose Tracking Using a Depth Camera," and U.S. Patent Application Pub. No. 2012/0306850, entitled, "Distributed Asynchronous Localization and Mapping for Augmented Reality," both of which are hereby incorporated herein by reference.

In another embodiment, a separate HMD tracker 218 (see FIG. 3), similar to the trackers 44, 46, 48, could be mounted to the HMD 200 (e.g., fixed to the support structure 202). In this version, the HMD tracker 218 would have its own HMD tracker coordinate system HMDTRK that is in a known position/orientation relative to the local coordinate system LOCAL or could be calibrated to the local coordinate system LOCAL using conventional calibration techniques. In this embodiment, the local coordinate system LOCAL becomes the HMD coordinate system and the transforms T7 and T8 would instead originate therefrom. The localizer 34 could then be used to track movement of the HMD 200 via the HMD tracker 218 and transformations could then easily be calculated to transform coordinates in the local coordinate system LOCAL to the localizer coordinate system LCLZ, the femur coordinate system FBONE, the manipulator coordinate system MNPL, or other coordinate system.

Figure 4:
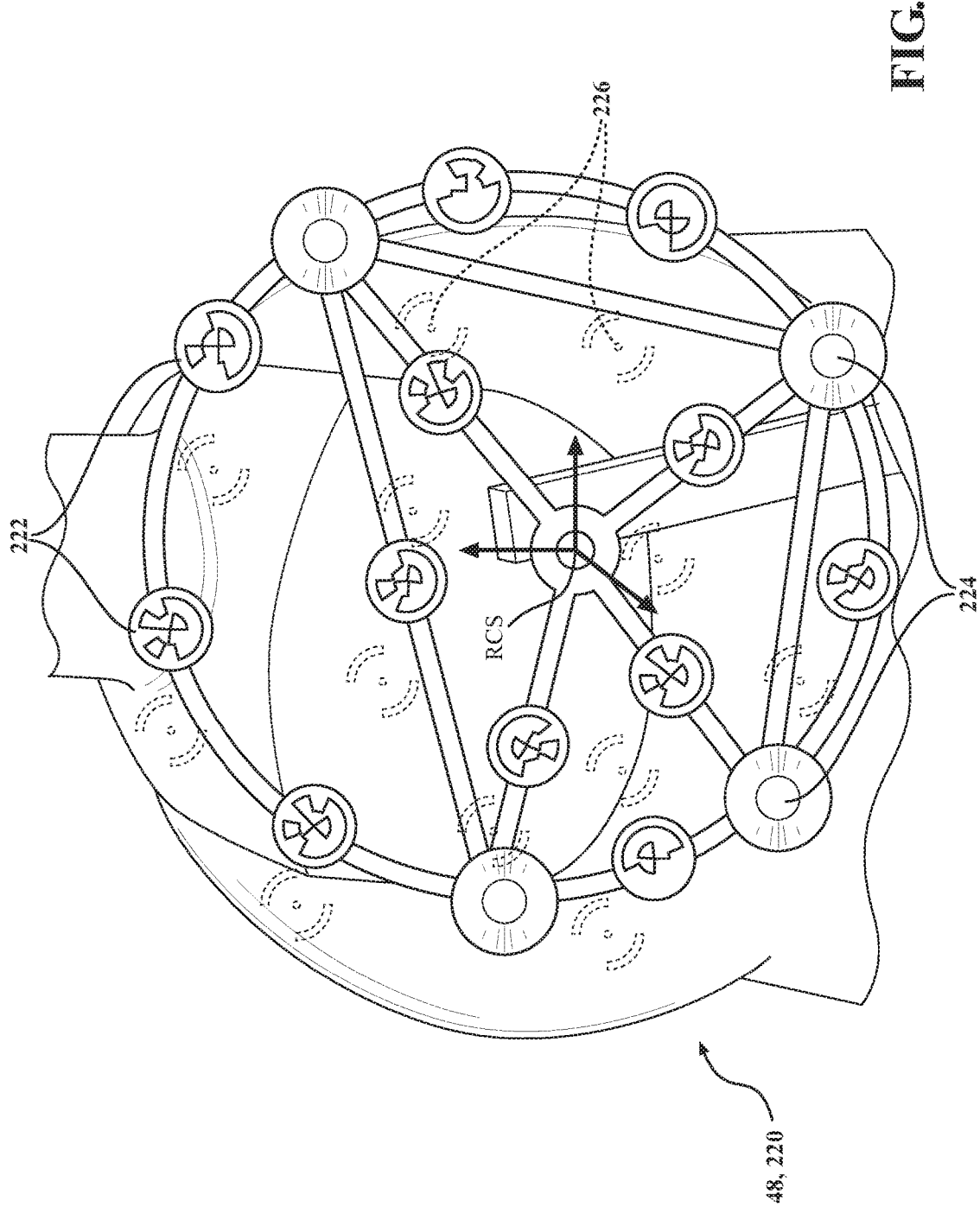
FIG. 4 is a perspective view of a registration device.

Referring to FIG. 4, in one embodiment, the HMD 200 can be registered with the localizer coordinate system LCLZ using a registration device 220. In this embodiment, the registration device 220 also acts as the base tracker 48 and is coupled to the surgical tool 22 by virtue of being mounted to the base 57. The registration device 220 has a registration coordinate system RCS. The registration device 220 comprises a plurality of registration markers 222 for being analyzed in the images captured by the camera 214 of the HMD 200 to determine a pose of the HMD coordinate system relative to the registration coordinate system RCS (or vice versa). The registration markers 222 can be printed markers having known, unique patterns for being recognized in the images captured by the camera 214 using pattern/object recognition techniques. The registration markers 222 may comprise planar reference images, coded AR markers, QR codes, bar codes, and the like. An image processing engine may identify the registration markers 222 and determine a corresponding position and/or orientation of the registration markers 222. Known software can be employed to analyze the images from the camera 214 on the HMD 200 to identify the registration markers 222 and determine coordinates of the registration markers in the HMD coordinate system, sometimes in conjunction with data from the depth sensor. Such software can include, for example, Vuforia, Vuforia SDK, VuMark, and/or Vuforia Model Targets, all provided by PTC Inc. of Needham, Mass.; open source software, such as the HololensARTookKit and/or the ARToolkit (v5.3.2); or other software. Additionally, image data from the camera 214 and/or data from the depth sensor can be analyzed to identify the registration markers 222 and to determine coordinates of the registration markers 222 in the HMD coordinate system in the manner described in U.S. Patent Application Pub. No. 2012/0306850, entitled, "Distributed Asynchronous Localization and Mapping for Augmented Reality," hereby incorporated herein by reference.

The patterns/objects associated with the registration markers 222 can be stored in memory in the HMD controller 210, the navigation controller 26, or elsewhere. The registration markers 222 may assume any form of marker that is capable of being identified in the images of the camera 214 for purposes of determining the coordinates of the registration markers 222 in the HMD coordinate system, either directly, or through the local coordinate system LOCAL of the HMD 200. In some cases, three or more unique registration markers 222 are provided. In the embodiment shown, twelve registration markers 222 are provided. The position and orientation of the camera 214 is known or determined in the HMD coordinate system such that the positions of the registration markers 222 can also be determined.

The registration device 220 further comprises a plurality of tracking markers 224 for being sensed by the one or more position sensors 40 of the localizer 34 to determine a pose of the registration coordinate system RCS relative to the localizer coordinate system LCLZ. The tracking markers 224 can be active or passive tracking markers like those previously described for the trackers 44, 46, 48.

The positions of the registration markers 222 are known with respect to positions of the tracking markers 224 in the registration coordinate system RCS. These relative positions can be measured during manufacture of the registration device 220, such as by a coordinate measuring machine (CMM) or can be determined using the pointer previously described. The positions (e.g., the coordinates) of the registration markers 222 and the tracking markers 224 in the registration coordinate system RCS can be stored in memory in the HMD controller 210, the navigation controller 26, or elsewhere for retrieval by any one or more of the controllers described herein.

At least one controller, such as the HMD controller 210, the navigation controller 26, and/or the manipulator controller 54 registers the HMD coordinate system and the localizer coordinate system LCLZ in response to the user directing the HMD 200 toward the registration markers 222 so that the registration markers 222 are within the field of view of the camera 214 and thus within the images captured by the camera 214 and in response to the one or more position sensors 40 sensing the tracking markers 224.

Capturing of the images by the camera 214 and sensing of light signals from the tracking markers 224 may occur simultaneously, but need not occur at the same time. The HMD 200 may capture the registration markers 222 and determine their position in the HMD coordinate system while moving. As long as the registration device 220 and the localizer 34 stay fixed, the localizer 34 can later find the tracking markers 224 at any time to complete registration. In one embodiment, after the HMD controller 210 is done getting data relating to the positions of the registration markers 222 in the HMD coordinate system, the next time that the localizer 34 sees the registration device 220, the localizer 34 sends the appropriate information to the navigation controller 26 to sync the HMD coordinate system and the localizer coordinate system LCLZ.

The HMD controller 210 may also instruct the image generator 206 to generate one or more indicator images 226 through the HMD 200 to the user that indicates to the user that registration is complete. The indicator images 226 may be holographic images (holograms) intended to be displayed to the user such that the indicator images 226 appear to be co-located with respective registration markers 222, i.e., they are world-locked in the manner described in the aforementioned patents incorporated herein by reference. The intent being that if the indicator images 226 do not appear to be co-located or in some readily apparent registration relationship (e.g., world-locked) to the registration markers 222, then registration is not complete or an error has occurred. In FIG. 4, the indicator images 226 are shown offset from the registration markers 222 and thus not aligned with or co-located with the registration markers 222—meaning that registration is not complete. The indicator images 226 may also change color to indicate that registration is complete. For instance, the indicator images 226 may be red/yellow until registration is complete, at which time the indicator images 226 change to green/blue to visually represent to the user that registration is complete. It should be appreciated that the term color comprises hue, tint, shade, tone, lightness, saturation, intensity, and/or brightness such that references made herein to different colors also encompasses different hue, tint, tone, lightness, saturation, intensity, and/or brightness. In addition, or alternatively, the HMD controller 210 may generate the indicator images 226 so that the indicator images 226 indicate to the user progress of registration. For example, the indicator images may start as red dots with arcuate bars arranged in a clock-like manner around the red dot with the arcuate bars being progressively filled as registration improves—similar to how a status bar shows the progress of computer downloads, etc.

Displaying of the indicator images 226 can be performed in the manner described in the following patents, all of which are hereby incorporated herein by reference: U.S. Pat. No. 9,256,987, entitled, "Tracking Head Movement When Wearing Mobile Device"; U.S. Pat. No. 9,430,038, entitled, "World-locked Display Quality Feedback"; U.S. Pat. No. 9,529,195, entitled, "See-through Computer Display Systems"; U.S. Pat. No. 9,348,141, entitled, "Low-latency Fusing of Virtual and Real Content"; U.S. Pat. No. 9,230,368, entitled "Hologram Anchoring and Dynamic Positioning"; and U.S. Pat. No. 8,472,120, entitled, "See-through Near-eye Display Glasses with a Small Scale Image Source."

Figure 5:
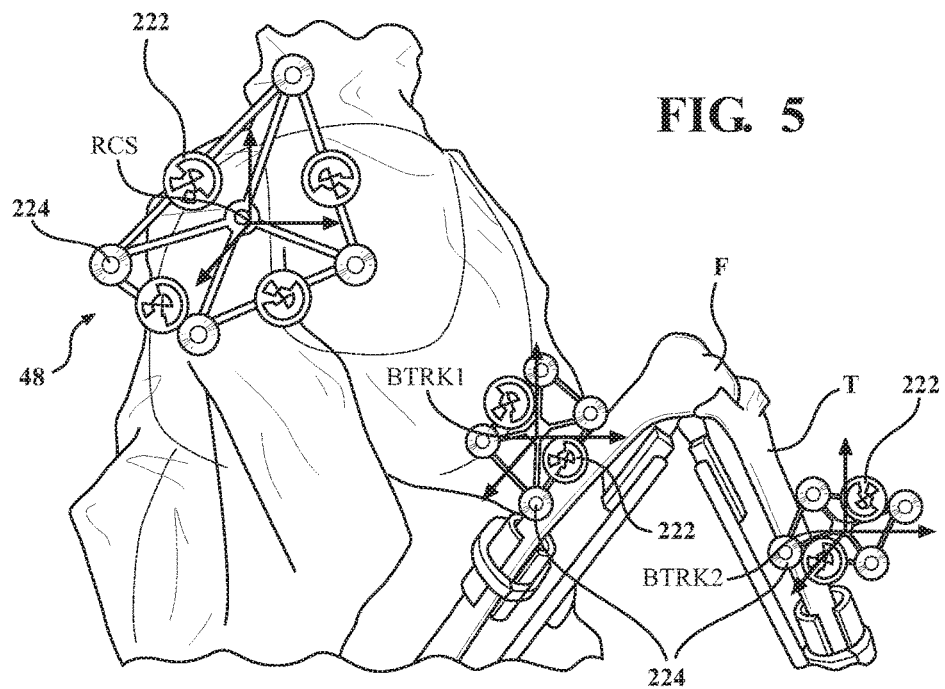
FIG. 5 is a perspective view of various trackers used as registration devices.

FIG. 5 illustrates the trackers 44, 46, 48 with registration markers 222 incorporated therewith to form separate registration devices. In this case, the trackers 44, 46, 48, comprise registration devices and can serve multiple purposes—namely to register the HMD coordinate system and the localizer coordinate system LCLZ, but also to continue tracking their associated objects, e.g., the femur, tibia, and base of the manipulator 12.

Referring back to FIG. 3, the HMD 200 locates the registration markers 222 on the registration device 220 in the HMD coordinate system via the camera 214 and/or depth sensor thereby allowing the HMD controller 210 to create a transform T7 from the registration coordinate system RCS to the HMD coordinate system, i.e., based on the HMD 200 being able to determine its own location (e.g., of the local coordinate system LOCAL) in the HMD coordinate system and vice versa. In one embodiment, the HMD 200 captures the registration markers 222 on the registration device 220 in images via the camera 214 and locates the registration markers 222 in the local coordinate system LOCAL that can be transformed to the HMD coordinate system. Various methods can be employed to determine the coordinates of the registration markers 222, including computer triangulation methods or reconstruction methods, photometric stereo methods, geometric modeling, 3D-scanning, structured light projection and imaging, and the like.

In one example, the HMD controller 210 builds rays from the camera 214 to each of the registration markers 222 as the HMD 200 moves around the room, i.e., the rays are built starting at 0, 0, 0 (or some other known location) in the local coordinate system LOCAL to each registration marker 222, but because of the movement around the room, multiple rays for each registration marker 222 are built at different orientations. The HMD controller 210 builds these rays in the local coordinate system LOCAL and transforms the rays to the HMD coordinate system where the HMD controller 210 finds the best fit (e.g., intersection) of the rays to determine the position of the registration markers 222 in the HMD coordinate system.

In another example, the camera 214 may comprise two stereo cameras that employ stereo vision to identify image pixels in sets of images that correspond with each of the registration markers 222 observed by the stereo cameras. A 3D position of the registration markers 222 (or points associated with the registration markers 222) is established by triangulation using a ray from each stereo camera. For instance, a point x in 3D space is projected onto respective image planes along a line which goes through each stereo camera's focal point, resulting in the two corresponding image points and since the geometry of the two stereo cameras in the LOCAL coordinate system (and the HMD coordinate system) is known, the two projection lines can be determined. Furthermore, since the two projection lines intersect at the point x, that intersection point can be determined in a straightforward way using basic linear algebra. The more corresponding pixels for each registration marker 222 identified, the more 3D points that can be determined with a single set of images. In some cases, multiple sets of images may be taken and correlated to determine the coordinates of the registration markers 222.

The HMD controller 210 must then determine where the localizer coordinate system LCLZ is with respect to the HMD coordinate system (transform T8) so that the HMD controller 210 can generate virtual images having a relationship (e.g., world-locked) to objects in the localizer coordinate system LCLZ or other coordinate system. A localizer transform T1 is determined from the registration coordinate system RCS to the localizer coordinate system LCLZ using knowledge of the positions of the tracking markers 224 in the registration coordinate system RCS and by calculating the positions of the tracking markers 224 in the localizer coordinate system LCLZ with the localizer 34/navigation controller 26 using the methods previously described. Transformation T8 from the HMD coordinate system to the localizer coordinate system LCLZ can then be calculated as a function of the two transforms T7, T1. In another variation, the transform T8 may be determined from the local coordinate system LOCAL to the localizer coordinate system LCLZ based on tracking the HMD tracker 218 and based on the known relationship between the HMD tracker coordinate system HMDTRK and the local coordinate system LOCAL (e.g., a known and fixed transform stored in memory) or the location of the HMD tracker 218 may be known and stored with respect to the local coordinate system LOCAL. In this case, the methods described herein may be accomplished without any need for the separate HMD coordinate system, i.e., the local coordinate system LOCAL can be considered as the HMD coordinate system.

During use, for example, the localizer 34 and/or the navigation controller 26 sends data on an object (e.g., the cut volume model) to the HMD 200 so that the HMD 200 knows where the object is in the HMD coordinate system and can display an appropriate image in the HMD coordinate system. In embodiments in which the femur cut volume is to be visualized by the HMD 200, the localizer 34 and/or navigation controller 26 needs three transforms to get the femur cut volume data to the localizer coordinate system LCLZ, T9 to transform the femur cut volume coordinate system MODEL1 to the femur coordinate system FBONE, T5 to transform the femur coordinate system FBONE to the bone tracker coordinate system BTRK1, and T6 to transform the bone tracker coordinate system BTRK1 to the localizer coordinate system LCLZ. Once registration is complete, then the HMD 200 can be used to effectively visualize computer-generated images in desired locations with respect to any objects in the operating room.

Figure 6:
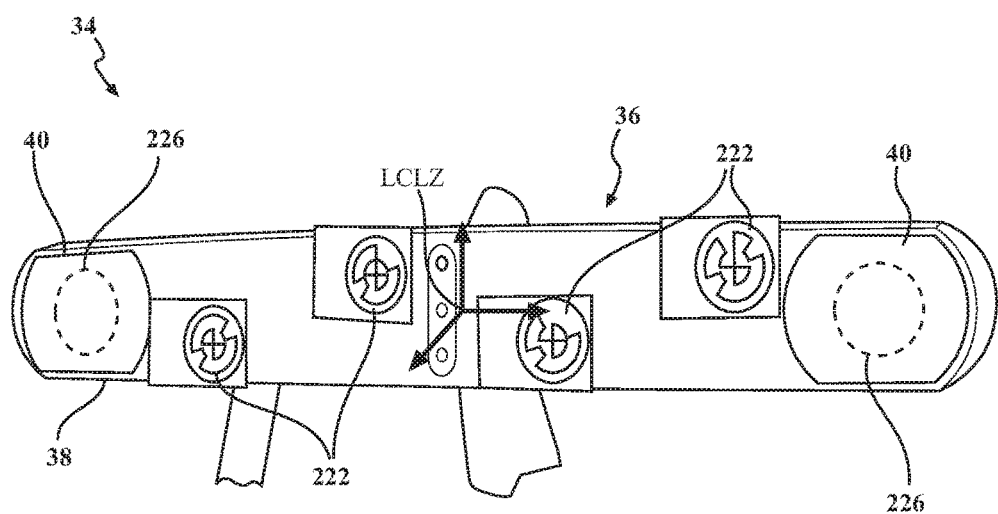
FIG. 6 is a perspective view of a camera unit.

Referring to FIG. 6, in another embodiment, a plurality of registration markers 222 are disposed on the housing 38 of the localizer 34 in known positions in the localizer coordinate system LCLZ. The registration markers 222 are configured to be analyzed in the images captured by the camera 214 of the HMD 200 in the same manner previously described to determine a pose of the localizer coordinate system LCLZ relative to the HMD coordinate system. In this case, the HMD controller 210 and/or other controller is configured to register the HMD coordinate system and the localizer coordinate system LCLZ in response to the user directing the HMD 200 toward the registration markers 222 so that the registration markers 222 are within the field of view of the camera 214 such that they are included in the images captured by the camera 214. Similar to the prior described embodiments, one or more indicator images 226 can be generated by the HMD controller 210 indicating to the user the progression of registration, registration errors, and/or when registration is complete. The indicator images 226 displayed by the HMD 200 in FIG. 6 show rings of dots that completely encircle the position sensors 40 with one of the rings being fully illuminated a first color while the remaining ring is only faintly illuminated indicating that registration is not yet complete.

Figure 7:
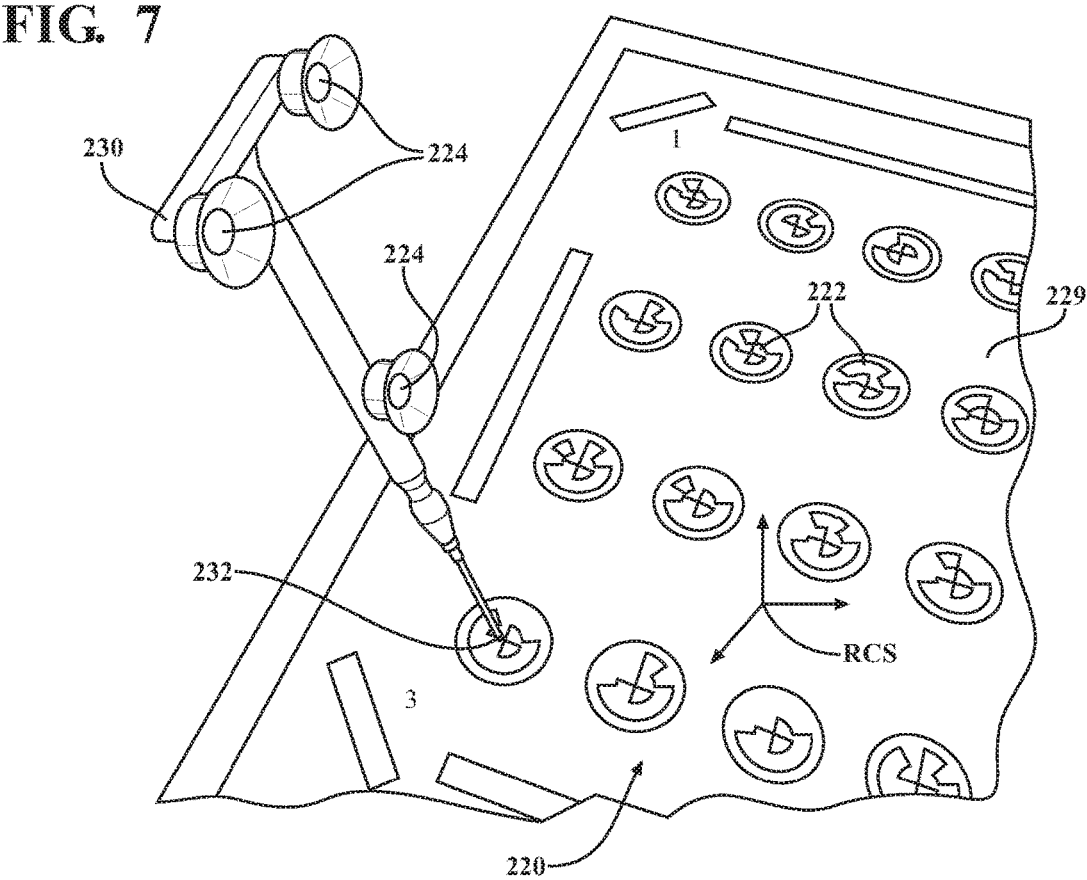
FIG. 7 is a perspective view of another registration device.

Referring to FIG. 7, in another embodiment, the registration device 220 is in the form of a substrate 229 comprising a plurality of registration markers 222 for being analyzed in the images captured by the camera 214 of the HMD 200 to determine a pose of the registration coordinate system RCS relative to the HMD coordinate system. In this embodiment, a registration probe 230 is used for registration. The registration probe 230 may be like the pointer previously described. The registration probe 230 has a registration tip 232 and a plurality of tracking markers 224 for being sensed by the one or more position sensors 40 of the localizer 34 to determine a position of the registration tip 232 in the localizer coordinate system LCLZ. The registration tip 232 is in a known position with respect to the tracking markers 224 with this known data being stored in the memory of the navigation controller 26 and/or the HMD controller 210.

A pose of the registration coordinate system RCS with respect to the localizer coordinate system LCLZ is determined upon placing the registration tip 232 in a known location with respect to each of the registration markers 222 and simultaneously sensing the tracking markers 224 with the one or more position sensors 40. In this case, the known location with respect to each of the registration markers 222 is a center of the registration markers 222. In one embodiment, at least three registration markers 222 are touched by the registration tip 232 before registration can be completed.

The HMD controller 210 is configured to register the HMD coordinate system and the localizer coordinate system LCLZ in response to the user directing the HMD 200 toward the registration markers 222 so that the registration markers 222 are within the field of view of the camera 214 and thus in the images captured by the camera 214 and in response to the one or more position sensors 40 sensing the tracking markers 224 when the registration tip 232 is placed in the known locations with respect to each of the registration markers 222. A foot pedal, a button on the registration probe 230, or other device that communicates with the localizer 34, may be used to trigger light emission from the localizer 34 to the tracking markers 224 on the registration probe 230 with the light then being reflected and detected by the position sensors 40. Alternatively, the tracking markers 224 may be active markers that transmit light signals directly to the position sensors 40. Of course, other navigation and tracking modalities, may be employed as previously described. Similar to the prior described embodiments, one or more indicator images 226 can be generated by the HMD controller 210 indicating to the user the progression of registration, registration errors, and/or when registration is complete.

The HMD controller 210 may also be configured to generate a probe image (not shown) through the HMD 200 that is associated with the registration probe 230. The probe image may be a holographic or other type of image overlaid onto the real registration probe 230 during registration to indicate to the user the accuracy of registration. The probe image may be configured to be congruent with the registration probe 230 or at least portions of the registration probe 230 so that the accuracy of registration can be indicated visually based on how well the probe image is overlaid onto the real registration probe 230. For instance, if the probe image appears at an orientation different than the real registration probe 230, there may be an error. Similarly, if the probe image appears to be in the same orientation, but offset or spaced from the real registration probe 230, an error is also immediately apparent.

Figure 8:
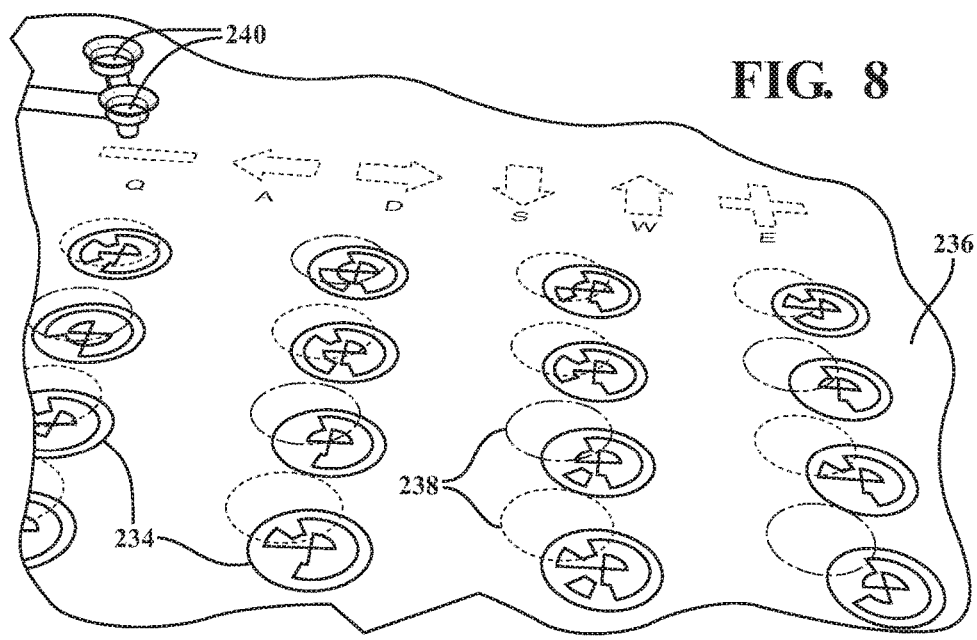
FIG. 8 is an illustration showing calibration using virtual images displayed by a head-mounted display (HMD).

Referring to FIG. 8, in some embodiments, once registration of the HMD coordinate system and the localizer coordinate system LCLZ is complete, fine tuning of the registration can be conducted to adjust the accuracy of the registration. This calibration can be performed using calibration markers 234 located on a substrate 236. The calibration markers 234 can be similar to the registration markers 222 previously described, e.g., printed unique patterns, coded patterns, etc. Current error with registration can be indicated to the user using a plurality of virtual calibration marker images 238 displayed to the user via the HMD 200, wherein the virtual calibration marker images 238 have a congruency with the real calibration markers 234 so that the virtual calibration marker images 238 are capable of being aligned with the real calibration markers 234 and a magnitude of misalignment is indicative of the registration error.

Other manners of visually indicating the registration error are also contemplated, e.g., by viewing the location of real and virtual images of centers of the calibration markers 234, etc.

Once the user visually recognizes the registration error, the user can then fine tune or calibrate the registration of the HMD coordinate system and the localizer coordinate system LCLZ to reduce the registration error. In one embodiment, the user provides input, such as through an input device (e.g., keyboard, mouse, touchscreen, foot pedal, etc.) to the HMD controller 210 that essentially adjusts the positions of the virtual calibration marker images 238 relative to the real calibration markers 234 to better align the virtual calibration marker images 238 with the real calibration markers 234 so that the virtual calibration marker images 238 coincide with the real calibration markers 234. This can be accomplished by simply altering the coordinates of the virtual calibration marker images 238 in the localizer coordinate system LCLZ by incremental amounts in any one or more of three directions corresponding to x, y, and/or z-axes of the localizer coordinate system LCLZ. The closer the virtual calibration marker images 238 overlap/coincide with the real calibration markers 234, the greater the registration accuracy. As shown in FIG. 8, the HMD 200 can also provide instructional images 240 at the same time as displaying the virtual calibration marker images 238 to instruct the user as to how calibration can be performed, including images showing which keys to press on the keyboard to shift left, shift right, shift up, shift down, shift in, and shift out. Rotational shifts could also be applied. Once aligned, the associated transformation from the HMD coordinate system to the localizer coordinate system LCLZ (or vice versa) can be updated.

Figure 9:
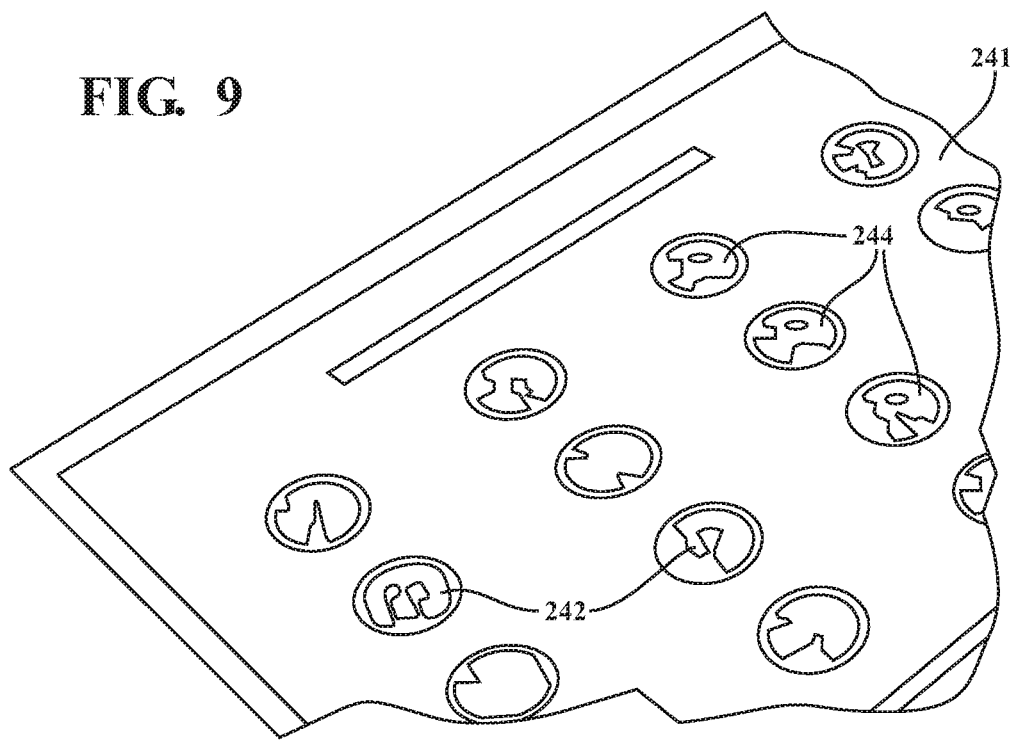
FIG. 9 is an illustration showing one method of depicting registration accuracy using virtual images displayed by the HMD.

Referring to FIG. 9, the registration error in registration of the HMD coordinate system and the localizer coordinate system LCLZ can be determined and visually displayed. In this case, the HMD coordinate system and the localizer coordinate system LCLZ have already been registered. Accordingly, the HMD 200 and the localizer 34 are able to operate in a common coordinate system. Thus, registration errors can be identified by determining how closely positions in the common coordinate system determined by the HMD 200 correlate to positions in the common coordinate system determined by the localizer 34. In the embodiment shown, a substrate 241 with error-checking markers 242 is used to determine the registration error.

The HMD controller 210 determines HMD-based positions of the plurality of error-checking markers 242 in the common coordinate system (e.g., the localizer coordinate system LCLZ or other common coordinate system) by analyzing images captured by the camera 214 of the HMD 200. For instance, the HMD-based positions may be centers of the error-checking markers 242. At the same time, the localizer 34 and/or navigation controller 26 can also determine localizer-based positions of the plurality of error-checking markers in the common coordinate system by placing a tip (e.g., the registration tip 232) of a navigation probe (e.g., the registration probe 230) in a known location with respect to each of the error-checking markers 242 (e.g., at their center, etc.) and simultaneously sensing the tracking markers 224 of the navigation probe with one or more of the position sensors 40 of the localizer 40. See, for example, FIG. 7. These positions can be captured using the foot pedal, button on the probe, etc. as previously described. The HMD-based positions can then be compared to the localizer-based positions of each of the error-checking markers 242. Ideally, the HMD-based positions and the localizer-based positions of each of the error-checking markers 242, e.g., the positions of their centers, are identical—meaning that there is perfect registration. If they are not identical, then there is some error in the registration. The differences in magnitude and direction of the corresponding position indicates the registration error for each of the error-checking markers 242.

Indicator images 244 can be provided through the HMD 200 to indicate to the user the registration error for each of the error-checking markers 242. In the embodiment shown in FIG. 9, the indicator images 244 are indicator markers or dots that, if there was perfect registration, would be located directly in the center of each of the error-checking markers 242. Instead, owing to some error in registration, some of these indicator images 244 are off-center. The amount of registration error correlates directly to how far off-center the indicator images 244 are shown relative to the real error-checking markers 242. Other visual methods of indicating the registration error are also contemplated such as simple visually indicating bars that represent the magnitude of error with respect to each of the error-checking markers 242 or providing numerical values of the registration error with respect to each of the error-checking markers 242.

Figure 10:
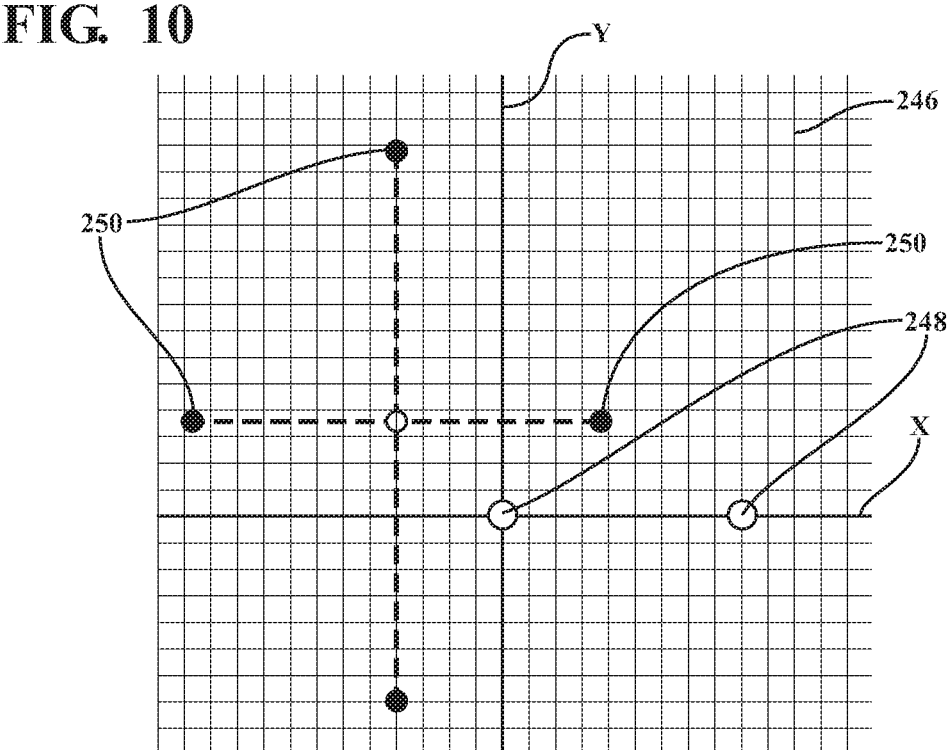
FIG. 10 is an illustration showing another method of depicting registration accuracy using virtual images displayed by the HMD.

Referring to FIG. 10, registration accuracy between the HMD coordinate system and the localizer coordinate system LCLZ can be visually shown to the user via a substrate 246 having graduated markings in two directions, i.e., along X and Y axes. In the embodiment shown, the substrate 246 comprises conventional graph paper. A pair of error-checking markers in the form of divots 248 are fixed to the substrate 246 to receive the tip (e.g., the registration tip 232) of the navigation probe (e.g., the registration probe 230). One of the divots 248 is located at an origin of the X, Y axes and the other divot 248 is spaced from the origin along the X axis, for instance, to establish the X axis. The positions of the divots 248 are determined by the localizer 34 and/or the navigation controller 26 in the common coordinate system using the navigation pointer in the manner previously described. These positions establish the X, Y axes on the substrate 246.

The HMD controller 210 then receives these positions from the localizer 34 and/or the navigation controller 26 indicating the location of the X, Y axes, and consequently the HMD controller 210 displays indicator images 250 through the HMD 200 to the user. The indicator images 250 comprise virtual X, Y axes in the embodiment shown, as well as the origin of the X, Y coordinates and end points of the X, Y axes. The HMD controller 210 generates the indicator images 250 so that they appear to the user to be at the same coordinates as determined by the localizer 34 and/or the navigation controller 26. The indicator images 250 are expected to be visualized as though they overlap/align with the actual X, Y axes on the substrate 246. If the indicator images 250 do not coincide with the actual X, Y axes, the difference in distance between the virtual and actual X, Y axes indicates to the user the registration error. Because the substrate 246 comprises a visible error scale via the graduated markings, and the indicator images 250 are displayed with respect to the visible error scale, the user can manually determine the magnitude of the registration error. Other types of indicator images 250 are also possible, including dots, gridlines to help see the error, and the like.

The HMD 200 can be used to assist in registering the manipulator coordinate system MNPL and the localizer coordinate system LCLZ (see transforms T1-T3 and T12 on FIG. 3) by guiding the user in how to move the surgical tool 22 during registration. The navigation system 20 provides an initial registration using the base tracker 48 and a separate tool tracker 252 removably coupled to the surgical tool 22 (see coordinate system TLTK in FIG. 3).

Figure 11:
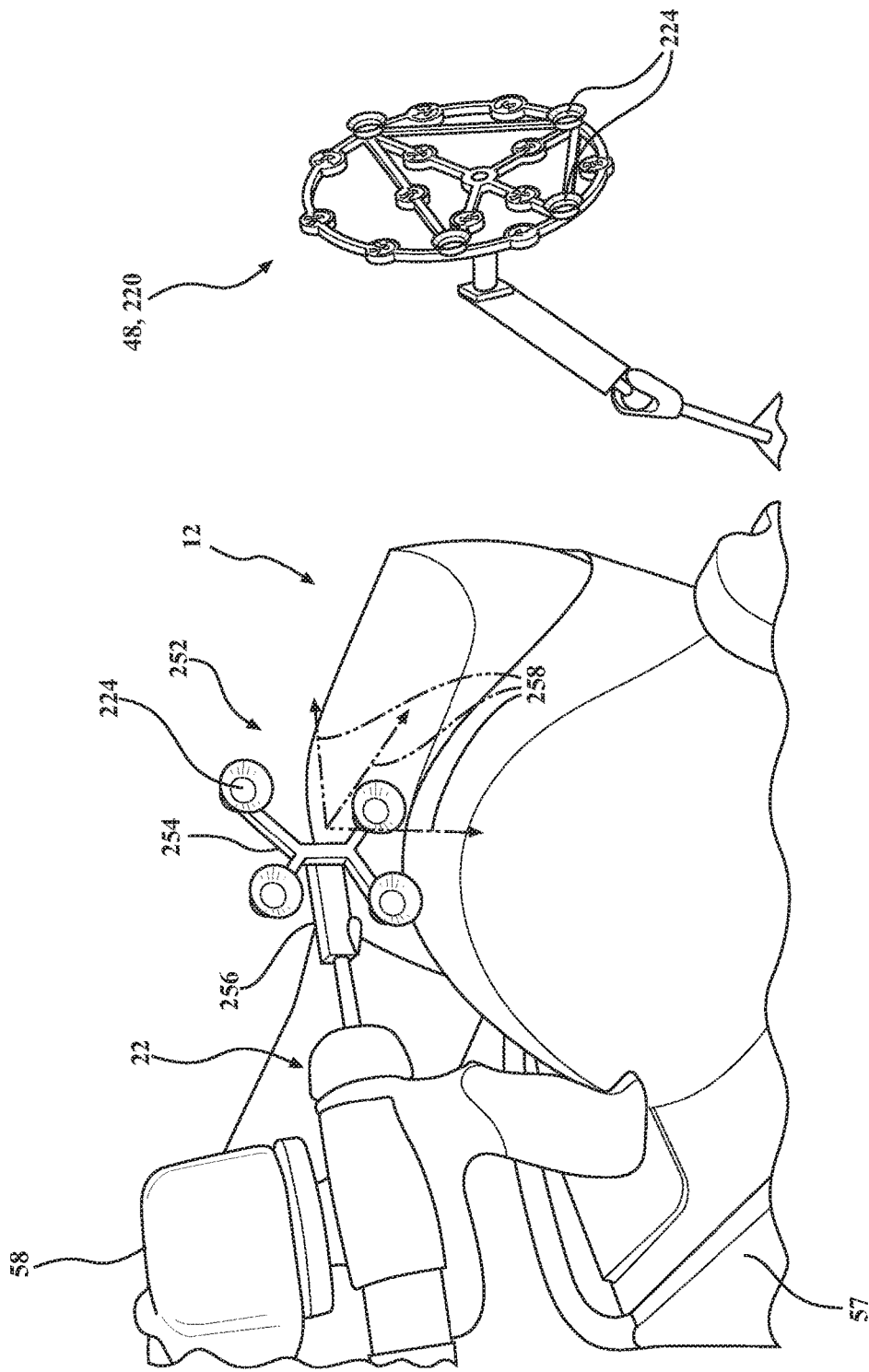
FIG. 11 is a perspective view of a manipulator and surgical tool showing one method of depicting a registration protocol to finalize registration using virtual images displayed by the HMD.

Referring to FIG. 11, the tool tracker 252 has a plurality of tracking markers 224 (four shown) mounted to a coupling body 256. The coupling body 256 is dimensioned to slide over the working end of the surgical tool 22 and surround a shaft of the surgical tool 22 in a relatively close fit so that the coupling body 256 is not loose. In the embodiment shown, the coupling body 256 has a passage into which the working end of the surgical tool 22 is received until the working end abuts a stop 254 on the tool tracker 252. Once the stop 254 has been reached, the tool tracker 252 can be secured to the surgical tool 22 by set screws or other clamping devices to hold the tool tracker 252 in place relative to the surgical tool 22.

The stop 254 of the tool tracker 252 is in a known position relative to the tracking markers 224 with this relationship being stored or input into the navigation controller 26 and/or manipulator controller 54. Owing to this known relationship, when the working end of the surgical tool 22 contacts the stop 254, then the working end of the surgical tool 22 is also in a known position relative to the tracking markers 224, and thus known in the tool tracker coordinate system TLTK. In the embodiment shown, since the working end comprises a spherical bur, only the location of the tool center point (TCP) of the bur, and possibly an axis of the shaft, needs to be determined in both coordinate systems—meaning that the rotational positions of bur and/or tool tracker 252 do not need to be fixed relative to one another for registration. However, for other energy applicators having more complex geometries, position and orientation of the energy applicator may need to be determined, e.g., the energy applicator coordinate system EAPP and the tool tracker coordinate system TLTK will be registered to each other.

With the base tracker 48 secured in position on the base of the manipulator 12 so that the base tracker 48 is fixed relative to the base, and thus fixed relative to the manipulator coordinate system MNPL, the initial registration is performed by determining the position of the tracking markers 224 on the base tracker 48 and determining the position of the tracking markers 224 on the tool tracker 252 (four shown). This provides an initial relationship between the localizer 34 (localizer coordinate system LCLZ) and the working end of the surgical tool 22 (energy applicator coordinate system EAPP). By utilizing the encoder-based data, an initial relationship between the localizer 34 and the manipulator 12 can also be established by the navigation controller 26 and/or manipulator controller 54 (see transform T3 on FIG. 3). However, to improve the registration, the user is requested to move the surgical tool 22 and its working end through a predefined pattern of movement so that multiple positions of the energy applicator coordinate system EAPP are captured to provide a more accurate position thereof.

The HMD 200 is used to instruct the user how to move the surgical tool 22. In particular, in one embodiment, the HMD controller 210 generates protocol images 258 with the HMD 200 that define a registration protocol for the user to follow to continue registration of the manipulator coordinate system MNPL and the localizer coordinate system LCLZ. The registration protocol comprises movement indicators to indicate to the user movements to be made with the surgical tool 22 while the tool tracker 252 is temporarily mounted to the surgical tool 22.

The protocol images 258 shown in FIG. 11 comprise a movement indicator in the form of an arrow that shows the user which direction to move the surgical tool 22 during registration, an orientation indicator in the form of an arrow that shows the user the orientation of the tool tracker 252 to maintain during the movement, and a line-of-sight indicator in the form of an arrow configured to be pointed toward the localizer 34 so that the user maintains line-of-sight between the tracking markers 224 and the localizer 34. So, for instance, one arrow may indicate the direction to move the surgical tool 22, another arrow may indicate, along with the first arrow, a plane in which to keep the tool tracker 252, and the third arrow may show the user which direction to face the tool tracker 252 to maintain line-of-sight. The protocol images may also comprises other graphical or textual instructions for the user. Once the user has performed the necessary movements, registration is finalized by determining a position of the energy applicator coordinate system EAPP out of the numerous positions collected, e.g., by averaging the positions, weighted averaging, etc. In some embodiments, the manipulator 12 may be configured to activate one or more of the joint motors to generate haptic feedback to the user through the surgical tool 22 in response to the user moving the surgical tool 22 in an incorrect direction with respect to the movement indicator, orientation indicator, and/or line-of-sight indicator.

Figure 12:
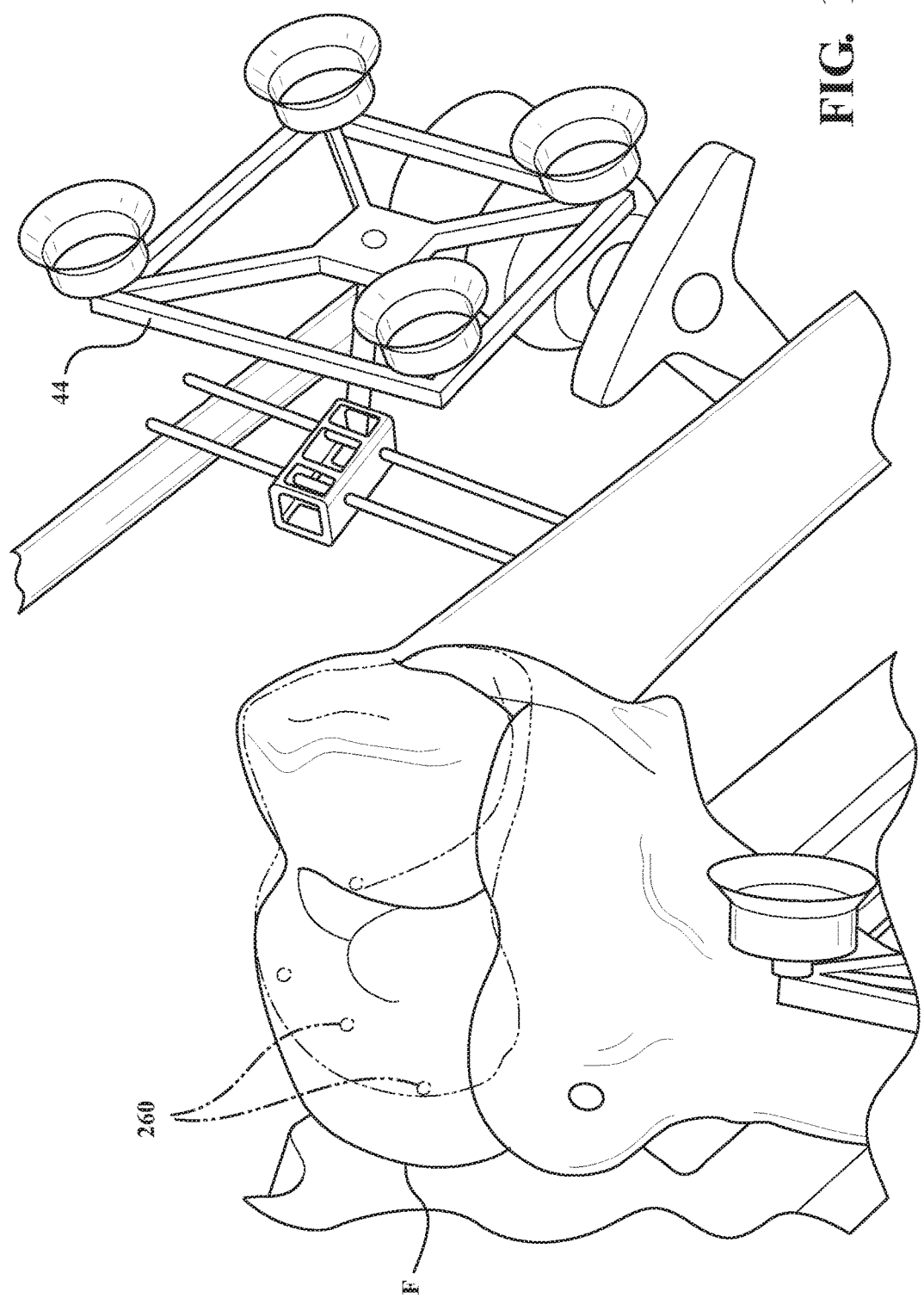
FIG. 12 is a perspective view of a femur showing one method of verifying registration using virtual images displayed by the HMD.

Referring to FIG. 12, the HMD 200 may be used to assist with registration of the three-dimensional model (model coordinate system MODEL2 in FIG. 3) of the patient's anatomy to the associated bone tracker 44 (bone tracker coordinate system BTRK1) via the associated registration of the actual bone (bone coordinate system FBONE) to the bone tracker 44, e.g., see transforms T5, T11 in FIG. 3. The three-dimensional model of the patient's anatomy is a virtual model that may be derived from pre-operative images as previously described, bone tracing methods, and the like. Registration may be carried out using the registration probe 230 described above. In this case, registration comprises instructing the user to place the tip 232 of the registration probe 230 at various landmarks on the bone, e.g., the femur F, and then collect the position of the tip 232 by foot pedal, button on the probe, etc. When enough points are collected, the navigation system 20 is able to fit the three-dimensional model of the bone to the actual bone using best fit methods based on the collected points. During registration, the HMD 200 can provide instructions to the user about which points to collect, show the user where on typical anatomy the points might be located, etc.

The HMD 200 may also be used to verify the accuracy of the registration of the three-dimensional model and actual bone to the bone tracker 44. During such registration verification, landmark images 260 are generated by the HMD controller 210 and shown to the user through the HMD 200. These landmark images 260 define a verification protocol for the user to follow to verify the registration of the model coordinate system MODEL2 and the localizer coordinate system LCLZ. The landmark images 260 depict virtual landmarks associated with the virtual three-dimensional model of the patient's bone. The landmark images 260 are displayed to the user with the HMD 200 as being overlaid on the patient's bone such that the user is able to verify registration by placing the tip 232 of the registration probe 230 (also referred to as a navigation probe) on the patient's bone while positioning the tip 232 of the registration probe 230 in desired positions relative to the user's visualization of the landmark images 260, i.e., by seemingly touching the landmark images 260 with the tip 232. By placing the landmark images 260 so that they appear on the patient's bone, an initial visual indication of the accuracy of the registration can be determined—if the landmark images 260 don't appear to be on the bone's surface, the registration is likely poor.

Figure 13:
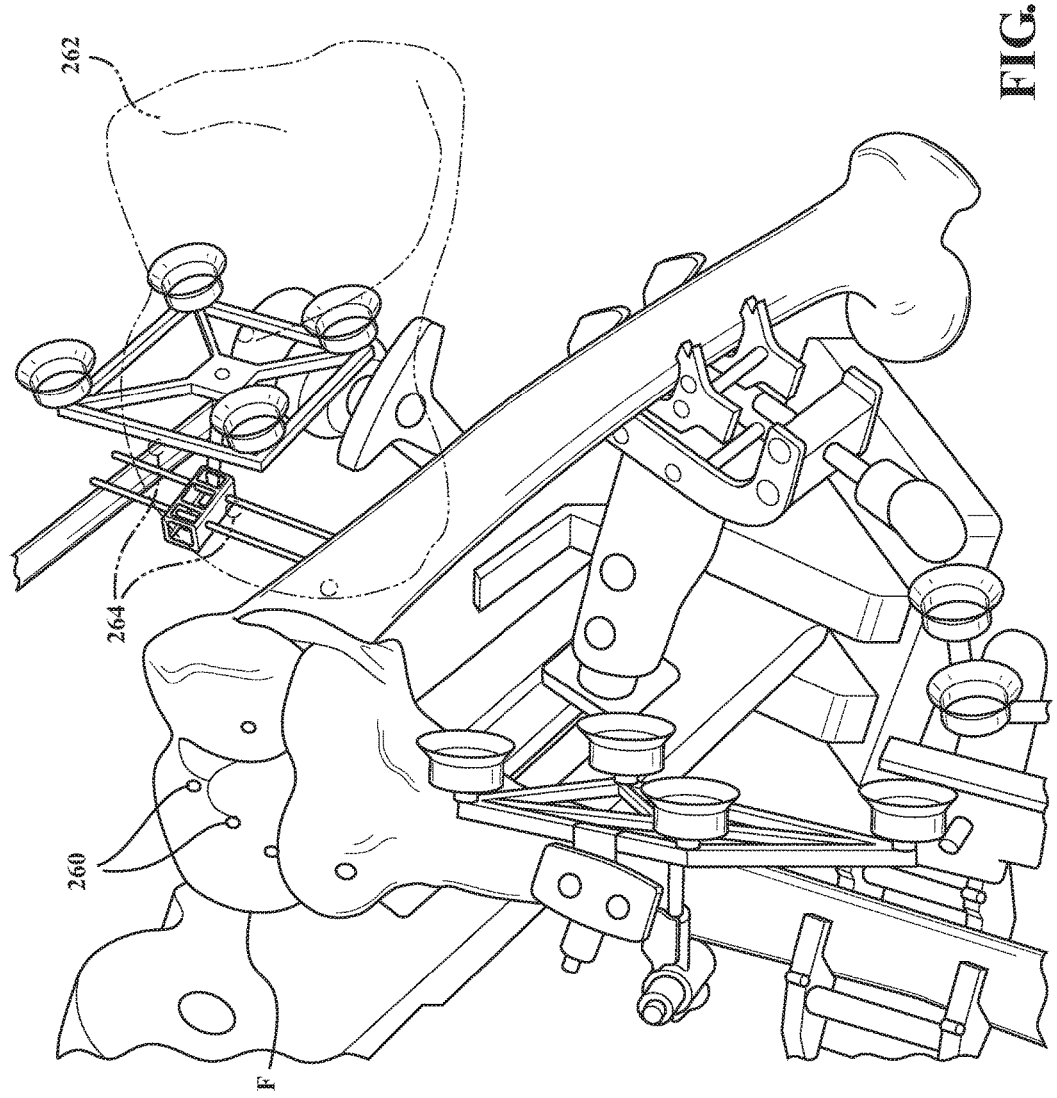
FIG. 13 is a perspective view of a femur and model image showing another method of verifying registration using virtual images displayed by the HMD.

Referring to FIG. 13, in another embodiment, a model image 262 may be generated with the HMD controller 210 to be displayed with the HMD 200 that represents all or at least a portion of the virtual model of the patient's bone. The model image 262 may be displayed so that it appears magnified and/or offset relative to the actual bone of the patient. The model image 262 may also be displayed, even if offset, to be in the same orientation as the actual bone (e.g., axes aligned). The model image 262 may be the same size as the actual bone or larger/smaller, in the same or different orientation, and/or aligned or offset from the actual bone. In this case, the model image 262 is shown offset. Additional offset landmark images 264 are displayed to the user with the HMD 200 in an offset and magnified manner with respect to the patient's bone and the other landmark images 260 placed on the actual bone. The user is able to verify registration by placing the tip 232 of the registration probe 230 on the patient's actual bone to seemingly touch the landmark images 260 while simultaneously visualizing an image (not shown) of the tip 232 of the registration probe 230 relative to the additional offset landmark images 264. Said differently, even though the actual tip 232 would be placed on the actual bone to touch off on the landmark images 260 seemingly located on the actual bone, an image representing the tip 232 of the registration probe 230 would appear adjacent to the model image 262 in the same relative position and/or orientation to provide an adjacent display for the user—but possibly magnified to provide an advantage to the user in selecting the landmark images required to verify registration. The offset landmark images 264 can be displayed in a 1:1 scale with the model image 262 so that the offset landmark images 264 adjust in size with the size of the model image 262.

Figure 14:
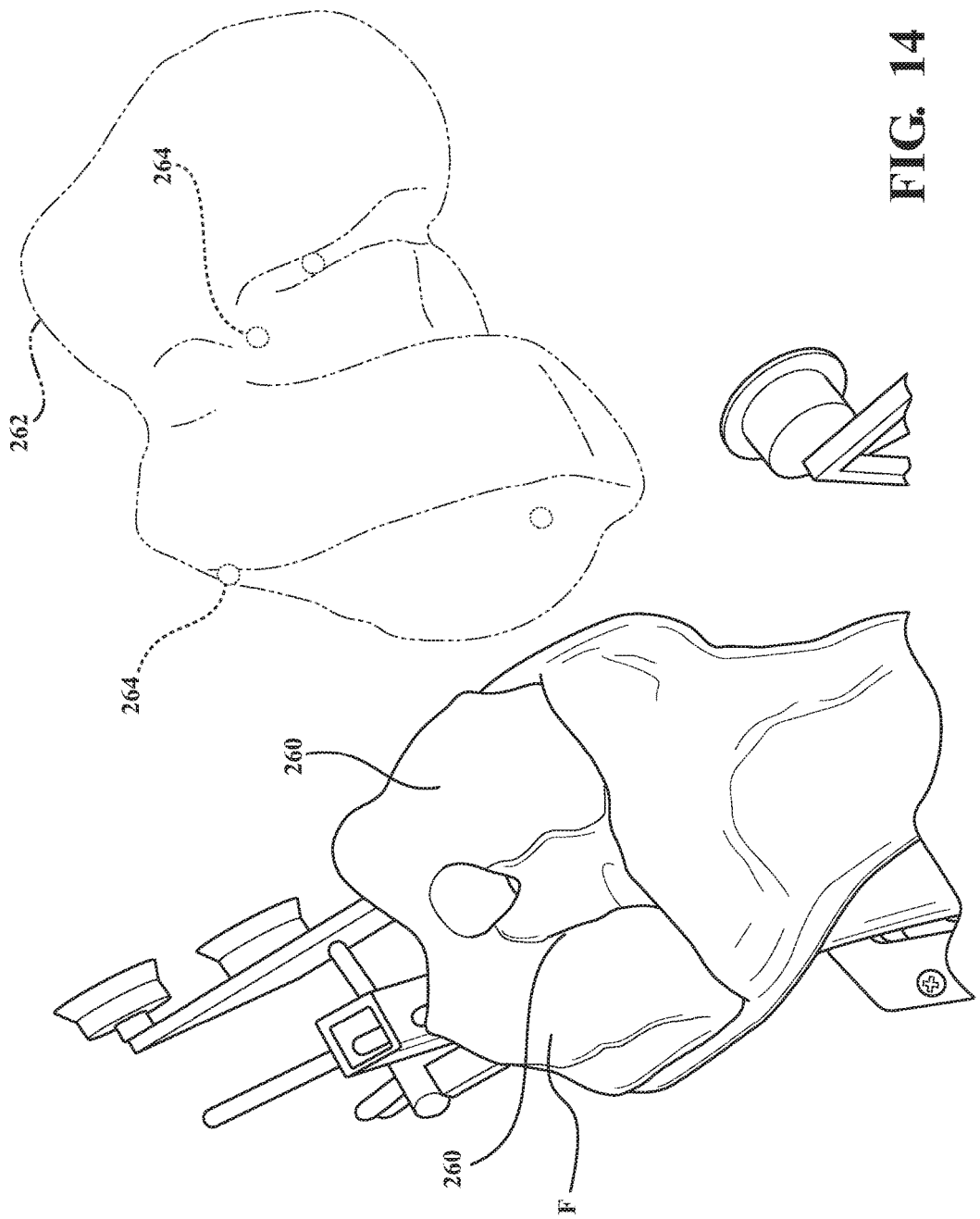
FIG. 14 is a perspective view of a femur and model image showing the method of FIG. 13 from a different angle.

Referring to FIG. 14, the landmark images 260 can be displayed to the user with the HMD 200 in an overlaid manner with respect to the patient's bone such that the user is able to verify registration by placing the tip 232 of the registration probe 230 on the patient's bone adjacent to each of the landmark images 260 and capturing points on the patient's bone adjacent to each of the landmark images 260 to determine if the points on the patient's bone are within a predetermined tolerance to the virtual landmarks associated with the three-dimensional bone model. Additionally, the model image 262 and the offset landmark images 264 are displayed to the user with the HMD 200 with respect to the patient's bone such that the model image 262 has a predefined transparency with respect to the offset landmark images 264 to avoid occluding the user's view of the offset landmark images 264, i.e., the user is able to see the offset landmark images 264 even though spatially they may be located behind the model image 262.

Figure 15:
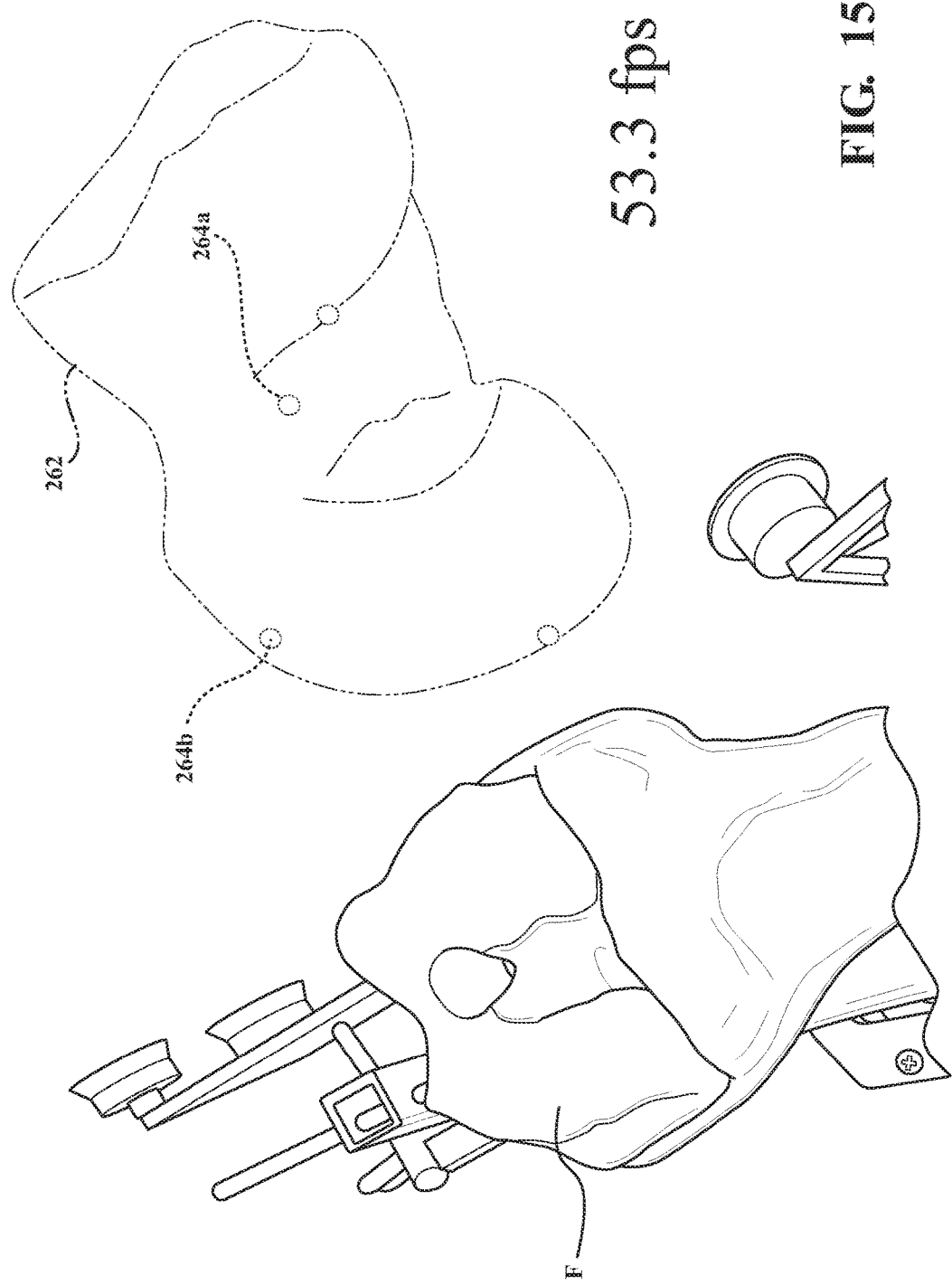
FIG. 15 is a perspective view of a femur and model image showing another method of verifying registration using virtual images displayed by the HMD.
Figure 16:
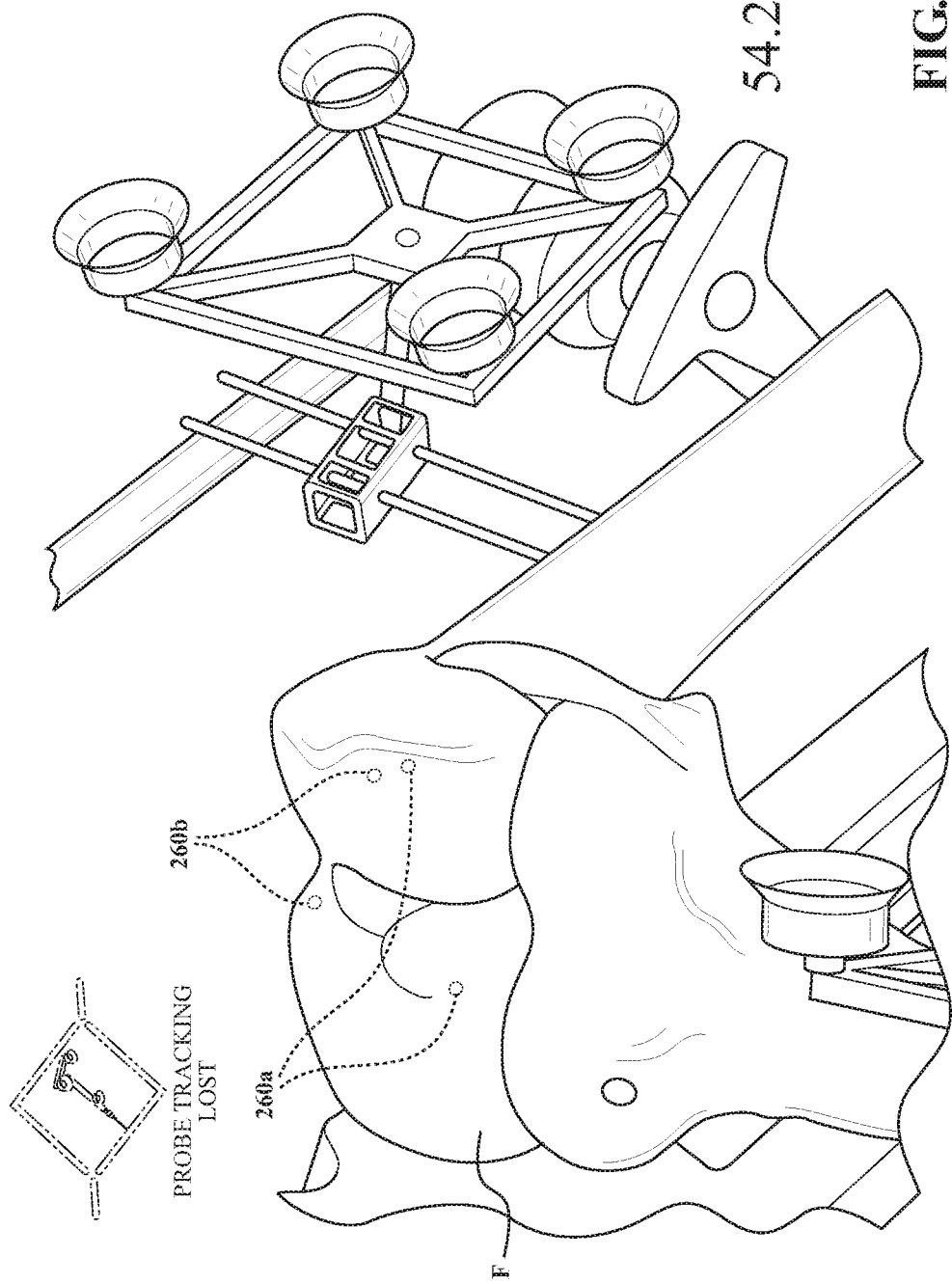
FIG. 16 is a perspective view of a femur showing another method of verifying registration using virtual images displayed by the HMD.
Figure 17:
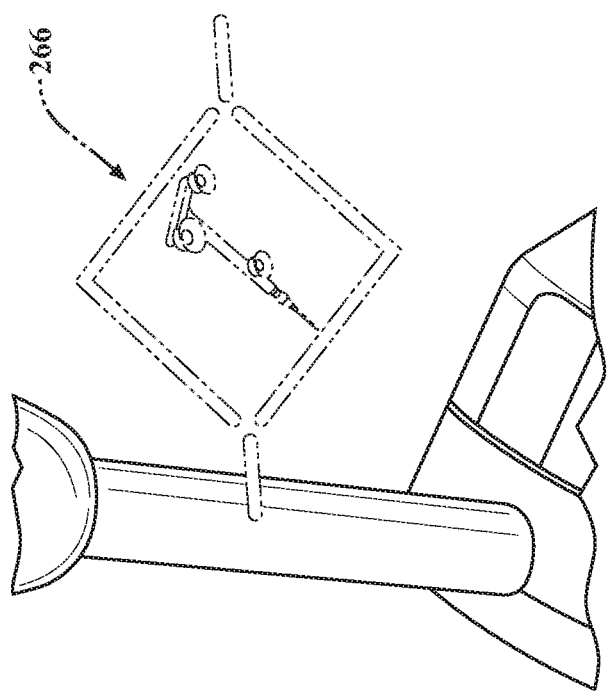
FIG. 17 is an illustration of a warning image displayed by the HMD.

FIG. 15 shows the model image 262 in a different orientation than the actual bone. FIG. 16 shows landmark images 260a, 260b on the actual bone without a separate model image adjacent to the actual bone where the landmark images 260a, 260b include landmark images 260a that represent virtual landmarks that have been miscaptured as described below (e.g., large error) and landmark images 260b that are uncaptured. FIG. 17 is an illustration of a warning image 266 generated by the HMD controller 210 and displayed through the HMD 200 to the user to indicate when the tracking markers 224 on the registration probe 230 may be blocked.

Additionally, or alternatively, the landmark images 260 and the offset landmark images 264 may be displayed in varying colors, intensities, etc., based upon location of the virtual landmarks on the virtual model of the patient's bone relative to the user's viewing angle. In other words, for instance, if the virtual landmarks are on a side of the virtual model away from the user such that they would not be seen to the user otherwise, the HMD controller 210 may cause those particularly landmark images to be colored differently, e.g., darker shade (see image 264a), while those that are visible are colored a lighter shade (see image 264b). This differentiation indicates to the user that, for instance, the darker shade offset landmark image 264a cannot be touched with the tip 232 of the probe 230 on the visible side of the actual bone, but instead the user will need to move the other side of the actual bone to touch on those obstructed points. One benefit of providing some type of visual differentiation among the landmark images 260, 264 based on whether they are in the user's line-of-sight, is that the user still visually recognizes that there are other landmark images to be virtually touched with the tip 232, but that they are inaccessible from the same vantage point.

Figure 18:
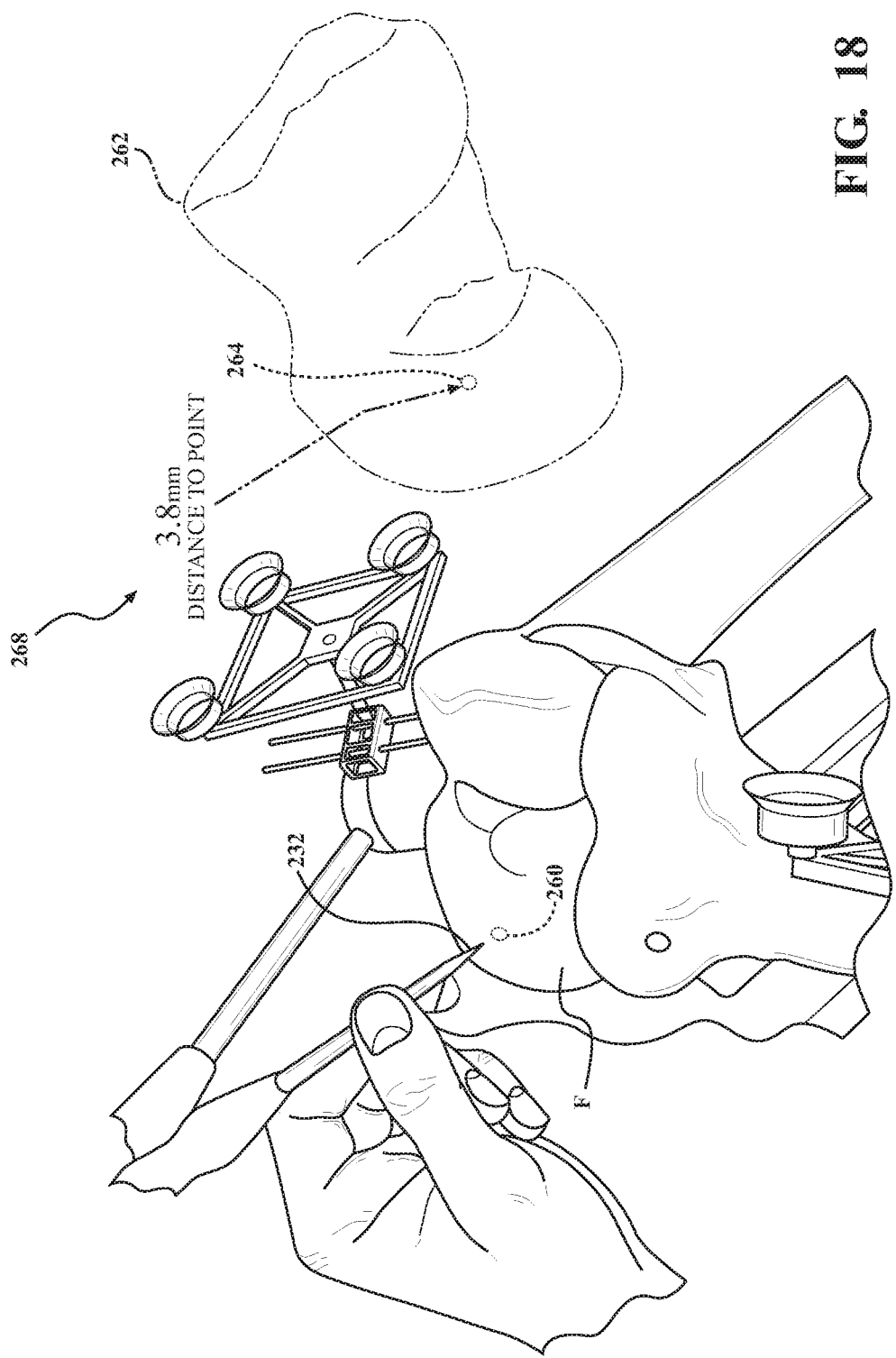
FIG. 18 is a perspective view of a femur and model image showing another method of verifying registration using virtual images displayed by the HMD.

Referring to FIG. 18, in another embodiment, display of the offset landmark images 264 to the user is based on distances of the tip 232 of the registration probe 230 relative to the virtual landmarks. For instance, the virtual landmark closest to the tip 232 of the registration probe 230 is depicted to the user on the offset model image 262 in a manner that distinguishes it relative to the remaining virtual landmarks. In the example shown, the offset landmark image 264 associated with the virtual landmark (and associated landmark image 260) closest to the tip 232 may be the only offset landmark image 264 displayed, while the remaining offset landmark images 264 depicting the remaining virtual landmarks are not displayed.

The HMD 200 may also display an image 268 showing in text or graphics the distance from the tip 232 to the closest virtual landmark. In some cases, all of the offset landmark images 264 may be visible through the HMD 200 until the user places the tip 232 within a predefined distance of one of the virtual landmarks, at which time the remaining offset landmark images 264 gradually fade away. Once the virtual landmark is collected by the registration probe 232 by placing the tip 232 on the landmark image 260 on the actual bone and actuating the foot pedal, button on the probe, etc., the remaining offset landmark images 264 may reappear until the tip 232 is placed within the predefined distance of another one of the virtual landmarks.

The landmark images 260 on the actual bone may behave like the offset landmark images 264 and fade/disappear/reappear similarly to the offset landmark images 264 during collection, etc. In other embodiments, only the offset landmark images 264 fade, disappear, and/or reappear, while the landmark images 260 associated with the actual bone are continuously displayed through the HMD 200.

Referring to FIG. 19, the navigation controller 26 and/or manipulator controller 54 may determine a status of each of the virtual landmarks based on whether they have been captured during the verification process, how well they have been captured, or if they still need to be captured. Captured status may mean that the tip 232 of the registration probe 230 has been placed within a predefined distance of the virtual landmark and it has been collected. A miscaptured status indicates that capture was attempted, i.e., system noted foot pedal press, button press, etc., but the virtual landmark was outside the predefined distance. An uncaptured status means that the virtual landmark still needs to be captured and no attempt to capture appears to have been made.

The HMD controller 210 controls the landmark images 260a, 260b (and/or the offset landmark images 264 if used) based on the status of the virtual landmarks. The landmark images 260a, 260b of the virtual landmarks with a captured status are no longer displayed. The landmark images 260a of the virtual landmarks having a miscaptured status are displayed in a first color. The landmark images 260b of the virtual landmarks having an uncaptured status are displayed in a second color, different than the first color. The miscaptured and uncaptured virtual landmarks can be differentiated from each other using other schemes, i.e., text-based notation next to the images, flashing images, different-shaped images, etc.

Figure 20:
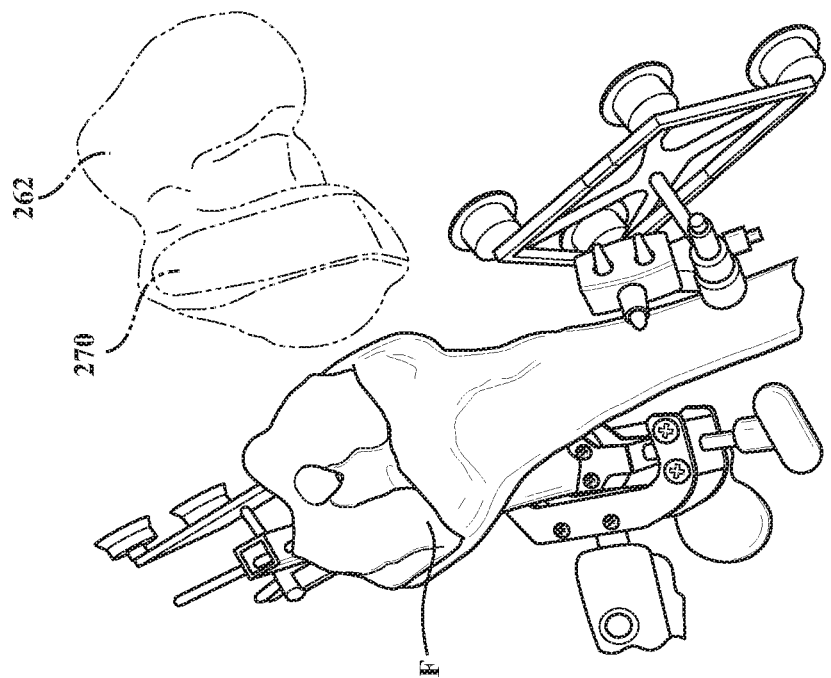
FIG. 20 is a perspective view of a femur and model images displayed offset from the femur by the HMD to represent a femur model and a cut-volume model.

Referring to FIG. 20, the HMD 200 can also be used to help users visualize treatment of the patient before actually treating the patient, to prepare for treatment of the patient, or to show progress of the treatment during the surgical procedure. In one embodiment, treatment involves the removal of tissue, e.g., bone, from the patient. In this case, the HMD 200 can be used to show the volume of material to be removed from the patient, the progression of removal, and the like. A virtual model, such as a three-dimensional model of the volume of material to be removed from the patient's bone may be defined in a model coordinate system, the femur coordinate system FBONE, etc. so that the virtual model can be transformed to/from any other coordinate system. For purposes of explanation, the model coordinate system MODEL1 (see FIG. 3) is registered to a common coordinate system (e.g., localizer coordinate system LCLZ, femur coordinate system FBONE, manipulator coordinated system MNPL, etc.) such that the virtual model and the volume of material to be removed from the patient's bone, as defined in the virtual model, are transformed to the common coordinate system.

The HMD coordinate system is also registered to the common coordinate system in the manner previously described. One or more treatment images 270 are generated with the HMD controller 210 to be displayed via the HMD 200. These treatment images 270, in the embodiment shown, represent at least a portion of the virtual model and the volume of material to be removed from the patient's bone. In one embodiment, the one or more treatment images 270 are displayed to the user with the HMD 200 in an offset manner with respect to the patient's bone such that an axis of the patient's bone is offset. As a result, the user is able to easily visualize the volume of material to be removed from the patient's bone. The volume of material to be removed may be depicted in a first color and portions of the patient's bone to remain may be depicted in a second color, different than the first color. These could also be differentiated using different patterns, different shades of color, or other visual methods. The volume of material to be removed may also be represented in layers, with different layers being displayed in different colors, patterns, shades, etc., to indicate to the user how deep the working end of the surgical tool 22 has penetrated during the procedure by showing the progress of removal in real-time.

The one or more treatment images 270 may be shown with the model image 262 in the same orientation as the actual bone (parallel axes) or at a different orientation. The one or more treatment images 270 and the model image 262 may be magnified relative to the actual bone, smaller than the actual bone, or displayed at the same size. The one or more treatment images 270 may also be displayed at a user-selectable orientation, magnification, rotation, etc. For instance, one of the input devices in communication with the HMD controller 210 may be used to select from a list of possible orientations, magnifications, rotations, etc. The input device may be a keyboard, mouse, touchscreen, voice activation, gesture sensor, etc. In one case, the user may use gesture commands identified via the gesture sensor (motion sensor 217, camera 214, or other sensor) of the HMD 200. The gesture sensor communicates with the HMD controller 210. The user may gesture with gesture commands how to rotate, tilt, size, etc., the one or more treatment images 270 with their hands. The HMD controller 210 uses the gesture sensor and gesture sensing algorithms to react accordingly to move/adjust the one or more treatment images 270 as desired by the user.

Figure 21:
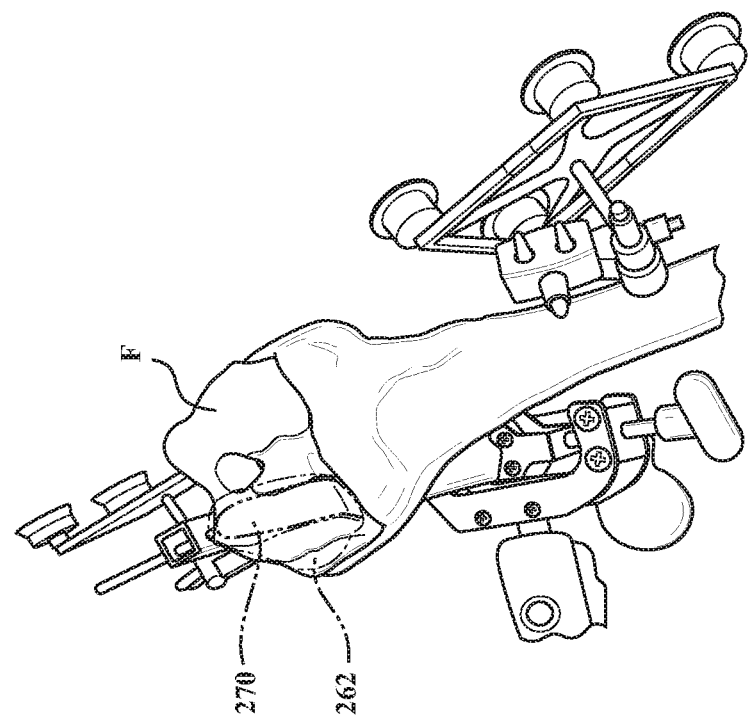
FIG. 21 is a perspective view of a femur and model images displayed overlaid on the femur by the HMD to represent the femur model and the cut-volume model.

In the embodiment shown in FIG. 21, the one or more treatment images 270 can be displayed to the user with the HMD 200 in an overlaid manner with respect to the patient's actual bone such that the user is able to visualize the volume of material to be removed from the patient's actual bone. The volume of material to be removed may be depicted in a first color and portions of the patient's bone to remain may be depicted in a second color, different than the first color, or different patterns, shades, etc. could be used. In the embodiment shown in FIG. 21, both the treatment image 270 depicting the volume of material to be removed and the model image 262 are shown overlaid on the actual bone, but in other embodiments, the model image 262 may be omitted with only the volume of material to be removed depicted with respect to the actual bone.

Figure 23:
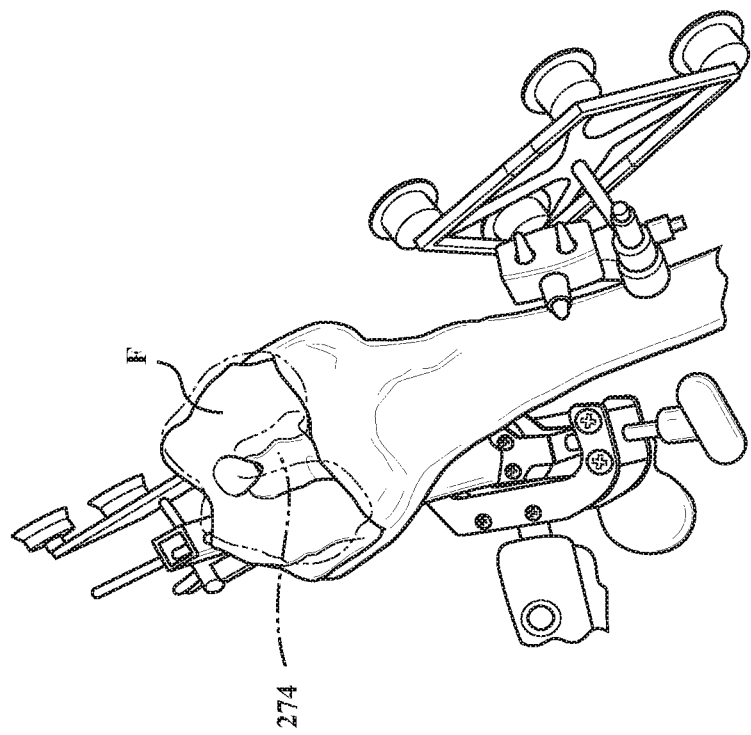
FIG. 23 is a perspective view of a femur and model image displayed overlaid on the femur by the HMD to represent a transparent femur model.
Figure 22:
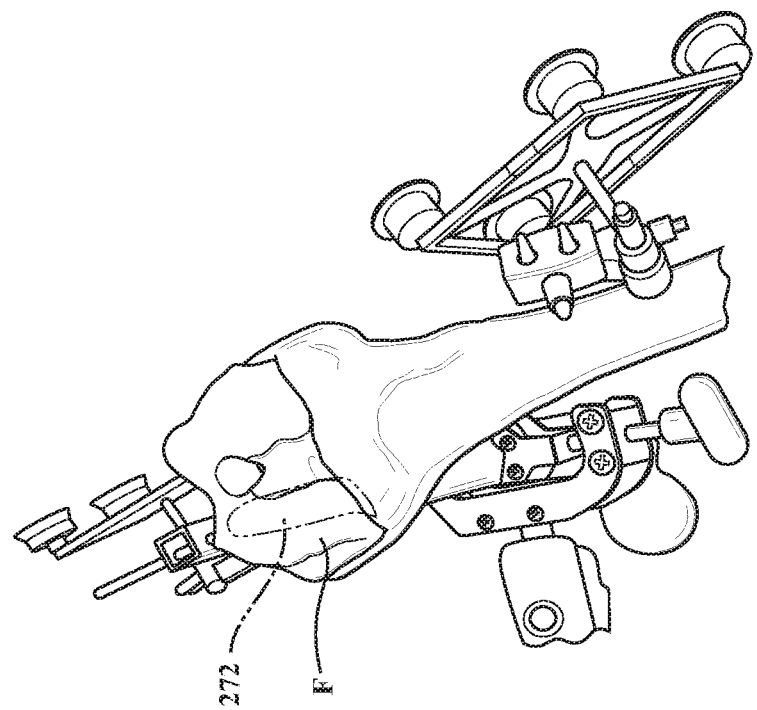
FIG. 22 is a perspective view of a femur and model image displayed overlaid on the femur by the HMD to represent an implant model.
Figure 24:
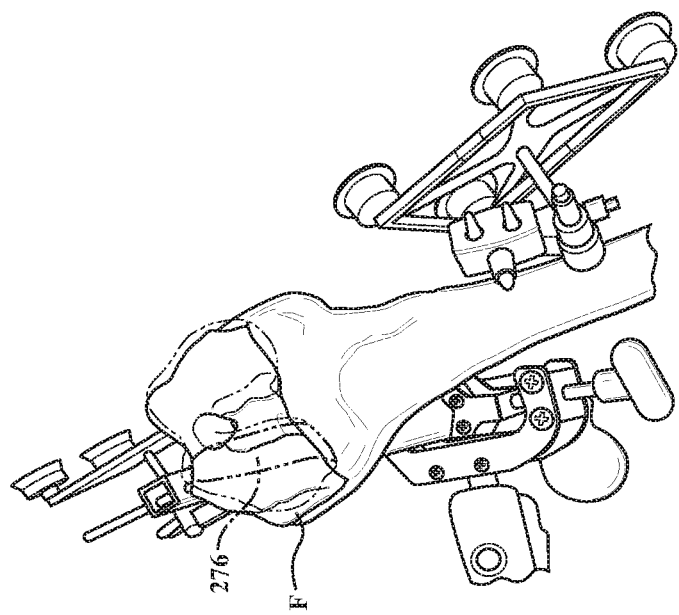
FIG. 24 is a perspective view of a femur and model image displayed overlaid on the femur by the HMD to represent the cut-volume model.

In still other embodiments, such as those shown in FIGS. 22-24, multiple virtual models can be displayed by the HMD 200 as being overlaid on one another, simultaneously depicted by the HMD 200, or otherwise displayed together in a meaningful manner. In FIG. 22, an implant image 272 depicting a virtual model of the implant to be placed on the bone can be displayed via the HMD 200 overlaid on the actual bone. A transparent model image 274 depicting the virtual model of the bone can be overlaid on the actual bone as shown in FIG. 23. A cut-volume image 276 depicting the virtual model of the volume of material to be removed can be overlaid on the actual bone, as shown in FIG. 24. These images 272, 274, 276 depict different virtual models (implant model, bone model, cut-volume model) and can be displayed simultaneously by the HMD 200 either on the actual bone in their proper poses or they could be displayed offset from the actual bone, in proper orientations (or different orientations), and/or at the same scale as the actual bone or magnified relative to the actual bone.

Figure 25:
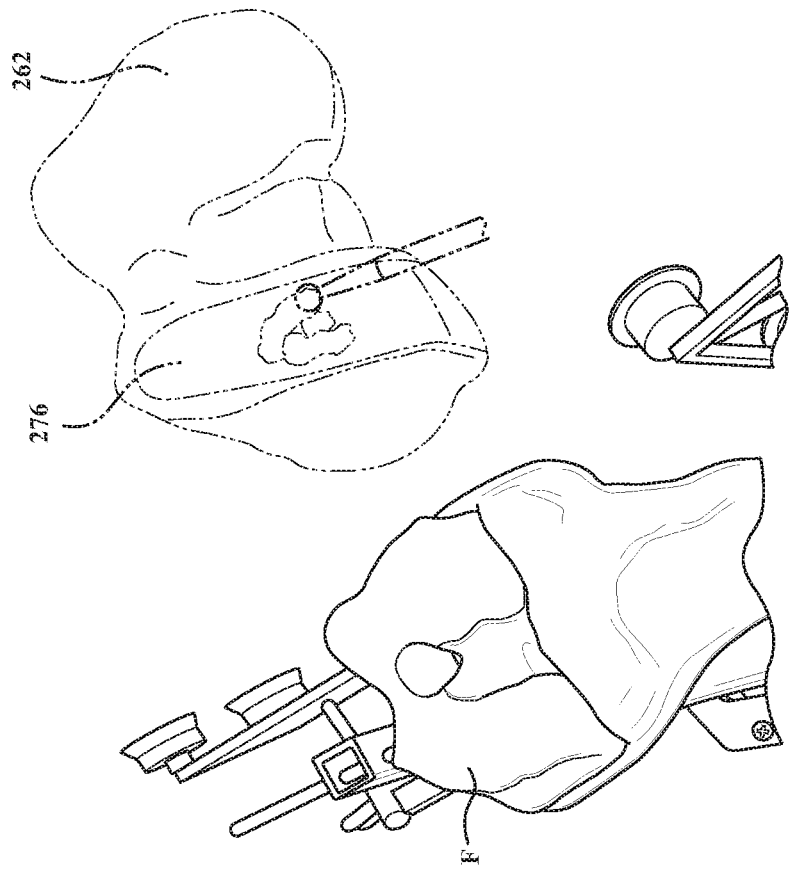
FIG. 25 is a perspective view of a femur and model images displayed offset from the femur by the HMD to represent the femur model, the cut-volume model, material being removed from the cut-volume model in real-time, and a surgical tool model.

Referring to FIG. 25, the virtual models may be updated during the procedure to reflect the current status of the procedure, e.g., depicting the volume of material already removed by the surgical tool 22, etc. In this case, the HMD controller 210 is configured to simultaneously update one or more of the images associated with one or more of the models to reflect the changes being made in real-time. For instance, the cut-volume model is a virtual model stored in the memory of the navigation controller 26 and/or manipulator controller 54 (as are the other models) and the HMD controller 210 generates one or more images that represents the cut-volume model. As material is removed, the cut-volume model is updated by subtracting the volume associated with the working end of the surgical tool 22 (e.g. the bur volume) thereby updating the cut-volume model. In this case, the cut-volume model may be a voxel-based solid body model with voxels removed that are in the path of the working end of the surgical tool 22 during the procedure, as determined by the navigation system 20. The HMD controller 210 updates the cut-volume image(s) 276 associated with the cut-volume model as treatment progresses and material is removed. This can be performed in a similar manner by removing portions of the image or whole images as cutting progresses based on the position of the working end of the surgical tool 22 in the common coordinate system being utilized.

Figure 27:
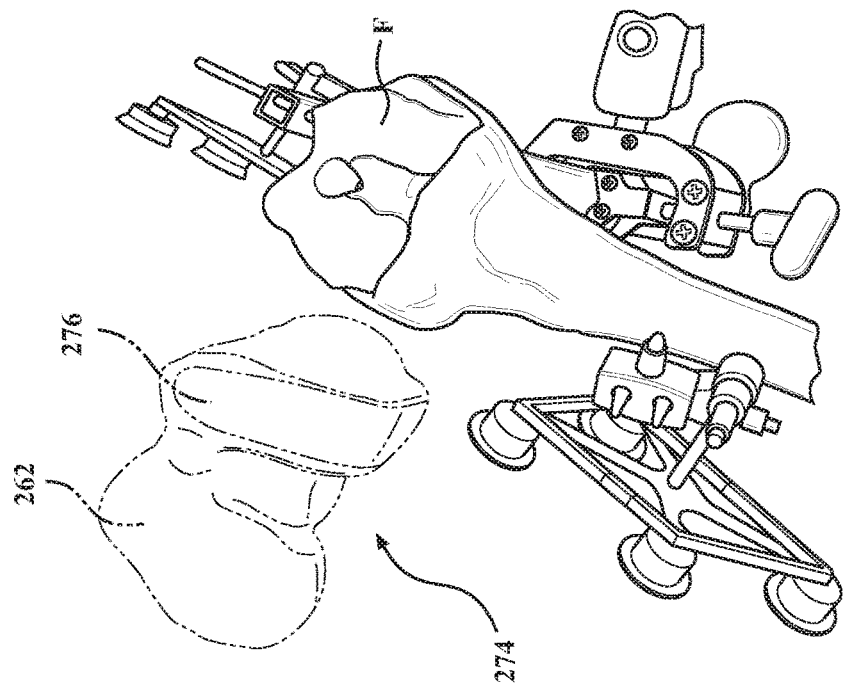
FIG. 27 is a perspective view of a femur and model images displayed offset from the femur on the right side of the patient by the HMD to represent the femur model and the cut-volume model.
Figure 26:
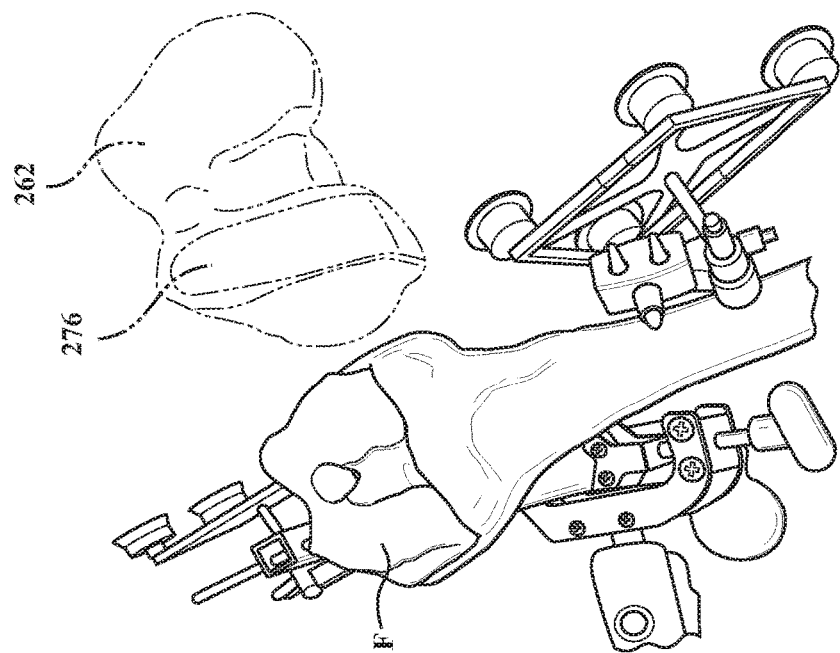
FIG. 26 is a perspective view of a femur and model images displayed offset from the femur on the left side of the patient by the HMD to represent the femur model and the cut-volume model.

Referring to FIGS. 26 and 27, the model images 262 and/or other images overlaid thereon or depicted therewith may be offset from the actual bone in a manner that depends on a configuration of the manipulator 12 and/or the particular anatomy being treated. For instance, if the user's left femur is being treated, the offset may be to the left of the left femur (e.g., from patient's perspective). Conversely, if the right femur is being treated, the offset may be to the right of the right femur. If the manipulator 12 is located on one side of an operating table, the offset may be toward the other side, etc. In other words, the images may be displayed based on manipulator position, anatomy position, or the like.

The HMD 200 is generally configured to change the viewing angle of the images being shown based on the location of the HMD 200. So, if the model image 262 is configured to be offset relative to the actual bone, but in the same orientation, as the user moves around the patient and to the side of the actual bone, the model image 262 also changes in kind so that the user now seemingly sees a different view of the model image 262—in line with the actual bone, for instance. Alternatively, the model image 262 could be configured to always be offset from the actual bone, just in a different direction as the user moves around the actual bone. The HMD 200 could also be configured to show the model images 262 as simplified two-dimensional views, e.g., top view, bottom view, right side view, left side view, front view, and rear view, based on the location of the HMD 200. If the HMD 200 is located to be viewing down on the actual bone, then the top view is generated by the HMD controller 210 and shown through the HMD 200. If the HMD 200 is located to be viewing the right side of the actual bone, then the right side view is generated and shown through the HMD 200 and so on.

The HMD 200 can also be used to provide gross registration of two or more objects by visually depicting images that represent virtual models of the objects and then, through some form of input, moving the images to be overlaid on the objects. For instance, referring to FIG. 28, the HMD controller 210 is configured to display model images 262a and 262b representing virtual models of the femur F and tibia T. Since registration has not yet been completed to fit the virtual models of the bones to the actual bones, the model images 262a and 262b appear off in space relative to the actual bones. Gross registration can be performed with an input device such as the gesture sensor. In this case the user, swipes, rotates, sizes, etc. each of the model images 262a, 262b separately until each model image 262a, 262b is generally coinciding with the actual bone. This can be done before and/or after any incisions are made to access the bone and before and/or after the bone trackers 44, 46 are attached to the bone. This gross registration can be performed before more refined registration occurs. By performing gross registration first, final registration can be greatly simplified and confidence in the final registration can be higher from the user's perspective given their hands-on involvement and visualization during the gross registration. Virtual images that represent the virtual models of the bones can also be displayed through the HMD 200 after final registration so that the user can quickly see how well the bone models are registered to the actual bone.

Similarly, the model images 262a, 262b can be used to illustrate various positions of the leg, bones, or other objects in pre-operative, intra-operative, and/or post-operative positions, even before the surgery begins. For instance, the surgeon may wish to see how the femur F and tibia T will be positioned after treatment, e.g., after implants are placed. This may include showing the pre-operative *varus*/valgus position of the leg before surgery and the predicted post-operative *varus*/valgus positions based on the implants selected by the surgeon. The model images 262a, 262b then may change as the surgeon changes implant sizes and/or placement.

Referring to FIG. 29, the HMD 200 can also be used to visually depict a desired tool path for the working end of the surgical tool 22 to follow during manual movement of the surgical tool 22. Similarly, the HMD 200 can visually depict the tool path that the working end of the surgical tool 22 will follow during autonomous movement of the manipulator 12. This could be a pre-operatively defined tool path based, for instance, on the particular size and placement of the implant selected by the surgeon, and/or other factors. The tool path can also be defined as described in U.S. Pat. No. 9,119,655, entitled, "Surgical Manipulator Capable of Controlling a Surgical Instrument in Multiple Modes," the disclosure of which is hereby incorporated by reference. The navigation controller 26 and/or the manipulator controller 54 can store the tool path and its associated location data. This location data is transmitted to the HMD controller 210, which generates a tool path image 280 visually coinciding with the stored tool path such that the HMD 200 displays the tool path image 280 to seemingly be located in the actual bone at the actual locations that the working end (e.g., the bur) will traverse along the tool path either autonomously or manually. The entire tool path can be displayed to the user or only portions of the tool path might be displayed, such as only those portions that have not yet been traversed. In some cases, as the working end of the surgical tool 22 successfully follows along segments of the tool path, images associated with those segments may disappear and no longer be displayed. In some cases, only a small section of the tool path is displayed ahead of the working end of the surgical tool 22 to act as a general guide, but not the entire tool path.

In other embodiments, the HMD 200 may be used to predict collisions that could occur between objects. Still referring to FIG. 29, the navigation controller 26 and/or manipulator controller 54 may control an orientation of the surgical tool 22 as the working end of the surgical tool 22 traverses along the tool path. See U.S. Pat. No. 9,119,655, entitled, "Surgical Manipulator Capable of Controlling a Surgical Instrument in Multiple Modes," the disclosure of which is hereby incorporated by reference. In this case, since the navigation system 20 and/or manipulator 12 knows how the surgical tool 22 will be positioned and oriented along the entire tool path, this position and orientation data can be provided to the HMD controller 210 so that the HMD controller 210 can generate corresponding position and/or orientation images 282 along one or more segments of the tool path to visually depict to the user how the surgical tool 22 may be positioned and/or oriented in the future with respect to the actual bone. Accordingly, as illustrated in FIG. 29, this can be helpful to predict collisions that may occur, such as the collision predicted between the surgical tool 22 and the bone tracker 44 shown.

Referring to FIG. 30, the HMD 200 may also be used to visually depict virtual boundaries and/or virtual workspaces associated with the particular treatment of the patient. For instance, the cut-volume model image 262 associated with femur F shown in FIG. 30 includes the volume of material to be removed from the femur F as previously described, but there also exists a more expansive cutting boundary 284 that defines the space within which the working end of the surgical tool 22 may be operational, e.g., the space in which the bur is allowed to rotate via a tool motor and tool controller (see FIG. 2). In this case, the cutting boundary 284 is located partially above the bone surface of the femur F and the cut-volume and expands away from the femur F to provide an enlarged mouth portion 286. If the working end of the cutting tool 22 strays near and/or outside of this cutting boundary 284, haptic feedback may be generated via the manipulator 12 in the manner described in U.S. Pat. No. 8,010,180, hereby incorporated by reference. This haptic feedback indicates to the user that the working end of the surgical tool 22 is approaching the boundary 284, has reached the boundary 284, or is beyond the boundary 284. In some cases, the boundary is represented as a path, such as a trajectory along which the surgical tool 22 is expected to be oriented and/or along which the surgical tool 22 is expected to traverse. In this case, the haptic feedback may indicate to the user that the surgical tool 22 has been reoriented off the trajectory or has moved too far along the trajectory.

The navigation controller 26 and/or manipulator controller 54 has location data for this cutting boundary 284 (also referred to as a workspace) that is tied to the cut-volume model and/or the virtual model of the bone and/or the implant selected for the procedure. In one embodiment, each implant has its own cut-volume model and cutting boundary model associated with it. Thus, when the implant is selected and placed on the virtual model of the bone, then the cut-volume model and the cutting boundary model become fixed relative to the virtual model of the bone and the actual bone. The HMD controller 210 is then able to generate the model images 262, 284 associated with the cut-volume model and the cutting boundary model and display them via the HMD 200 at their appropriate locations relative to the actual bone.

Figure 31:
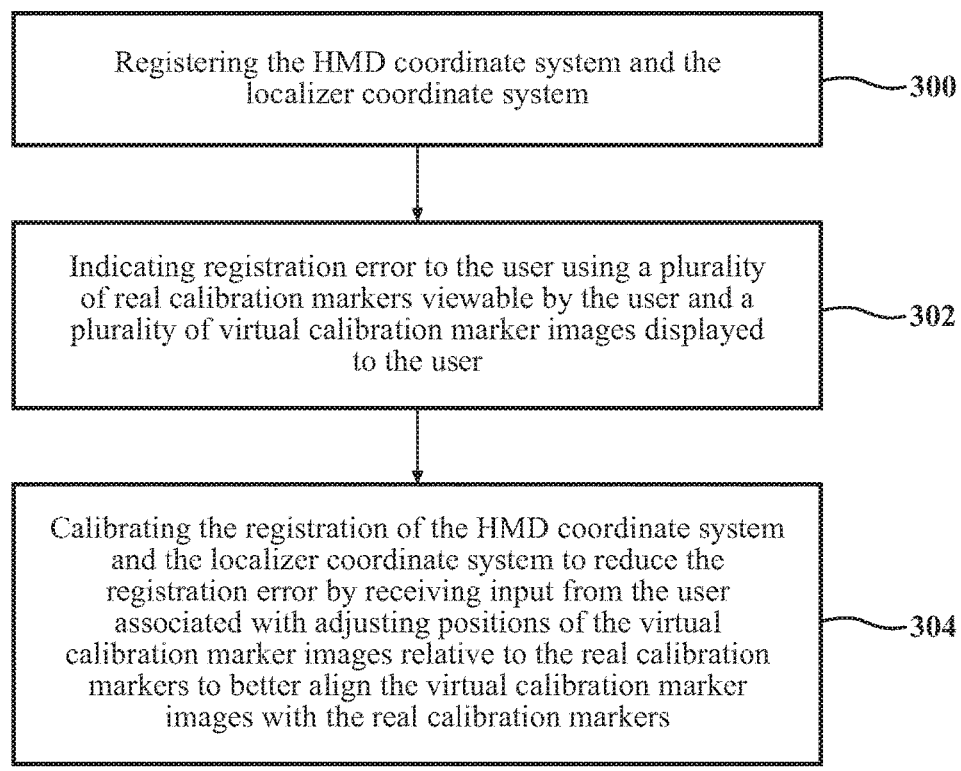
FIGS. 31-45 illustrate various steps of exemplary methods.

Referring to FIG. 31, a method of calibrating registration of the HMD coordinate system and the localizer coordinate system LCLZ is shown. The HMD coordinate system is associated with the HMD 200 and the localizer coordinate system LCLZ is associated with the localizer 34. The method comprises, in step 300, registering the HMD coordinate system and the localizer coordinate system LCLZ such that images displayed by the HMD 200 can be associated with real objects tracked by the localizer (e.g., the surgical tool 22, the femur F, the tibia T, etc.). Registration error is indicated to the user in step 302 using the plurality of real calibration markers 234 viewable by the user and the plurality of virtual calibration marker images 238 displayed to the user. The virtual calibration marker images 238 have a congruency with the real calibration markers 234 so that the virtual calibration marker images 238 are capable of being aligned with the real calibration markers 234 whereby a magnitude of misalignment is indicative of the registration error. In step 304, the registration of the HMD coordinate system and the localizer coordinate system LCLZ is calibrated to reduce the registration error by receiving input from the user associated with adjusting positions of the virtual calibration marker images 238 relative to the real calibration markers 234 to better align the virtual calibration marker images 238 with the real calibration markers 234.

Figure 32:
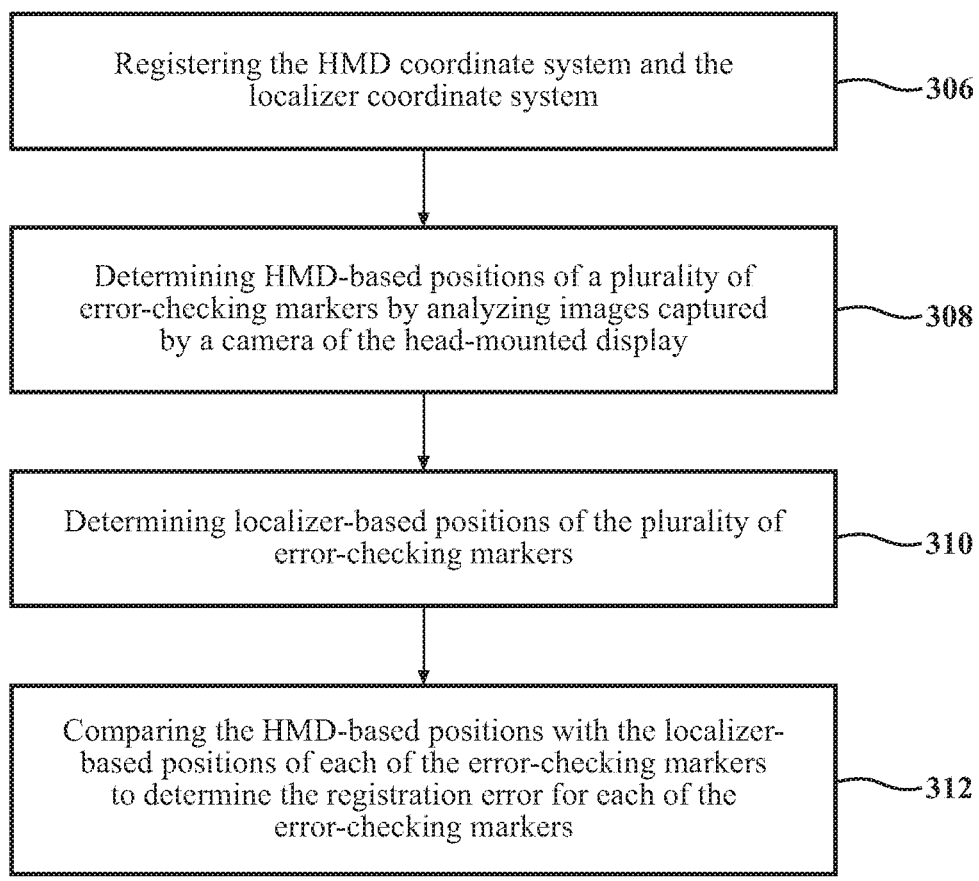

Referring to FIG. 32, a method of determining registration error in registration of the HMD coordinate system and the localizer coordinate system LCLZ is shown. The HMD coordinate system is associated with the HMD 200 and the localizer coordinate system LCLZ is associated with the localizer 34. The method comprises, in step 306, registering the HMD coordinate system and the localizer coordinate system LCLZ such that images displayed with the HMD 200 can be associated with real objects tracked by the localizer 34. HMD-based positions of the plurality of error-checking markers 242 are determined in step 308 by analyzing images captured by the camera 214 of the HMD 200. Localizer-based positions of the plurality of error-checking markers 242 are determined in step 310 by placing the tip 232 of the navigation probe 230 in the known location with respect to each of the error-checking markers 242. Navigation markers 224 of the navigation probe 230 are simultaneously sensed with one or more position sensors 40 of the localizer 34. The HMD-based positions are then compared in step 312 with the localizer-based positions of each of the error-checking markers 242 to determine the registration error for each of the error-checking markers 242.

Figure 33:
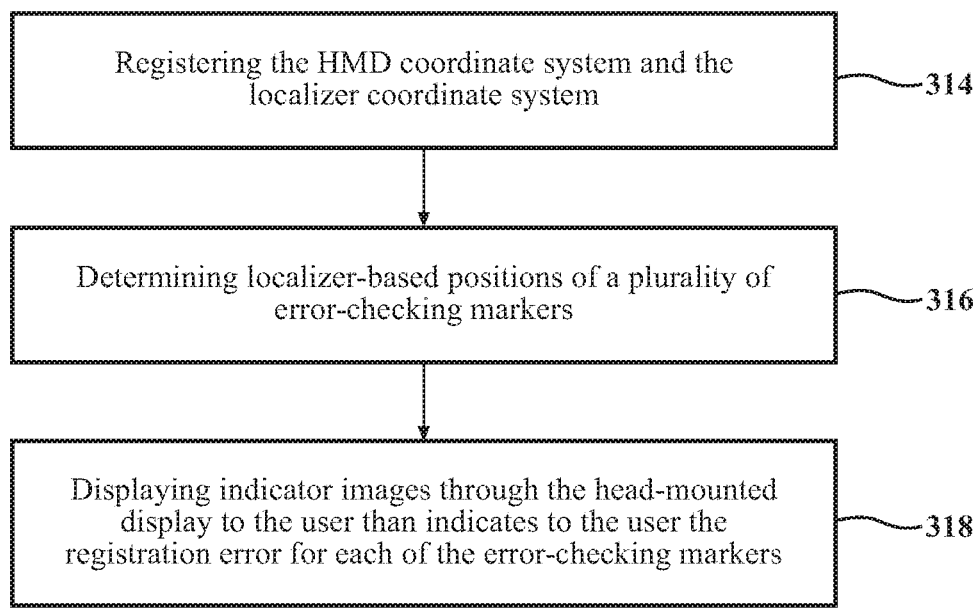

Referring to FIG. 33, another method of determining registration error in registration of the HMD coordinate system and the localizer coordinate system LCLZ is shown. The HMD coordinate system is associated with the HMD 200 and the localizer coordinate system LCLZ is associated with the localizer 34. The method comprises, in step 314, registering the HMD coordinate system and the localizer coordinate system LCLZ such that images displayed with the HMD 200 can be associated with real objects tracked by the localizer 34. Localizer-based positions of the plurality of error-checking markers are determined in step 316 by placing the tip 232 of the navigation probe 230 at locations associated with each of the error-checking markers. Navigation markers of the navigation probe are simultaneously sensed with one or more position sensors of the localizer. The plurality of error-checking markers are located on the substrate 246 separate from the HMD 200 and the localizer 34. Indicator images 250 are displayed through the HMD 200 to the user in step 318 that indicates to the user the registration error for each of the error-checking markers. The substrate 246 comprises the visible error scale and the indicator images 250 are displayed with respect to the visible error scale to manually determine the registration error.

Figure 34:
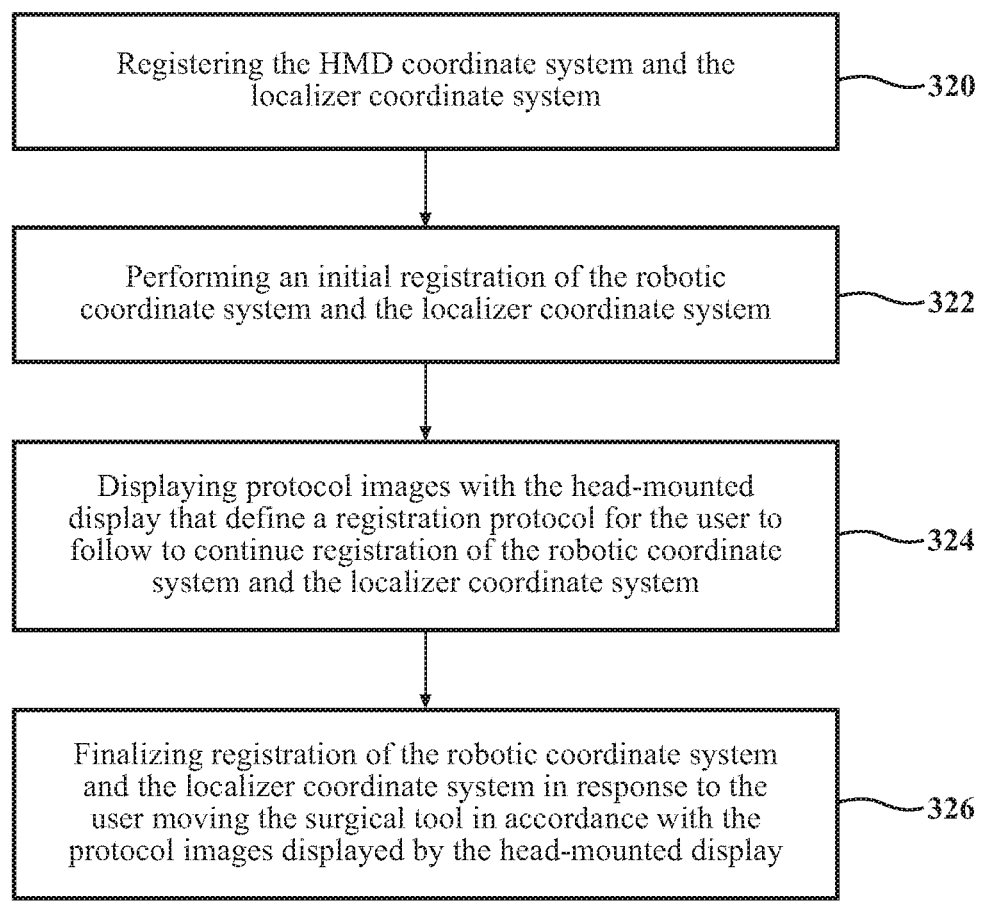

Referring to FIG. 34, a method of registering a robotic coordinate system, such as the manipulator coordinate system MNPL, and the localizer coordinate system LCLZ using the HMD 200 is shown. The robotic coordinate system is associated with a surgical robot, such as the manipulator 12. The localizer coordinate system LCLZ is associated with the localizer 34. The head-mounted display has the HMD coordinate system. The method comprises, in step 320, registering the HMD coordinate system and the localizer coordinate system LCLZ such that images displayed with the HMD 200 can be associated with real objects tracked by the localizer 34. An initial registration of the robotic coordinate system and the localizer coordinate system LCLZ is performed in step 322 by sensing base tracking markers 224 mounted to the surgical robot and by sensing tool tracking markers 224 temporarily mounted to the surgical tool 22 coupled to the surgical robot. Protocol images 258 are displayed in step 324 with the HMD 200 that define the registration protocol for the user to follow to continue registration of the robotic coordinate system and the localizer coordinate system LCLZ. The registration protocol comprises movement indicators to indicate to the user movements to be made with the surgical tool 22 while the tool tracking markers 224 are temporarily mounted to the surgical tool 22. Registration of the robotic coordinate system and the localizer coordinate system LCLZ is finalized in step 326 in response to the user moving the surgical tool in accordance with the protocol images 258 displayed by the HMD 200.

Figure 35:
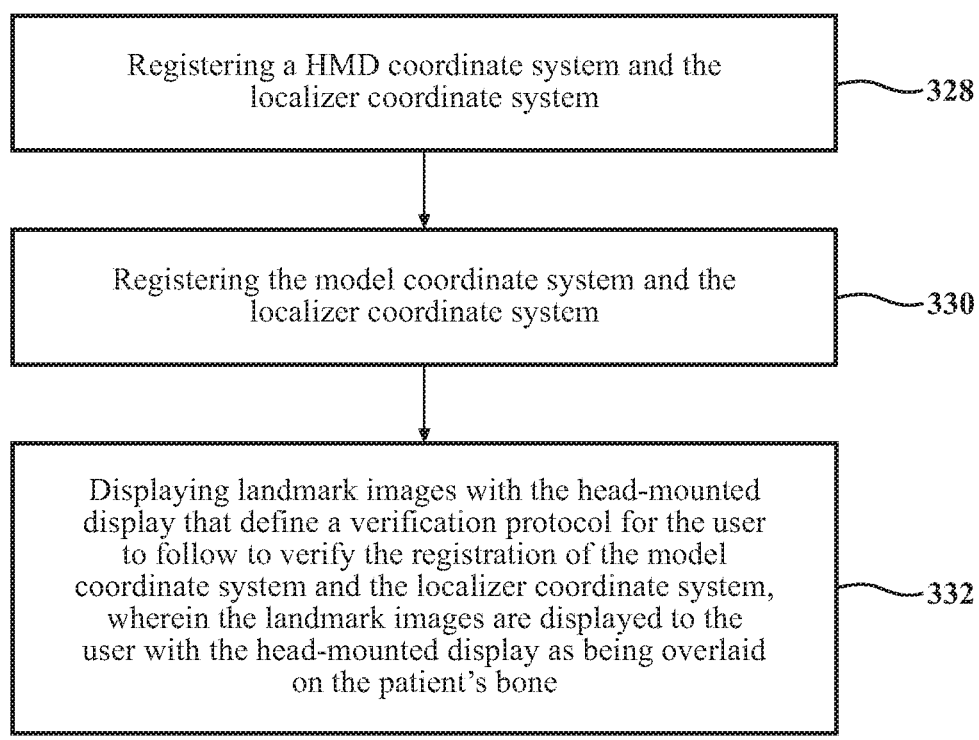

Referring to FIG. 35, a method of verifying registration of the model coordinate system MODEL2 and the localizer coordinate system LCLZ is shown. The model coordinate system MODEL2 is associated with the virtual model of the patient's bone and the localizer coordinate system LCLZ is associated with the localizer 34. The method comprises, in step 328, registering the HMD coordinate system and the localizer coordinate system LCLZ. The HMD coordinate system is associated with the HMD 200 such that images displayed with the HMD 200 can be associated with real objects tracked by the localizer 34. The model coordinate system MODEL2 and the localizer coordinate system LCLZ are registered in step 330 by placing the tip 232 of the navigation probe 230 at locations on the patient's bone and simultaneously sensing navigation markers 224 of the navigation probe 230 with one or more position sensors 40 of the localizer 34. Landmark images 260 are displayed in step 332 with the HMD 200 that define the verification protocol for the user to follow to verify the registration of the model coordinate system MODEL2 and the localizer coordinate system LCLZ. The landmark images 260 depict virtual landmarks associated with the virtual model of the patient's bone. The landmark images 260 are displayed to the user with the HMD 200 as being overlaid on the patient's bone such that the user is able to verify registration by placing the tip 232 of the navigation probe 230 on the patient's bone while positioning the tip 232 of the navigation probe 230 in desired positions relative to the user's visualization of the landmark images 260.

Figure 36:
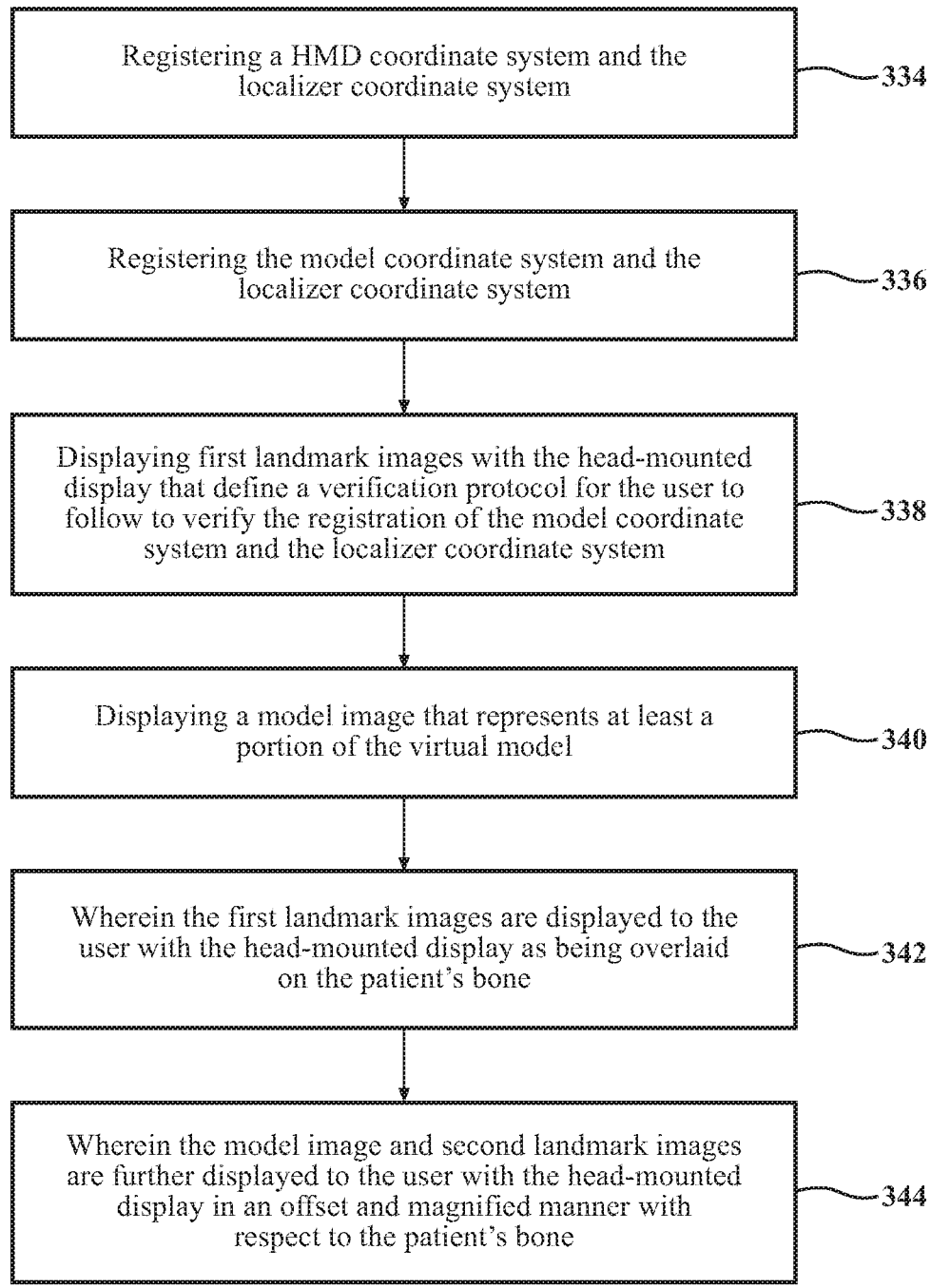

Referring to FIG. 36, another method of verifying registration of the model coordinate system MODEL2 and the localizer coordinate system LCLZ is shown. The model coordinate system MODEL2 is associated with the virtual model of the patient's bone and the localizer coordinate system LCLZ is associated with the localizer 34. The method comprises, in step 334, registering the HMD coordinate system and the localizer coordinate system LCLZ. The HMD coordinate system is associated with the HMD 200 such that images displayed with the HMD 200 can be associated with real objects tracked by the localizer 34. The model coordinate system MODEL2 and the localizer coordinate system LCLZ are registered in step 336 by placing the tip 232 of the navigation probe 230 at locations on the patient's bone and simultaneously sensing navigation markers 224 of the navigation probe 230 with one or more position sensors 40 of the localizer 34. First landmark images 260 are displayed in step 338 with the HMD 200 that define the verification protocol for the user to follow to verify the registration of the model coordinate system MODEL2 and the localizer coordinate system LCLZ. The first landmark images 260 depict virtual landmarks associated with the virtual model of the patient's bone. The model image 262 is displayed in step 340 that represents at least a portion of the virtual model. The first landmark images 260 are displayed in step 342 to the user with the HMD 200 as being overlaid on the patient's bone such that the user is able to verify registration by placing the tip 232 of the navigation probe 230 on the patient's bone while positioning the tip 232 of the navigation probe 230 in desired positions relative to the user's visualization of the first landmark images 260. The model image 262 and second landmark images 264 are further displayed to the user in step 344 with the HMD 200 in an offset and magnified manner with respect to the patient's bone such that the axis of the patient's bone is parallel and offset to a corresponding axis of the model image 262 such that the user is able to verify registration by placing the tip 232 of the navigation probe 230 on the patient's bone while simultaneously visualizing the virtual position of the tip 232 of the navigation probe 230 relative to the second landmark images 264.

Figure 37:
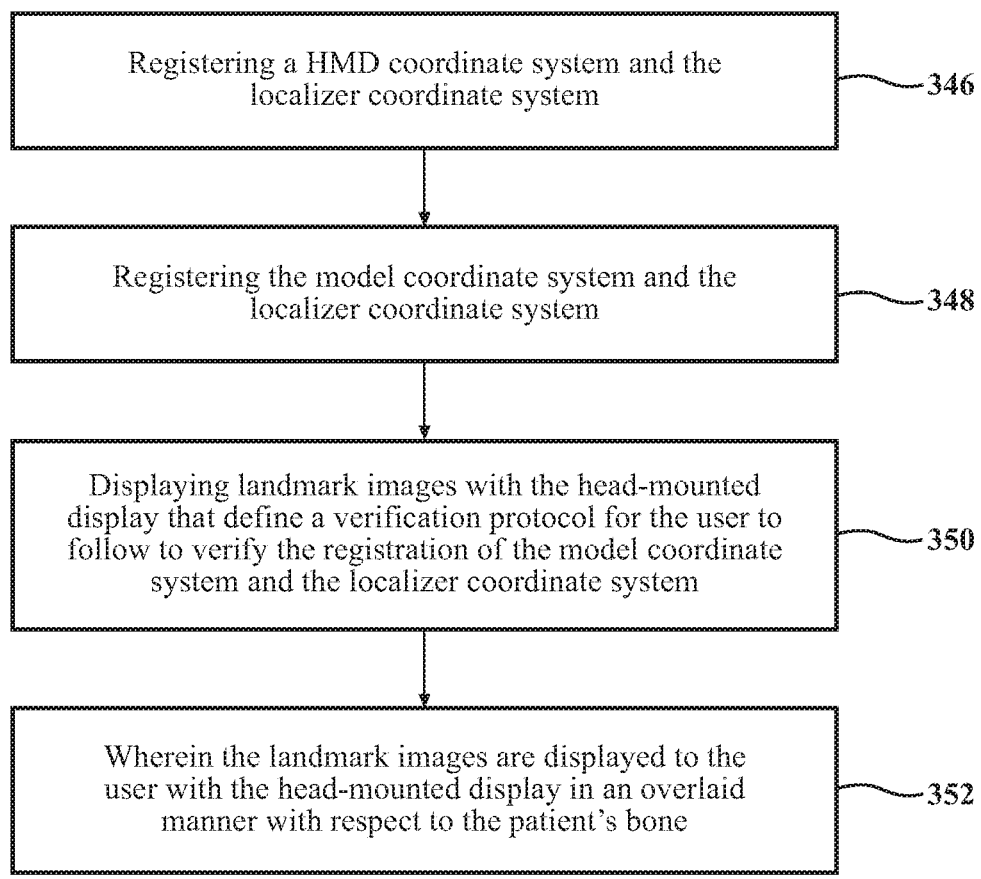

Referring to FIG. 37, another method of verifying registration of the model coordinate system MODEL2 and the localizer coordinate system LCLZ is shown. The model coordinate system MODEL2 is associated with the virtual model of the patient's bone and the localizer coordinate system LCLZ is associated with the localizer 34. The method comprises, in step 346, registering the HMD coordinate system and the localizer coordinate system LCLZ. The HMD coordinate system is associated with the HMD 200 such that images displayed with the HMD 200 can be associated with real objects tracked by the localizer 34. The model coordinate system MODEL2 and the localizer coordinate system LCLZ are registered in step 348 by placing the tip 232 of the navigation probe 230 at locations on the patient's bone and simultaneously sensing navigation markers 224 of the navigation probe 230 with one or more position sensors 40 of the localizer 34. Landmark images 260 are displayed in step 350 with the HMD 200 that define the verification protocol for the user to follow to verify the registration of the model coordinate system MODEL2 and the localizer coordinate system LCLZ. The landmark images 260 depict virtual landmarks associated with the virtual model of the patient's bone. The landmark images 260 are displayed to the user in step 352 with the HMD 200 in an overlaid manner with respect to the patient's bone such that the user is able to verify registration by placing the tip 232 of the navigation probe 230 on the patient's bone adjacent to each of the landmark images 260 and capturing points on the patient's bone adjacent to each of the landmark images 260 to determine if the points on the patient's bone are within the predetermined tolerance to the virtual landmarks.

Figure 38:
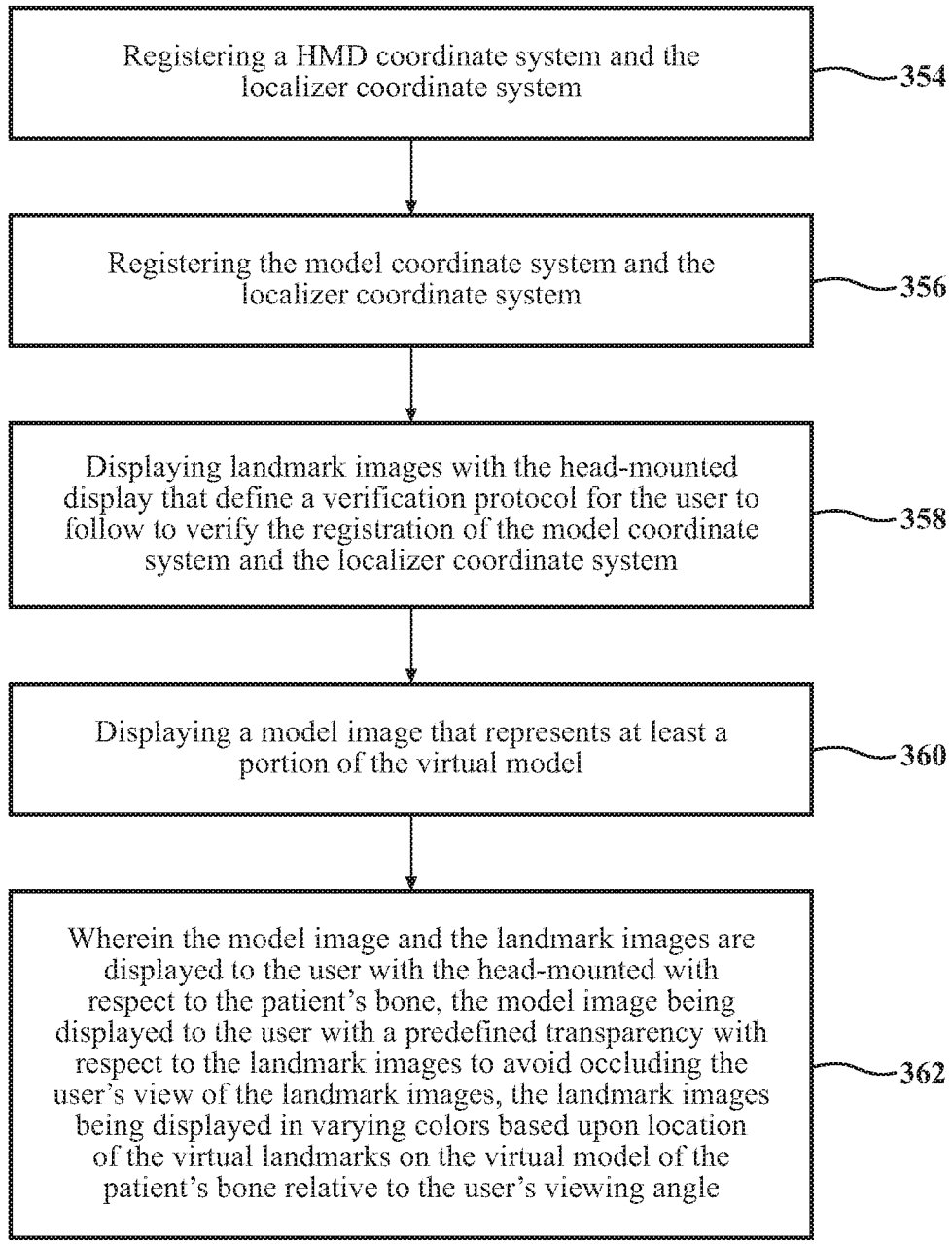

Referring to FIG. 38, another method of verifying registration of the model coordinate system MODEL2 and the localizer coordinate system LCLZ is shown. The model coordinate system MODEL2 is associated with the virtual model of the patient's bone and the localizer coordinate system LCLZ is associated with the localizer 34. The method comprises, in step 354, registering the HMD coordinate system and the localizer coordinate system LCLZ. The HMD coordinate system is associated with the HMD 200 such that images displayed with the HMD 200 can be associated with real objects tracked by the localizer 34. The model coordinate system MODEL2 and the localizer coordinate system LCLZ are registered in step 356 by placing the tip 232 of the navigation probe 230 at locations on the patient's bone and simultaneously sensing navigation markers 224 of the navigation probe 230 with one or more position sensors 40 of the localizer 34. Landmark images 260a, 260b, 264a, 264b are displayed in step 358 with the HMD 200 that define the verification protocol for the user to follow to verify the registration of the model coordinate system MODEL2 and the localizer coordinate system LCLZ. The landmark images 264a, 264b depict virtual landmarks associated with the virtual model of the patient's bone. The model image 262 is displayed in step 360 that represents at least a portion of the virtual model. The model image 262 and the landmark images 264a, 264b are displayed to the user with the HMD 200 with respect to the patient's bone. The model image 262 is displayed to the user in step 362 with the predefined transparency with respect to the landmark images 264a, 264b to avoid occluding the user's view of the landmark images 264a, 264b. The landmark images 264a, 264b are displayed in varying colors based upon location of the virtual landmarks on the virtual model of the patient's bone relative to the user's viewing angle.

Figure 39:
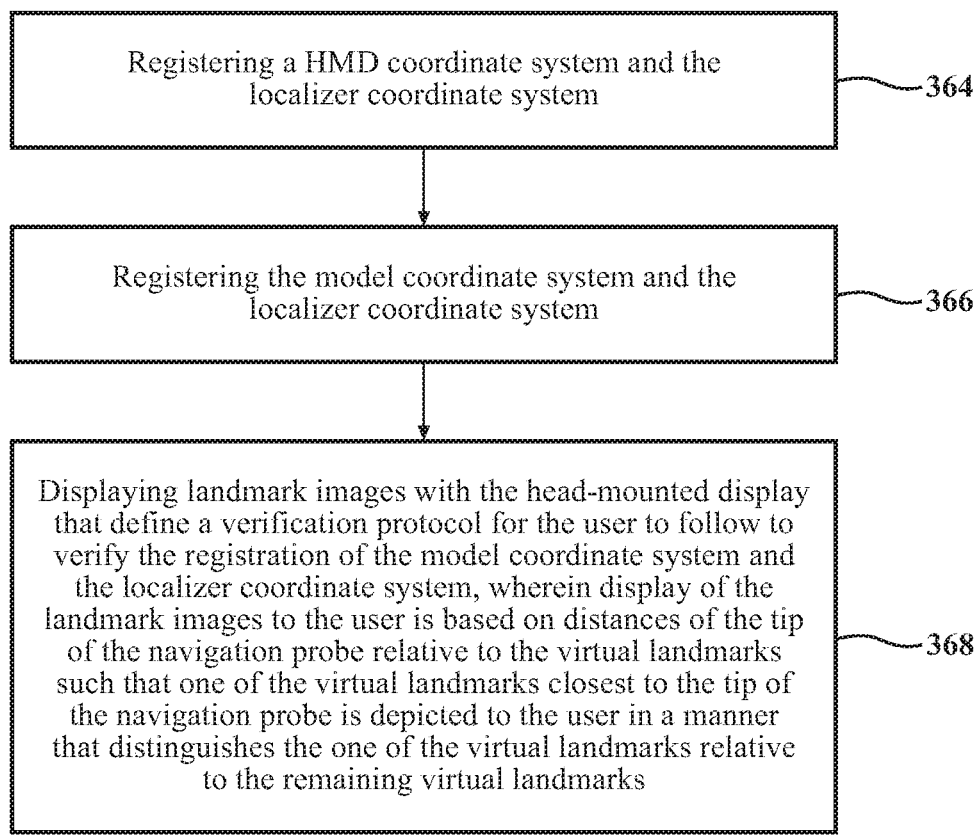

Referring to FIG. 39, another method of verifying registration of the model coordinate system MODEL2 and the localizer coordinate system LCLZ is shown. The model coordinate system MODEL2 is associated with the virtual model of the patient's bone and the localizer coordinate system LCLZ is associated with the localizer 34. The method comprises, in step 364, registering the HMD coordinate system and the localizer coordinate system LCLZ. The HMD coordinate system is associated with the HMD 200 such that images displayed with the HMD 200 can be associated with real objects tracked by the localizer 34. The model coordinate system MODEL2 and the localizer coordinate system LCLZ are registered in step 366 by placing the tip 232 of the navigation probe 230 at locations on the patient's bone and simultaneously sensing navigation markers 224 of the navigation probe 230 with one or more position sensors 40 of the localizer 34. Landmark images 260, 264 are displayed in step 368 with the HMD 200 that define the verification protocol for the user to follow to verify the registration of the model coordinate system MODEL2 and the localizer coordinate system LCLZ. The landmark images 260, 264 depict virtual landmarks associated with the virtual model of the patient's bone. Display of the landmark images 264 to the user is based on distances of the tip 232 of the navigation probe 230 relative to the virtual landmarks such that one of the virtual landmarks closest to the tip 232 of the navigation probe 230 is depicted to the user in a manner that distinguishes the one of the virtual landmarks relative to the remaining virtual landmarks.

Figure 40:
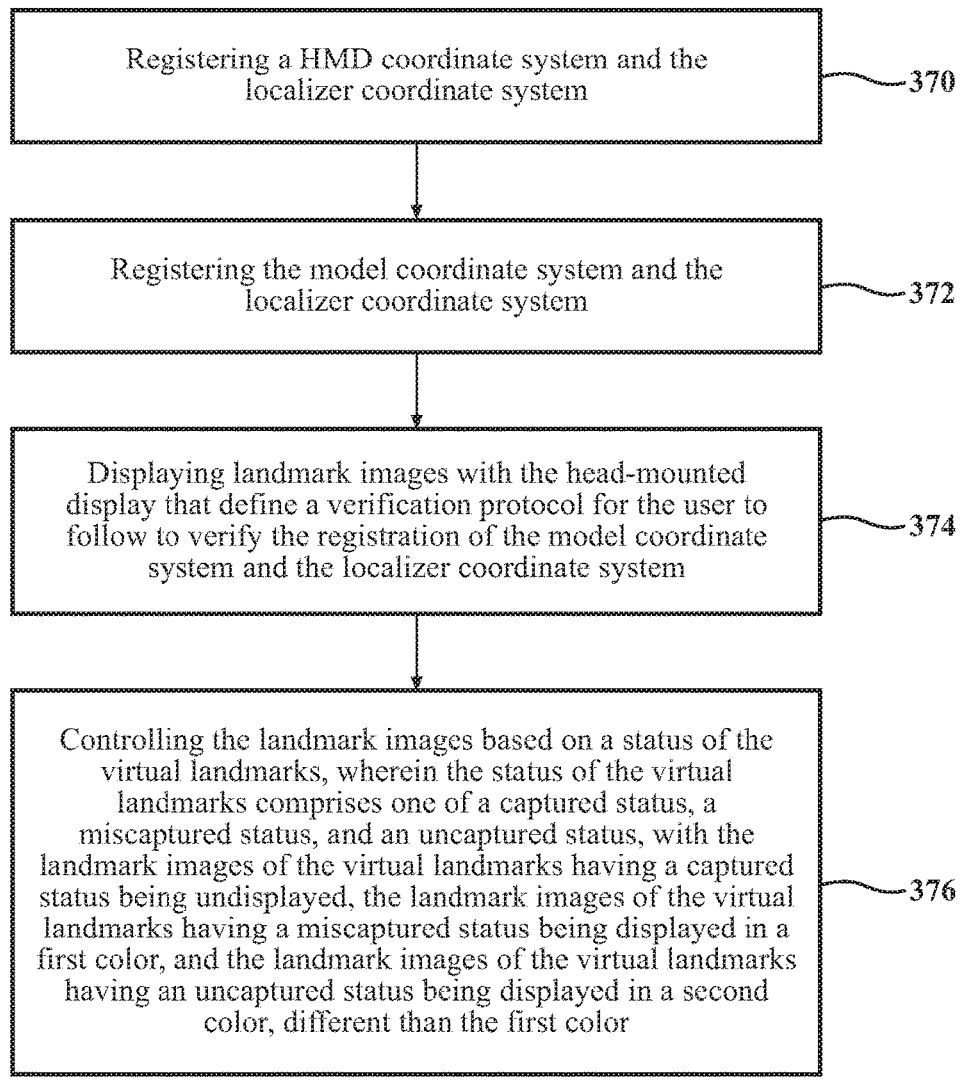

Referring to FIG. 40, another method of verifying registration of the model coordinate system MODEL2 and the localizer coordinate system LCLZ is shown. The model coordinate system MODEL2 is associated with the virtual model of the patient's bone and the localizer coordinate system LCLZ is associated with the localizer 34. The method comprises, in step 370, registering the HMD coordinate system and the localizer coordinate system LCLZ. The HMD coordinate system is associated with the HMD 200 such that images displayed with the HMD 200 can be associated with real objects tracked by the localizer 34. The model coordinate system MODEL2 and the localizer coordinate system LCLZ are registered in step 372 by placing the tip 232 of the navigation probe 230 at locations on the patient's bone and simultaneously sensing navigation markers 224 of the navigation probe 230 with one or more position sensors 40 of the localizer 34. Landmark images 260, 264 are displayed in step 374 with the HMD 200 that define the verification protocol for the user to follow to verify the registration of the model coordinate system MODEL2 and the localizer coordinate system LCLZ. The landmark images 260, 264 depict virtual landmarks associated with the virtual model of the patient's bone. The landmark images 260, 264 are controlled in step 376 based on the status of the virtual landmarks, wherein the status of the virtual landmarks comprises one of the captured status, the miscaptured status, and the uncaptured status. The landmark images of the virtual landmarks that have the captured status are not displayed. The landmark images of the virtual landmarks that have the miscaptured status are displayed in the first color. The landmark images of the virtual landmarks that have the uncaptured status are displayed in the second color, different than the first color.

Figure 41:
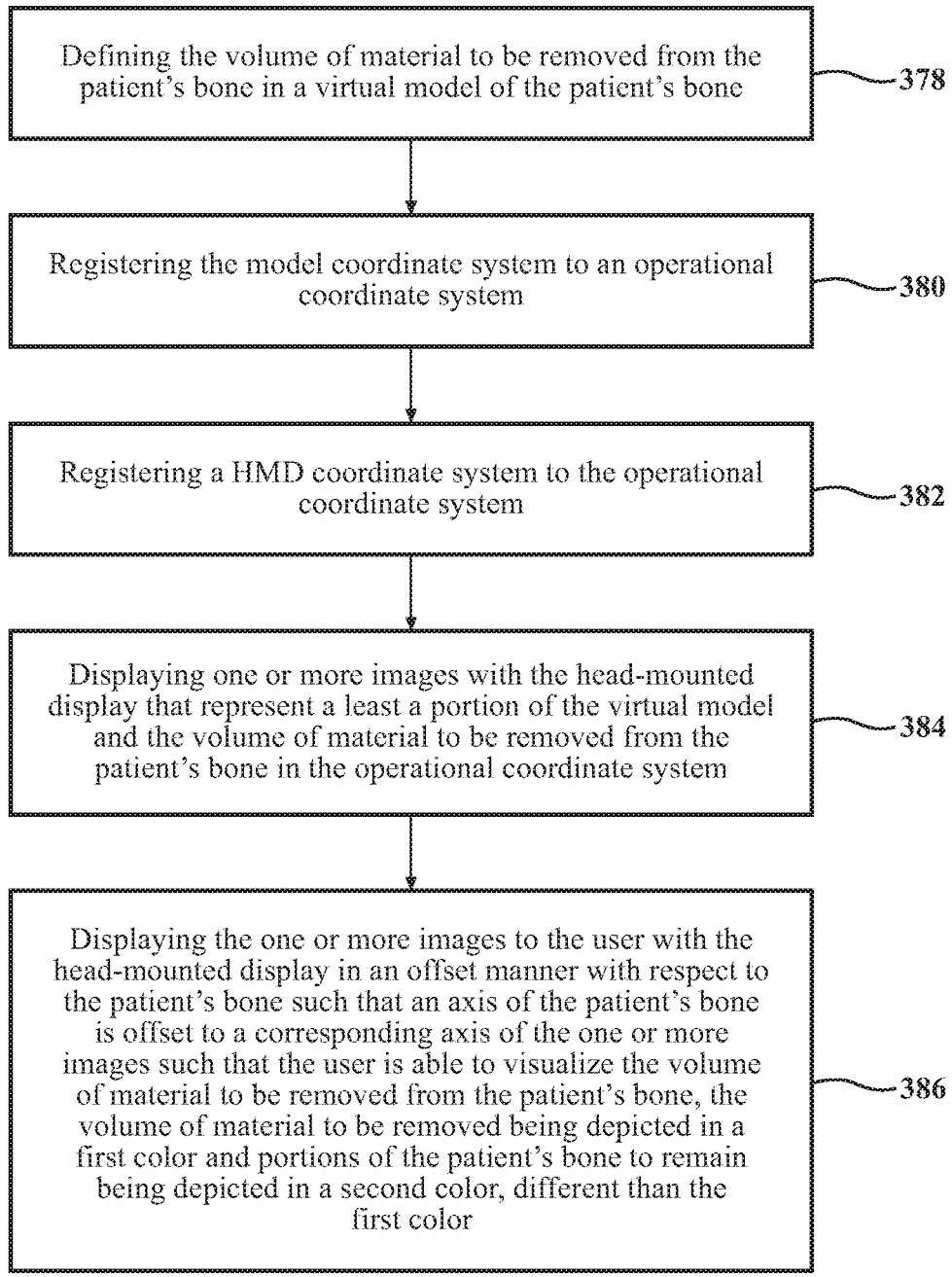

Referring to FIG. 41, a method of visually representing the volume of material to be removed from the patient's bone with the surgical tool is shown. The method comprises, in step 378, defining the volume of material to be removed from the patient's bone in the virtual model of the patient's bone. The virtual model of the patient's bone has the model coordinate system MODEL2. The model coordinate system MODEL2 is registered to the operational coordinate system in step 380 such that the virtual model and the volume of material to be removed from the patient's bone, as defined in the virtual model, are transformed to the operational coordinate system. The HMD coordinate system is registered to the operational coordinate system in step 382. The HMD coordinate system is associated with the HMD 200. One or more images 270 are displayed in step 384 with the HMD 200 that represent at least a portion of the virtual model and the volume of material to be removed from the patient's bone in the operational coordinate system. The one or more images 270 are displayed to the user in step 386 with the HMD 200 in an offset manner with respect to the patient's bone such that the axis of the patient's bone is offset to the corresponding axis of the one or more images 270 such that the user is able to visualize the volume of material to be removed from the patient's bone. The volume of material to be removed is depicted in the first color and portions of the patient's bone to remain are depicted in the second color, different than the first color.

Figure 42:
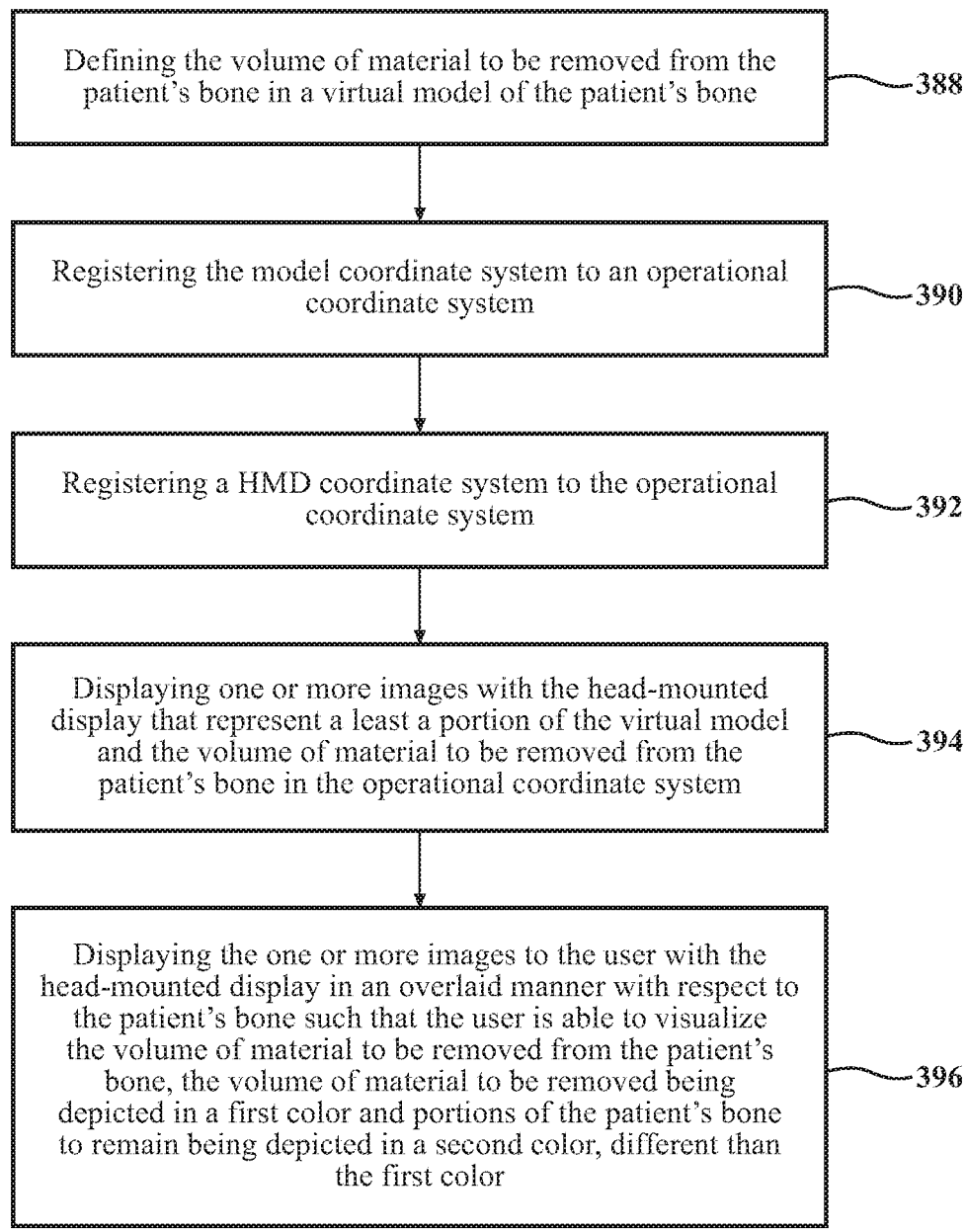

Referring to FIG. 42, another method of visually representing the volume of material to be removed from the patient's bone with the surgical tool is shown. The method comprises, in step 388, defining the volume of material to be removed from the patient's bone in the virtual model of the patient's bone. The virtual model of the patient's bone has the model coordinate system MODEL2. The model coordinate system MODEL2 is registered to the operational coordinate system in step 390 such that the virtual model is transformed to the operational coordinate system. The HMD coordinate system is registered to the operational coordinate system in step 392. The HMD coordinate system is associated with the HMD 200. One or more images 270 are displayed in step 394 with the HMD 200 that represent at least a portion of the virtual model and the volume of material to be removed from the patient's bone in the operational coordinate system. The one or more images 270 are displayed to the user in step 396 with the HMD 200 in an overlaid manner with respect to the patient's bone such that the user is able to visualize the volume of material to be removed from the patient's bone. The volume of material to be removed is depicted in the first color and portions of the patient's bone to remain are depicted in the second color, different than the first color.

Figure 43:
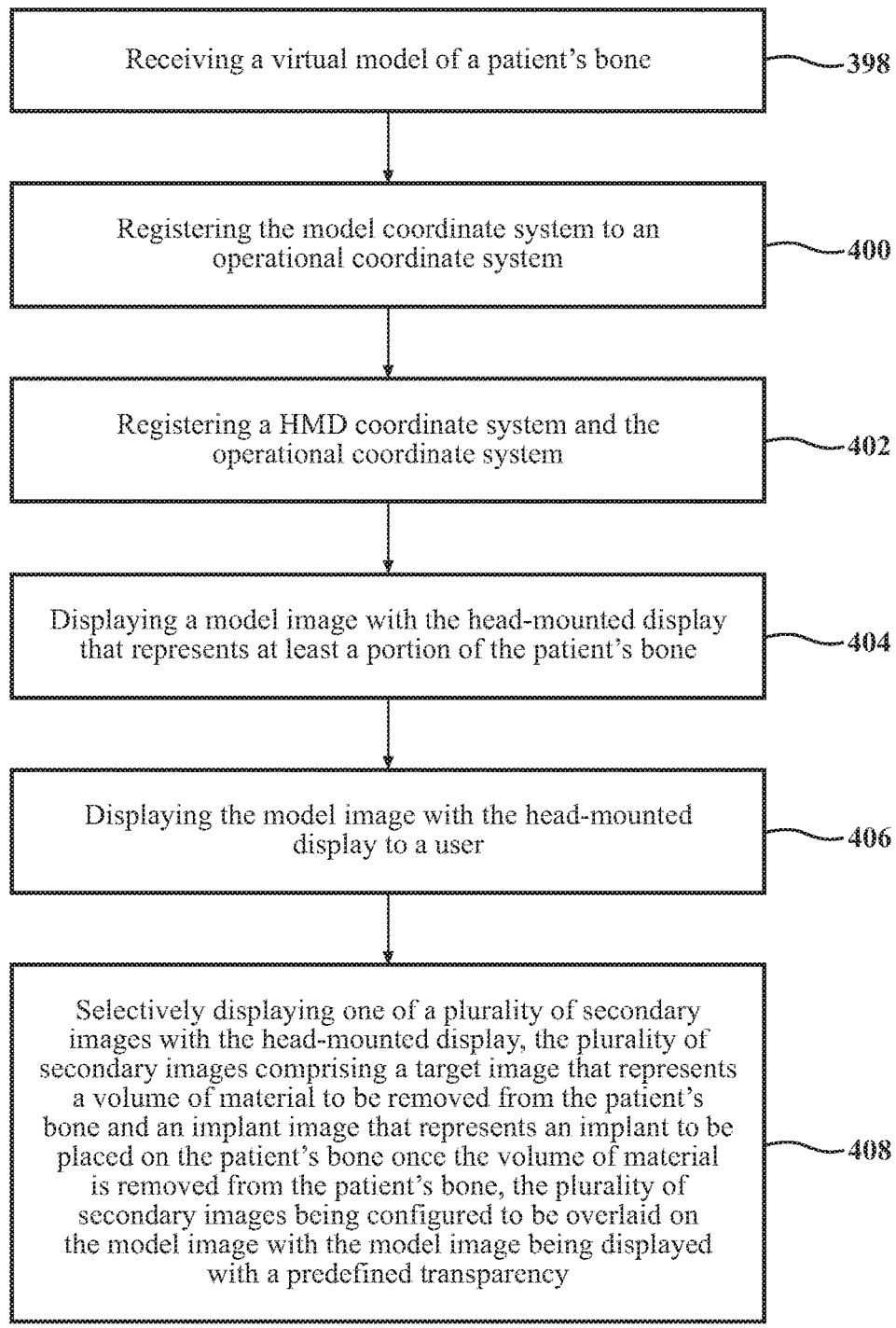

Referring to FIG. 43, a method of visually representing the surgical plan for the surgical procedure is shown. The method comprises, in step 398, receiving the virtual model of the patient's bone. The virtual model has the model coordinate system MODEL2. The model coordinate system MODEL2 is registered to the operational coordinate system in step 400. The HMD coordinate system and the operational coordinate system are registered in step 402. The HMD coordinate system is associated with the HMD 200. The model image 274 is displayed with the HMD 200 in step 404 that represents at least a portion of the patient's bone. The model image 274 is displayed with the HMD 200 to the user in step 406. One of the plurality of secondary images 272, 276 are selectively displayed with the HMD 200 in step 408. The plurality of secondary images 272, 276 comprises the target image 276 that represents the volume of material to be removed from the patient's bone and the implant image 272 that represents the implant to be placed on the patient's bone once the volume of material is removed from the patient's bone. The plurality of secondary images 272, 276 are configured to be overlaid on the model image 274 with the model image being displayed with the predefined transparency.

Figure 44:
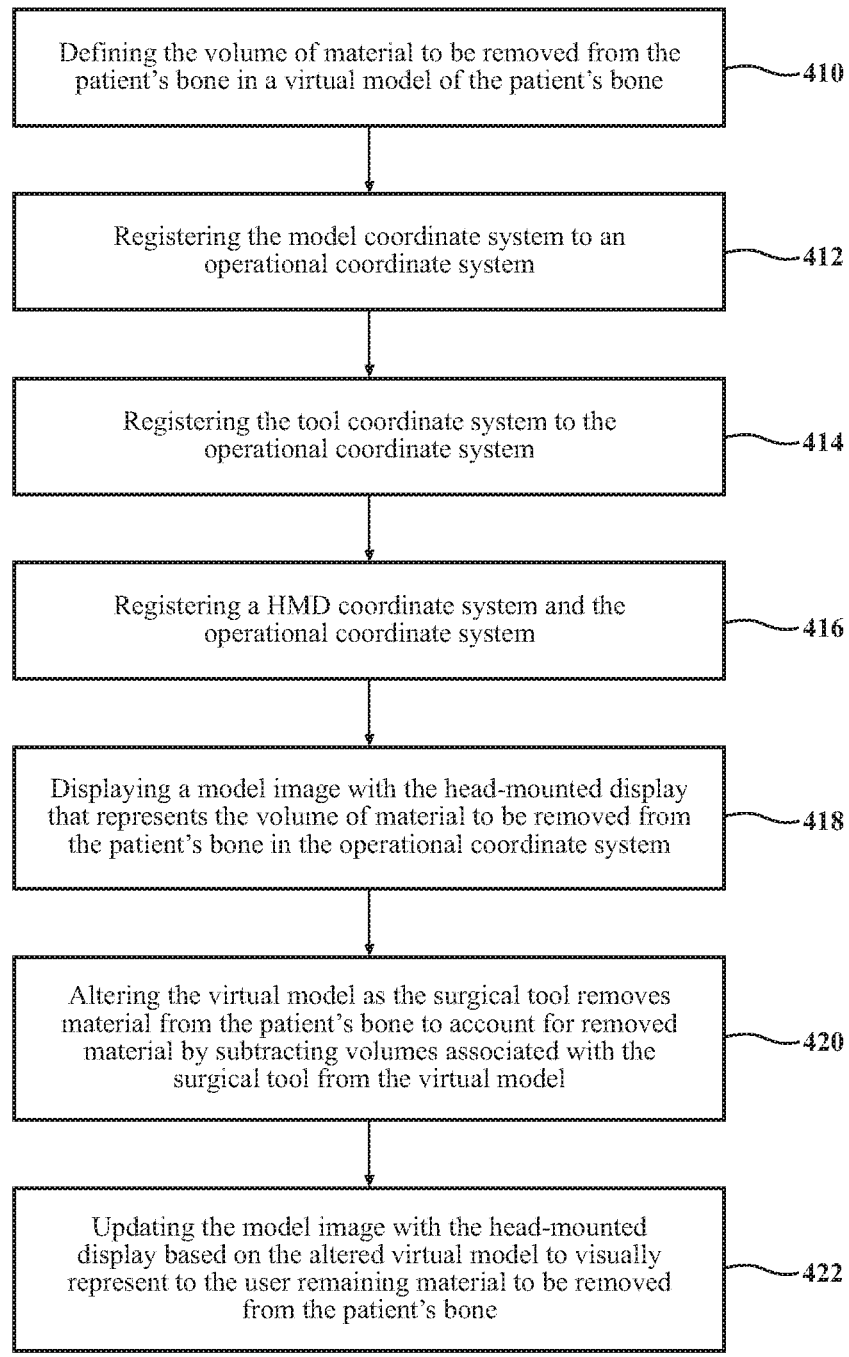

Referring to FIG. 44, another method of visually representing the volume of material to be removed from the patient's bone with the surgical tool is shown. The surgical tool 22 has the tool coordinate system EAPP. The method comprises, in step 410, defining the volume of material to be removed from the patient's bone in the virtual model of the patient's bone. The virtual model has the model coordinate system MODEL2. The model coordinate system MODEL2 is registered to the operational coordinate system in step 412. The tool coordinate system EAPP is registered to the operational coordinate system in step 414. The HMD coordinate system and the operational coordinate system are registered in step 416. The HMD coordinate system is associated with the HMD 200. The model image 276 is displayed with the HMD 200 in step 418 that represents the volume of material to be removed from the patient's bone in the operational coordinate system. The virtual model is altered in step 420 as the surgical tool 22 removes material from the patient's bone to account for removed material by subtracting volumes associated with the surgical tool 22 from the virtual model. The model image 276 is updated with the HMD 200 in step 422 based on the altered virtual model to visually represent to the user remaining material to be removed from the patient's bone.

Figure 45:
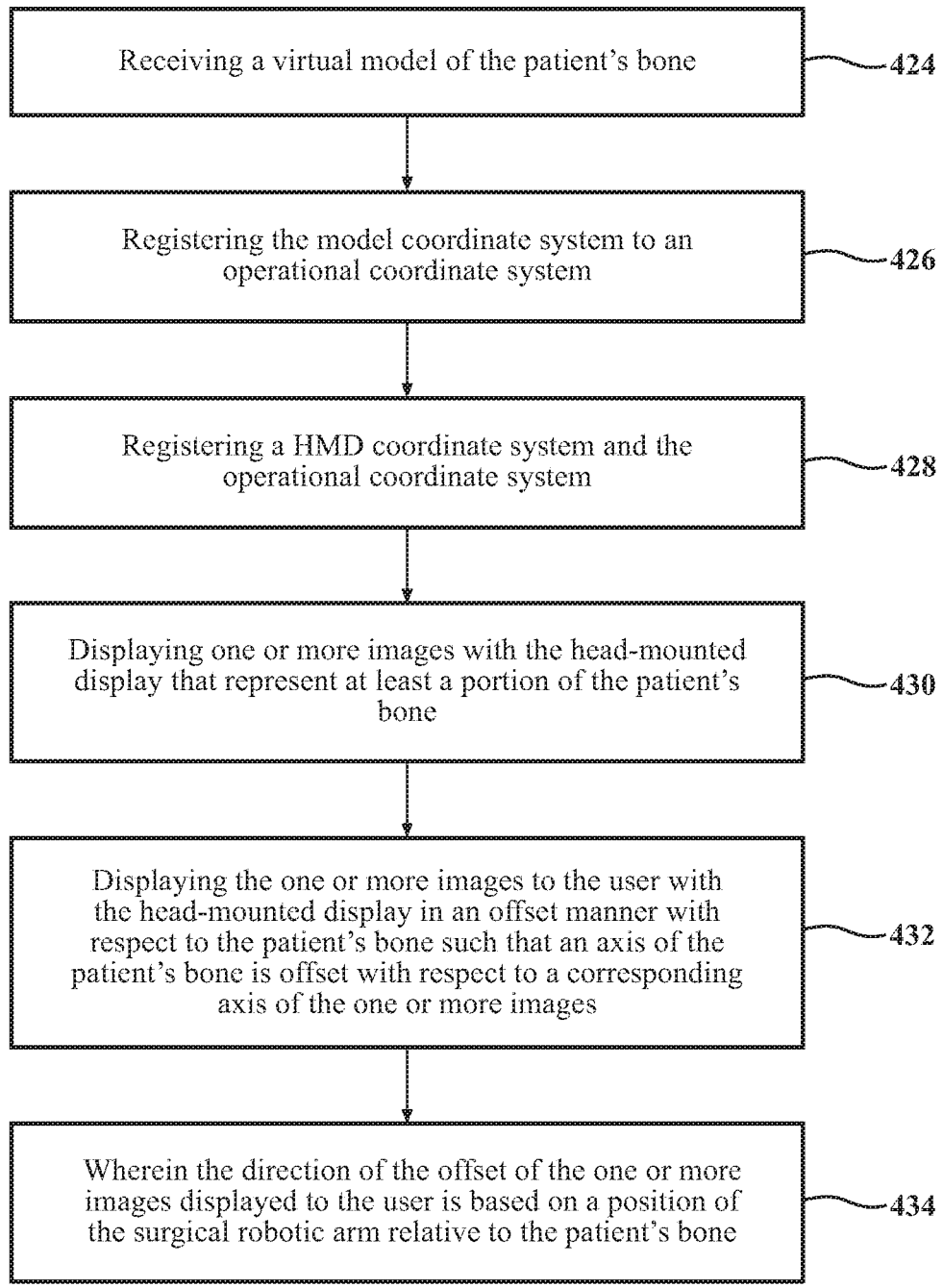

Referring to FIG. 45, a method of visually representing the patient's bone to be treated by the surgical robotic arm is shown. The method comprises receiving the virtual model of the patient's bone. The virtual model has the model coordinate system MODEL2. The model coordinate system MODEL2 is registered to the operational coordinate system. The HMD coordinate system and the operational coordinate system are registered. The HMD coordinate system is associated with the HMD 200. One or more images 262 are displayed with the HMD 200 that represent at least a portion of the patient's bone. The one or more images 262 are displayed to the user with the HMD 200 in an offset manner with respect to the patient's bone such that the axis of the patient's bone is offset with respect to the corresponding axis of the one or more images. The direction of the offset of the one or more images displayed to the user is based on the position of the surgical robotic arm relative to the patient's bone.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of calibrating registration of a HMD coordinate system and a localizer coordinate system, the HMD coordinate system being associated with a head-mounted display and the localizer coordinate system being associated with a surgical navigation localizer, said method comprising the steps of:
    obtaining a registration of the HMD coordinate system and the localizer coordinate system such that images displayed by the head-mounted display can be associated with real objects tracked by the localizer;
    indicating a registration error to a user using at least one real calibration marker viewable by the user and at least one virtual calibration marker image displayed to the user, wherein the at least one virtual calibration marker image has a congruency with the at least one real calibration marker so that the at least one virtual calibration marker image is capable of being aligned with the at least one real calibration marker whereby a magnitude of misalignment is indicative of the registration error; and
    calibrating the registration of the HMD coordinate system and the localizer coordinate system to reduce the registration error by receiving input from the user associated with adjusting a position of the at least one virtual calibration marker image relative to the at least one real calibration marker to better align the at least one virtual calibration marker image with the at least one real calibration marker.

2. The method of claim 1, wherein the at least one real calibration marker is tracked by the localizer.

3. The method of claim 1, wherein at least one real object is tracked by the localizer, the at least one real object having a predetermined spatial relationship to the at least one real calibration marker.

4. The method of claim 1, wherein the method is started in response to the user directing a viewing direction of the user toward the real calibration markers, wherein the head-mounted display is configured to be worn by the user.

5. The method of claim 1, wherein receiving input from the user comprises receiving input that defines coordinates of the at least one virtual calibration marker image in the localizer coordinate system.

6. A method of calibrating registration of a HMD coordinate system and a localizer coordinate system, the HMD coordinate system being associated with a head-mounted display and the localizer coordinate system being associated with a surgical navigation localizer, said method comprising the steps of:
    registering the HMD coordinate system and the localizer coordinate system such that images displayed by the head-mounted display can be associated with real objects tracked by the localizer;
    indicating a registration error to the user using a plurality of real calibration markers viewable by the user and a plurality of virtual calibration marker images displayed to the user, wherein the virtual calibration marker images have a congruency with the real calibration markers so that the virtual calibration marker images are capable of being aligned with the real calibration markers whereby a magnitude of misalignment is indicative of the registration error; and
    calibrating the registration of the HMD coordinate system and the localizer coordinate system to reduce the registration error by receiving input from the user associated with adjusting positions of the virtual calibration marker images relative to the real calibration markers to better align the virtual calibration marker images with the real calibration markers.

7. The method of claim 6, wherein the at least one real calibration marker is tracked by the localizer.

8. The method of claim 6, wherein at least one real object is tracked by the localizer, the at least one real object having a predetermined spatial relationship to the at least one real calibration marker.

9. The method of claim 6, wherein the step of registering is performed in response to the user directing the head-mounted display toward the real calibration markers.

10. The method of claim 6, wherein the step of registering is performed in response to the user directing the head-mounted display toward the real calibration markers so that the real calibration markers are within images captured by a camera comprised in the head-mounted display.

11. The method of claim 6, wherein the step of registering is performed in response to one or more position sensors comprised in the surgical navigation localizer sensing tracking markers comprised in a registration device, wherein the registration device further comprises the real calibration markers.

12. The method of claim 6, wherein receiving input from the user comprises receiving input that alters coordinates of the virtual calibration marker images in the localizer coordinate system.

13. The method of claim 12, wherein receiving input from the user comprises receiving input that alters the coordinates by incremental amounts in any one or more of three directions corresponding to x, y and/or z-axes of the localizer coordinate system.

14. The method of claim 6, wherein the real calibration markers are similar to registration markers used in registering the HMD coordinate system and the localizer coordinate system.

15. The method of claim 1, wherein the at least one real calibration marker is tracked by the localizer and wherein the method is started in response to the user directing a viewing direction of the user toward the real calibration markers, wherein the head-mounted display is configured to be worn by the user.

16. The method of claim 1, wherein at least one real object is tracked by the localizer, the at least one real object having a predetermined spatial relationship to the at least one real calibration marker and wherein the method is started in response to the user directing a viewing direction of the user toward the real calibration markers, wherein the head-mounted display is configured to be worn by the user.

17. The method of claim 6, wherein the at least one real calibration marker is tracked by the localizer and wherein the step of registering is performed in response to the user directing the head-mounted display toward the real calibration markers.

18. The method of claim 6, wherein at least one real object is tracked by the localizer, the at least one real object having a predetermined spatial relationship to the at least one real calibration marker and wherein the step of registering is performed in response to the user directing the head-mounted display toward the real calibration markers.

* * * * *